US00RE48959E

(19) United States
(12) Reissued Patent
Smith et al.

(10) Patent Number: US RE48,959 E
(45) Date of Reissued Patent: Mar. 8, 2022

(54) HUMANIZED ANTIBODIES TO LIV-1 AND USE OF SAME TO TREAT CANCER

(71) Applicant: SEAGEN INC., Bothell, WA (US)

(72) Inventors: Maria Leia Smith, Bothell, WA (US); Django Sussman, Bothell, WA (US); William Arthur, Bothell, WA (US); Albina Nesterova, Bothell, WA (US)

(73) Assignee: SEAGEN INC., Bothell, WA (US)

(21) Appl. No.: 15/862,389

(22) Filed: Jan. 4, 2018

Related U.S. Patent Documents

Reissue of:
(64) Patent No.: 9,228,026
Issued: Jan. 5, 2016
Appl. No.: 13/990,778
PCT Filed: Dec. 6, 2011
PCT No.: PCT/US2011/063612
§ 371 (c)(1),
(2) Date: May 30, 2013
PCT Pub. No.: WO2012/078688
PCT Pub. Date: Jun. 14, 2012

U.S. Applications:
(60) Provisional application No. 61/420,291, filed on Dec. 6, 2010, provisional application No. 61/446,990, filed on Feb. 25, 2011.

(51) Int. Cl.

| | |
|---|---|
| ***C07K 16/28*** | (2006.01) |
| ***A61K 47/68*** | (2017.01) |
| ***C07K 16/30*** | (2006.01) |
| ***C07K 16/46*** | (2006.01) |
| *A61K 39/00* | (2006.01) |

(52) U.S. Cl.
CPC ..... *C07K 16/28* (2013.01); *A61K 47/6865* (2017.08); *C07K 16/3015* (2013.01); *C07K 16/3053* (2013.01); *C07K 16/3069* (2013.01); *C07K 16/465* (2013.01); *A61K 2039/505* (2013.01); *C07K 2317/24* (2013.01); *C07K 2317/52* (2013.01); *C07K 2317/56* (2013.01); *C07K 2317/565* (2013.01); *C07K 2317/732* (2013.01); *C07K 2317/92* (2013.01)

(58) Field of Classification Search
CPC ..... A61K 47/6865; A61K 2039/505; A61P 17/00; A61P 35/00; A61P 15/00; A61P 13/08; C07K 16/465; C07K 16/28; C07K 16/3069; C07K 16/3053; C07K 16/3015; C07K 2317/92; C07K 2317/24; C07K 2317/56; C07K 2317/565; C07K 2317/52; C07K 2317/732
See application file for complete search history.

(56) References Cited

U.S. PATENT DOCUMENTS

| | | | |
|---|---|---|---|
| 4,880,935 | A | 11/1989 | Thorpe |
| 5,122,368 | A | 6/1992 | Greenfield et al. |
| 5,514,554 | A | 5/1996 | Bacus |
| 5,622,929 | A | 4/1997 | Willner et al. |
| 5,693,465 | A | 12/1997 | Manning et al. |
| 5,824,805 | A | 10/1998 | King et al. |
| 6,066,778 | A | 5/2000 | Ginsburg |
| 6,130,237 | A | 10/2000 | Denny et al. |
| 6,214,345 | B1 | 4/2001 | Firestone et al. |
| 6,468,790 | B1 | 10/2002 | Giese |
| 6,762,020 | B1 | 7/2004 | Mack et al. |
| 6,884,869 | B2 | 4/2005 | Senter |
| 7,022,500 | B1 | 4/2006 | Queen et al. |
| 7,091,186 | B2 | 8/2006 | Senter |
| 7,098,308 | B2 | 8/2006 | Senter |
| 7,141,549 | B2 | 11/2006 | Mezes |
| 7,285,382 | B2 | 10/2007 | de Sauvage et al. |
| 7,288,248 | B2 | 10/2007 | Bhaskar et al. |
| 7,494,775 | B2 | 2/2009 | Veiby et al. |
| 7,498,298 | B2 | 3/2009 | Doronina et al. |
| 7,501,121 | B2 | 3/2009 | Tchistiakova et al. |
| 7,659,241 | B2 | 2/2010 | Senter et al. |
| 7,691,566 | B2 | 4/2010 | De Sauvage |
| 7,705,120 | B2 | 4/2010 | Lillie |
| 7,982,015 | B2 | 7/2011 | de Sauvage et al. |
| 8,313,745 | B2 | 11/2012 | Mack et al. |
| 8,323,906 | B2 | 12/2012 | Veiby et al. |
| 8,591,863 | B2 | 11/2013 | Law et al. |
| 8,642,270 | B2 | 2/2014 | Leyland-Jones et al. |
| 8,728,730 | B2 | 5/2014 | Dennis, Jr. et al. |
| 8,906,342 | B2 | 12/2014 | Law et al. |
| 9,228,026 | B2 | 1/2016 | Smith et al. |
| 9,783,608 | B2 | 10/2017 | Smith et al. |
| 10,533,227 | B2 | 1/2020 | Veiby et al. |
| 2003/0215457 | A1 | 11/2003 | De Sauvage |
| 2004/0096392 | A1 | 5/2004 | Bhaskar et al. |
| 2004/0141983 | A1 | 7/2004 | Law et al. |
| 2004/0258616 | A1 | 12/2004 | McLachlan et al. |
| 2005/0238649 | A1 | 10/2005 | Doronina et al. |
| 2006/0074008 | A1 | 4/2006 | Senter et al. |
| 2006/0222653 | A1 | 10/2006 | Abel et al. |
| 2006/0286112 | A1 | 12/2006 | Kellermann et al. |
| 2007/0264267 | A1 | 11/2007 | De Sauvage |

(Continued)

FOREIGN PATENT DOCUMENTS

| | | | |
|---|---|---|---|
| CN | 1849337 | A | 10/2006 |
| EP | 1263780 | A2 | 12/2012 |
| KP | 102005010267 | A | 10/2005 |
| WO | WO199818945 | A1 | 5/1998 |
| WO | WO199834118 | A1 | 8/1998 |

(Continued)

OTHER PUBLICATIONS

Almagro, J.C. et al. (Jan. 1, 2008). "Humanization of Antibodies," *Frontiers in Bioscience*13:1619-1633.

Amsberry, K.L. et al. (Nov. 1990). "The Lactonization of 2'-Hydroxyhydrocinnamic Acid Amides: A Potential Prodrug for Amines," *The Journal of Organic Chemistry* 55(23):5867-5877.

(Continued)

*Primary Examiner* — Sharon Turner
(74) *Attorney, Agent, or Firm* — Morrison & Foerster LLP

(57) ABSTRACT

The invention provides humanized antibodies that specifically bind to LIV-1. The antibodies are useful for treatment and diagnoses of various cancers as well as detecting LIV-1.

124 Claims, 29 Drawing Sheets

Specification includes a Sequence Listing.

(56) References Cited

U.S. PATENT DOCUMENTS

| | | | |
|---|---|---|---|
| 2008/0138345 | A1 | 6/2008 | De Sauvage |
| 2008/0171039 | A1 | 7/2008 | Law et al. |
| 2008/0175839 | A1 | 7/2008 | Law et al. |
| 2010/0158909 | A1 | 6/2010 | McDonagh et al. |
| 2010/0158919 | A1 | 6/2010 | Dauphin et al. |
| 2010/0196377 | A1 | 8/2010 | Jantapour et al. |
| 2011/0165566 | A1 | 7/2011 | Wittliff et al. |
| 2011/0166838 | A1 | 7/2011 | Gehrmann et al. |
| 2011/0195995 | A1 | 8/2011 | Wittliff et al. |
| 2011/0280892 | A1 | 11/2011 | Kinch |
| 2013/0102482 | A1 | 4/2013 | Veiby et al. |
| 2013/0259860 | A1 | 10/2013 | Smith |
| 2014/0037540 | A1 | 2/2014 | Law et al. |
| 2014/0127239 | A1 | 5/2014 | Howard |
| 2016/0185858 | A1 | 6/2016 | Smith |
| 2018/0079810 | A1 | 3/2018 | Smith et al. |
| 2019/0085091 | A1 | 3/2019 | Sussman |
| 2020/0165335 | A1 | 5/2020 | Smith |

FOREIGN PATENT DOCUMENTS

| | | | |
|---|---|---|---|
| WO | WO199923230 | A1 | 5/1999 |
| WO | WO199925877 | A1 | 5/1999 |
| WO | WO199933869 | A2 | 7/1999 |
| WO | WO199933869 | A3 | 12/1999 |
| WO | WO200008210 | A1 | 2/2000 |
| WO | 200055174 | A1 | 9/2000 |
| WO | WO-2001/055178 | A2 | 8/2001 |
| WO | WO-2001/055178 | A3 | 8/2001 |
| WO | WO2001096372 | A2 | 12/2001 |
| WO | WO2001096372 | A3 | 12/2001 |
| WO | WO2003075855 | A2 | 9/2003 |
| WO | WO2003075855 | A3 | 9/2003 |
| WO | WO2004010957 | A2 | 2/2004 |
| WO | WO2004010957 | A3 | 2/2004 |
| WO | WO-2004/066933 | A2 | 8/2004 |
| WO | WO-2004/067564 | A2 | 8/2004 |
| WO | WO-2005/058961 | A2 | 6/2005 |
| WO | WO-2007/120787 | A2 | 10/2007 |
| WO | WO-2008/131376 | A2 | 10/2008 |
| WO | WO-2012/078688 | A2 | 6/2012 |
| WO | 2012125712 | A2 | 9/2012 |
| WO | 2012125712 | A3 | 12/2012 |
| WO | WO2017161007 | A1 | 9/2017 |
| WO | WO-2009/068649 | A2 | 12/2017 |
| WO | 2019109007 | A1 | 6/2019 |
| WO | 2020095249 | A1 | 5/2020 |
| WO | 2020249483 | A1 | 12/2020 |

OTHER PUBLICATIONS

Balmaña, J. et al. (May 2009). "BRCA in breast cancer: ESMO Clinical Recommendations," *Annals of Oncology* 20 (supp 4):iv19-iv20.

Brown, M. et al. (May 1, 1996). "Tolerance of single, but not multiple, amino acid replacements in antibody VH CDR 2: a means of minimizing B cell wastage from somatic hypermutation?," *J. Immunol.* 156(9):3285-3291.

Chari, R.V.J. et al. (Jan. 1, 1992). "Immunoconjugates Containing Novel Maytansinoids: Promising Anticancer Drugs," *Cancer Research* 52:127-131.

Dressman, M.A. et al. (2001). "Genes that Co-cluster with Estrogen Receptor Alpha in Microarray Analysis of Breast Biopsies," *The Pharmacogenomics Journal* 1(2):135-141.

Dubowchik, G.M. et al. (Aug. 1999). "Receptor-Mediated and Enzyme-Dependent Targeting of Cytotoxic Anticancer Drugs," *Pharm. Therapeutics* 83(2):67-123.

El-Tanani, M.K. et al. (Jul. 23, 1996)."Insulin/IGF-1 Modulation of the Expression of two Estrogen-induced Genes in MCF-7 Cells" *Molecular and Cellular Endocrinology* 121(1):29-35.

El-Tanani, M.K. et al. (Mar. 1997). "Interaction Between Estradiol and Growth Factors in the Regulation of Specific Gene Expression in MCF-7 Human Breast Cancer Cells," *J. Steroid Biochem. Molec. Biol.* 60(5-6):269-276.

El-Tanani, M.K. et al. (Nov. 29, 1996). "Interaction Between Estradiol and cAMP in the Regulation of Specific Gene Expression," *Molecular and Cellular Endocrinology* 124(1-2):71-77.

Forero, A. et al. (Dec. 6-10, 2016). "Phase 1 Study of the Antibody-Drug Conjugate (ADC) SGN-LIV1A in Patients with Heavily Pretreated Metastatic Breast Cancer," Poster-Abstract No. P6-12-04, *Presented at* Session: 621—ew Drug and Treatment Strategies, San Antonio Breast Cancer Symposium; N, San Antonio, TX, three pages.

Forero, A. et al. (Dec. 8-12, 2015). "Interim Analysis of a Phase 1 Study of the Antibody-Drug Conjugate SGN-LIV1A in Patients with Metastatic Breast Cancer," Poster-Abstract No. 638, *Presented at* Session: 621—New Drug and Treatment Strategies, San Antonio Breast Cancer Symposium; San Antonio, TX, three pages.

Forero, A. et al. (Dec. 9-13, 2014). "SGN-LIV1A: A Phase 1 Trial Evaluating a Novel Antibody-Drug Conjugate in Patients with LIV-1-Positive Breast Cancer," Poster- Abstract No. 419 *Presented at* San Antonio Breast Cancer Symposium, San Antonio, TX, three pages.

Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," *Bioorganic & Medicinal Chemistry Letters* 9(15):2237-2242.

Johnson, D.A. et al. (Jul.-Aug. 1995). "Anti-Tumor Activity of CC49-Doxorubicin Immunoconjugates," *Anticancer Res.* 15(4):1387-1393.

Kingsbury, W.D. et al. (Nov. 1984). "A Novel Peptide Delivery System Involving Peptidase Activated Prodrugs as Antimicrobial Agents. Synthesis and Biological Activity of Peptidyl Derivatives of 5-Fluorouracil," *Journal of Medicinal Chemistry 27*(11):1447-1451.

Kostic, A. et al. (May 30-Jun. 3, 2014). "SGN-LIV1A, an Antibody-drug Conjugate, in Patients with LIV-1-positive Breast Cancer," Poster—Abstract No. TPS1143, *American Society of Clinical Oncology*, Chicago, IL, one page.

Lau, A. et al. (Oct. 1995). "Conjugation of Doxorubicin to Monoclonal Anti-Carcinoembryonic Antigen Antibody Via Novel Thiol-Directed Cross-Linking Reagents," *Bioorganic & Medicinal Chemistry* 3(10):1299-1304.

Lau, A. et al. (Oct. 1995). "Novel Doxorubicin-Monoclonal Anti-Carcinoembryonic Antigen Antibody Immunoconjugate Activity in vitro," *Bioorganic & Medicinal Chemistry* 3(10):1305-1312.

Li, F. et al. (Apr. 16-20, 2016). "Preclinical Combinations of the Antibody-drug Conjugate SGN-LIV1A with Chemotherapies Show Increased Activity," Poster—Abstract No. 2966 *Presented at* AACR Annual Meeting, New Orleans, LA, two pages.

Lue, H.-W. et al. (Apr. 12-16). "LIV-1 Mediates Epithelial to Mesenchymal Transition and Correlates with Prostatic Cancer Progression," AACR, Annual Meeting, Abstract No. 5373, 1 page.

Manning, D.L. et al. (1994). "Oestrogen-regulated Genes in Breast Cancer: Association of pLIV1 With Lymph Node Involvement," *European Journal of Cancer* 30A(5):675-678.

Modi, S. et al. (Dec. 5-7, 2017). "Phase 1 Study of the Antibody-Drug Conjugate Ladiratuzumab Vedotin (SGN-LIV1A) in Patients with Heavily Pretreated Triple-Negative Metastatic Breast Cancer," Abstract No. PD3-14 *Presented at* Session 621, New Drugs and Treatment Strategies, San Antonio Breast Cancer Symposium, San Antonio, TX, three pages.

Neville, D.M. et al. (Sep. 5, 1989). "Enhancement of Immunotoxin Efficacy by Acid-cleavable Crosslinking Agents Utilizing Diphtheria Toxin and Toxin Mutants," *The Journal of Biological Chemistry* 264(25):14653-14661.

Pollack, V.A. et al. (Aug. 2007). "Treatment Parameters Modulating Regression of Human Melanoma Xenografts by an Antibody—drug Conjugate (CR011-vcMMAE) Targeting GPNMB," *Cancer Chemother. Pharmacol.* 60(3):423-435.

(56) References Cited

OTHER PUBLICATIONS

Reichert, J.M. et al. (May 2007). "Development Trends for Monoclonal Antibody Cancer Therapeutics," *Nat. Rev. Drug Disc.* 6(5):349-356.
Rodrigues, M.L. et al. (Apr. 1995). "Synthesis and β-lactamase-mediated Activation of a Cephalosporin-Taxol Prodrug," *Chemistry & Biology* 2(4):223-227.
Rudikoff, S. et al. (Mar. 1, 1982). "Single Amino Acid Substitution Altering Antigen-binding Specificity," *Proc. Nat'l Acad. Sci. USA* 79(6):1979-1983.
Smith, L.M. et al. (Dec. 8-12, 2010). "LIV-1 Antibody-Drug Conjugate: A Novel Therapeutic Agent for Breast Cancer," Presented at CTRC-AACR San Antonio Breast Cancer Symposium, Cancer Res 70(24 Suppl):Abstract nr. P6-15-16, one page.
Storm, D.R. et al. (Aug. 1972). "Effect of Small Changes in Orientation on Reaction Rate," *Journal of the American Chemical Society* 94(16):5815-5825.
Sussman, D. et al. (2014; e-published on Sep. 24, 2014). "SGN-LIV1A: A Novel Antibody—Drug Conjugate Targeting LIV-1 for the Treatment of Metastatic Breast Cancer," *Molecular Cancer Therapeutics* 13(12):2991-3000.
Sussman, D. et al. (Apr. 2-6, 2011). "LIV-1 Antibody-Drug Conjugate: A Novel Therapeutic Agent for Breast and Prostate Cancer," Poster—Abstract No. 3620 *Presented at* AACR, one pages.
Sussman, D. et al. (Apr. 6-10, 2013)."SGN-LIV1A: A Development Stage Antibody-Drug Conjugate Targeting LIV-1 for the Treatment of Metastatic Breast Cancer," *Presented at* AACR, Annual Meeting, *Cancer Res* 73(8 Suppl):Abstract No. 3962, 1 page.
Taylor, K.M. (Apr. 2000). "Hypothesis Paper: LIV-1 Breast Cancer Protein Belongs to New Family of Histidine-Rich Membrane Proteins with Potential to Control Intracellular Zn2+ Homeostasis," *IUBMB Life* 49(4):249-253.
Taylor, K.M. et al. (Apr. 1, 2003). "The LZT Proteins; the LIV-1 Subfamily of Zinc Transporters," *Biochimica et Biophysica Acta* 1611(1-2):16-30.
Taylor, K.M. et al. (Nov. 2003). "Structure-function Analysis of LIV-1, the Breast Cancer-associated Protein that Belongs to a New Subfamily of Zinc Transporters," *Biochem. J.* 375(1):51-59.
Thorpe, P.E. et al. (Nov. 15, 1987). "New Coupling Agents for the Synthesis of Immunotoxins Containing a Hindered Disulfide Bond with Improved Stability in Vivo," *Cancer Research* 47:5924-5931.
TSE, K.F. et al. (Feb. 15, 2006). "CR011, a Fully Human Monoclonal Antibody-Auristatin E Conjugate, for the Treatment of Melanoma," *Clin. Cancer Res* 12(4):1373-1382.
Unno, J. et al. (Oct. 2009). "LIV-1 Enhances the Aggressive Phenotype Through the Induction of Epithelial to Mesenchymal Transition in Human Pancreatic Carcinoma Cells," *International Journal of Oncology* 35(4):813-821.
EPO Application No. 11847198.6, European Search Report and Supplementary European Search Opinion dated Apr. 16, 2015.
EPO Application No. EP16200557.3, European Search Report and Written Opinion of the International Searching Authority dated Jan. 25, 2017.
U.S. Appl. No. 13/990,778, Non-Final Office Action dated Apr. 14, 2015.
U.S. Appl. No. 13/990,778, Notice of Allowance dated Sep. 18, 2015.
U.S. Appl. No. 14/052,905, Non-Final Office Action dated Feb. 25, 2014.
U.S. Appl. No. 14/052,905, Notice of Allowance dated Aug. 8, 2014.
U.S. Appl. No. 14/052,905, Requirement for Restriction/Election dated Nov. 12, 2013.
U.S. Appl. No. 14/948,183, Non-Final Office Action dated Feb. 2, 2017.
U.S. Appl. No. 14/948,183, Notice of Allowance dated May 31, 2017.
WIPO Application No. PCT/US2011/063612, PCT International Preliminary Report on Patentability dated Jun. 20, 2013.
WIPO Application No. PCT/US2011/063612, PCT International Search Report and Written Opinion of the International Searching Authority dated Jun. 27, 2012.
Anonymous (Feb. 25, 2016). "A Safety Study of SGN-LIV1A in Breast Cancer Patients History of Changes for the Study: NCT01969643," retrived from URL:https://clinicaltrials.gov/ct2/history/NTC01969643?A=32&C=Side-by-Side#StudyPageTop, last visited Oct. 17, 2019, 7 pages.
Bedognetti, D. et al. (2016, e-pub. Apr. 26, 2016). "Checkpoint Inhibitors and Their Application in Breast Cancer," Breast Care 11(2):108-115.
Cao, A. et al.(Aprii 20, 2016). "Abstract 4914: Auristatin-Based Antibody Drug Conjugates Activate Multiple ER Stress Response Pathways Resulting in Immunogenic Cell Death and Amplified T-Cell Responses," Retrieved from the Internet: URL:https://cancerres.aacrjournals.org/content/76/14_Supplement/4914, last visited Mar. 6, 2020, 4 pages.
Cherkassky, M. (2003). "Doxycycline," in RLE Drug Encyclopedia ed.10, pp. 299-300, 9 pages.
Extended Search Report, dated Apr. 6, 2020, for European Patent Application No. 17767448.8, 17 pages.
Hurvitz, S.A. et al. (Mar. 20, 2013, e-pub. Feb. 4, 2013), "Phase II Randomized Study of Trastuzumab Emtansine Versus Trastuzumab Plus Docetaxel in Patients With Human Epidermal Growth Factor Receptor 2-Positive Metastatic Breast Cancer," Journal of Clinical Oncology 31(9):1157-1163.
Müller, P. et al. (Aug. 1, 2014). "Cancer Chemotherapy Agents Target Intratumoral Dendritic Cells to Potentiate Antitumor Immunity," OncoImmunology 3(8):e954460, 3 pages.
Nanda, R. et al. (Jul. 20, 2016, e-pub. May 2, 2016). "Pembrolizumab in Patients With Advanced Triple-Negative Breast Cancer: Phase lb Keynote-012 Study," J. Clin. Oncology 34(21):2460-2467.
Partial Supplementary European Search Report, dated Nov. 27, 2019, for European Patent Application No. 17767448.8, 16 pages.
Poole, R.M. (2014, e-pub. Oct. 21, 2014). "Pembrolizumab: First Global Approval," Drugs 74:1973-1981.
Slamon, D.J. et al. (Mar. 15, 2001). "Use of Chemotherapy Plus a Monoclonal Antibody Against HER2 for Metastatic Breast Cancer That Overexpresses HER2" The New England Journal of Medicine 344(11):783-792.
Swain, S.M. et al. (May 2013, e-pub. Apr. 18, 2013). "Pertuzumab, Trastuzumab, and Docetaxel for HER2-Positive Metastatic Breast Cancer (Cleopatra Study); Overal Survival Results From a Randomised, Double-Blind, Placebo-Controlled Phase 3 Study," Lancet Oncol. 14:461-471.
Wang, H. et al. (Mar. 1, 2004). "Pretreatment With Dexamethasone Increase Antitumor Activity of Carboplatin and Gemcitabine in Mice Bearing Human Cancer Xenografts: In Vivo Activity, Pharmacokinetics, and Clinical Implications for Cancer Chemotherapy," Clinical Cancer Research 10(5):1633-1644.
Bhaskar, V. et al. (Oct. 1, 2003). "E-Selectin Up-Regulation Allows for Targeted Drug Delivery in Prostate Cancer," Cancer Research63:6387-6394.
Börresen-Dale, A-L. (2003). "Genetic Profiling of Breast Cancer: From Molecular Portraits to Clinical Utility," International Journal of Biological Markers 18(1):54-56.
Chou, T.-C. (Jan. 15, 2010, e-pub. Jan. 12, 2010). "Drug Combination Studies and Their Synergy Quantification Using the Chou-Talaly Method," Cancer Res 70(2): 440-446.
Derisi, J. et al. (Dec. 1996). "Use of a cDNA Microarray to Analyse Gene Expression Patterns in Human Cancer," Nature Genetics 14:457-460.
Doronina S.O. et al. (2003). "Development of potent monoclonal antibody auristatin conjugates for cancer therapy,"Nature Biotechnol. 21(7):778-784.
EMBL Database, (Dec. 23, 1995). Accession No. U41060.
EPO Application No. 18204152.5, European Extended Search Report dated Dec. 4, 2018.
Francisco, J.A. et al. (2003, e-pub. May 8, 2003). "cAC10-vcMMAE, an Anti-CD30-Monomethyl Auristatin E Conjugate With Potent and Selective Antitumor Activity," Blood 102:1458-1465.
Khan, J. et al. (1999). "Epression profiling in cancer using cDNA microarrays," Electrophoresis 20:223-229.

(56) References Cited

OTHER PUBLICATIONS

King, D.J. et al. (1992). "Expression, purification and characterization of a mouse-human chimeric antibody and chimeric Fab' fragment," Biochem. J. 281:317-323.
Kobayashi, M. et al. (Mar. 1997). "Antitumor Activity of TZT-1027, a Novel Dolastatin 10 Derivative," Jpn J Cancer Res. 88:316-327.
Kostelny, S.A. et al. (Mar. 1, 1992). "Formation of a Bispecific Antibody by the Use of Leucine Zippers," J. Immunol. 148(5): 1547-1553.
Liefers, G.-J. et al. (Jul. 23, 1998). "Micrometastases and Survival in Stage II Colorectal Cancer," New England J. Med. 339(4):223-228.
McClelland, R.A. et al. (1998). "Oestrogen-Regulated Genes in Breast Cancer: Association of pLIVI with Response to EndocrineTherapy," Br. J. Cancer 77(10):1653-1656.
Mohammad, R.M. et al. (1999). "A New Tubulin Polymerization Inhibitor, Auristatin PE, Induces Tumor regression in a Human Waldenstrom's Macroglobulinemia Xenograft Model," Intl J. Oncology 15:367-372.
Payne, J.A. et al. (Jul. 28, 1995). "Primary Structure, Functional Expression, and Chromosomal Localization of the Bumetanide-Sensitive Na-K-Cl Cotransporter in Human Colon," J. Biol. Chem. 270:17977-17985.
Pettit, G.R. et al. (1998). "Antineoplastic Agents 365. Dolastatin 10 SAR probes," Anti-Cancer Design 13:243-277.
Ross, S. et al. (May 1, 2002). "Prostate Stem Cell Antigen as Therapy Target: Tissue Expression and in vivo Efficacy of an Immunoconjugate," Cancer Research 61:2546-2553.
Songsivilai, S. et al. (1990). "Bispecific Antibody: A Tool for Diagnosis and Treatment of Disease," Clin. Exp. Immunol. 79:315-321.
Taylor, K.M. et al. (1999). "The LIV-1 Gene, Implicated in Metastatic Breast Cancer, Codes for a Histidine-Rich Transmembrane Protein," British Journal of Cancer 80(Suppl 2):24.
Vogel, C.-W. (1987). Immunoconjugates: Antibody Conjugates in Radioimaging and Therapy of Cancer, Oxford University Press, New York, Oxford pp. 1-160.
Wawrzynczak et al. (1987). "Methods for Preparing Immunotoxins: Effect of the Linkage on Activity and Stability," In Immunoconjugates: Antibody Conjugates in Radioimagery and Therapy of Cancer, pp. 28-55.
Welford, S.M. et al. (1998). "Detection of Differentially Expressed Genes in Primary Tumor Tissues Using Representational Differences Analysis Coupled to Microarray Hybridization," Nucleic Acids Research 26 (12):3059-3065.
Williams, K. et al. (1998). "Analysis of Differential Expression in Normal and Neoplastic Human Breast Epithelial Cell Lines," Electrophoresis 19:333-343.
WIPO Application No. PCT/US2017/22541, PCT International Search Report and Written Opinion of the International Searching Authority dated Jul. 31, 2012.
Yamamoto, K. et al. (Mar. 1996). "Clinicial Application of Chimeric Monoclonal Antibody A7-NCS Conjugate," Biotherapy 10:365-367, Abstract.
Yang, G.P. et al. (1999). "Combining SSH and cDNA Microarrays for Rapid Identification of Differentially Expressed Genes," Nucleic Acids Research 27(6):1517-1523.
Criscitiello, C. et al. (2015). "Immunotherapy of Breast Cancer," Immuno-Oncology Prog. Tumor Res. 42:30-43.
Almagro & Fransson, Frontiers in Bioscience 2008; 13:1619-33.*
Rudikoff et al., Proc. Nat'l Acad. Sci. USA 1982; 79:1979-83.*
Brown et al., J. Immunol. 1996; 156(9):3285-91.*
Reichert & Valge-Archer, Nat. Rev. Drug Disc. 2007; 6:349-356.*
Tse et al., Clin Cancer Res, 2006; 12(4):1373-82.*
Pollack et al., Cancer Chemother Pharmacol 2007; 60: 423-35.*
Balmana et al. Ann Oncol 2009; 20(supp 4):iv19-20.*
Arnold et al., "Prostate cancer bone metastasis: Reactive oxygen species, growth factors and heparan sulfate proteoglycans provide a signaling triad that supports progression," AACR, Annual Meeting, Abstract No. 4504, 1 page, (2008).
Dressman et al., "Genes that co-cluster with estrogen receptor alpha in microarray analysis of breast biopsies," The Pharmacogenomics Journal, 1:135-141, (2001).
Lue et al., "LIV-1 mediates epithelial to mesenchymal transition and correlates with prostatic cancer progression," AACR, Annual Meeting, Abstract No. 5373, 1 page, (2008).
Smith et al., "LIV-1 Antibody-Drug Conjugate: A Novel Therapeutic Agent for Breast Cancer," CTRC-AACR San Antonio Breast Cancer Symposium, Abstract No. 851651, 1 page, (2010).
U.S. Appl. No. 14/052,905, Response to Non-Final Office Action filed Jun. 19, 2014.
U.S. Appl. No. 14/052,905, Response to Requirement for Restriction/Election filed Dec. 12, 2013.
Unno et al., "LIV-1 enhances the aggressive phenotype through the induction of epithelial to mesenchymal transition in human pancreatic carcinoma cells," International Journal of Oncology, 35: 813-821, (2009).
EPO Application No. 11847198.6, European Search Report and Supplementary European Search Opinion mailed Apr. 16, 2015.
U.S. Appl. No. 14/052,905, Notice of Allowance mailed Aug. 8, 2014.

* cited by examiner

```
                    10        20        30        40        50
            ....|....|....|....|....|....|....|....|....|....|....|....
hLiv-14 HA  QVQLVQSGAEVKKPGASVKVSCKASGYTFTDYYMHWVRQAPGQGLEWMGWIDPENGDTEY
hLiv-14 HB  ............................IE................................
hLiv-14 HC  ............................................................
hLiv-14 HD  ........................F...................................
hLiv-14 HE  ........................FNIE................I.............
BR2-14a     ....Q.....LVRS.....L..T...FNIE.......K.R.K.....I.............
CDRs                                     *****               ***********
            60        70        80        90       100       110
            |....|....|....|....|.......|....|....|....|.......|....|...
hLiv-14 HA  APTFQGRVTMTRDTSISTAYMELSRLRSDDTAVYYCARHDAHYGTWFAYWGQGTLVTVSS
hLiv-14 HB  ................N...........................................
hLiv-14 HC  ......KA...A....................................................
hLiv-14 HD  ....................................NV......................
hLiv-14 HE  ......KA...A....N...................NV......................
BR2-14a     ......KA...A...SN...LQ..S.T.E.......NV.....................A
CDRs        ******                                 ***********

                    10        20              30        40        50
            ....|....|....|....|....|.........|....|....|....|....|....|
hLiv-14 LA  DVVMTQSPLSLPVTLGQPASISCRSSQSIIRNDGNTYLEWFQQRPGQSPRRLIYRVSNRF
hLiv-14 LB  ......................................Y.....................
hLiv-14 LC  ......................................L.....................
hLiv-14 LD  ...................................................K........
hLiv-14 LE  ...................................................L........
hLiv-14 LF  ......................................YL.K.....KL.........
BR2-14a     ..L...T......S..DQ.....................YL.K.....KL.........
CDRs                              ****************                ******

                60        70        80        90       100
            ....|....|....|....|....|....|....|....|....|....|...
hLiv14 LA   SGVPDRFSGSGSGTDFTLKISRVEAEDVGVYYCFQGSHVPYTFGGGTKVEIKR
hLiv14 LB   ..................................................
hLiv14 LC   ..................................................
hLiv14 LD   ..................................................
hLiv14 LE   ..................................................
hLiv14 LF   ..................................................
BR2-14a     ............................L.....................L....
CDRs        *                                 *********
```

FIGURE 1

| | BR2-14a | hLIV-14 |
|---|---|---|
| Kd (nM) | 5.8 | 2.9 |
| Kd (ug/mL) | 0.8 | 0.4 |

| | BR2-14a | hLIV-14 HBLB S239C | hLIV-14 HBLB WT |
|---|---|---|---|
| EC50 | 3.421 | 0.4195 | 0.6416 |

LIV-1 Expression in Hormone Refractory Metastatic Prostate Cancer (Sorted By Site)

| | LIV-1 | |
|---|---|---|
| | # | % |
| Total Number of Samples+ (intensity 1-4+) | 36/50 | 72 |
| Bone Mets | 15/25 | 60 |
| Soft Tissue Mets | 21/25 | 82 |

FIGURE 7

| | hLIV-14-1006 | hLIV-14-SEA-1006 | BR2-14a-1-1006 | hIgG-1006 | mIgG-1006 | hLIV-14-1269 | BR2-14a-1269 | hIgG-1269 | mIgG-1269 |
|---|---|---|---|---|---|---|---|---|---|
| IC50 ng/ml | 91 | 91 | 20 | >10 000 | 4786 | 195 | 20 | >10 000 | >10 000 |

| | IC50 (ng/mL) | Max Lysis |
|---|---|---|
| hLIV-14 SEA | 97.1 | 44% |
| hLIV-14 SEA vcMMAE | 49.9 | 26% |

| | IC50 (ng/mL) | Max Lysis |
|---|---|---|
| hLIV-14 SEA | 21.8 | 85% |
| hLIV-14 SEA vcMMAE | 17.0 | 80% |

Activity of Humanized LIV-14 ADC On PC3 (DSMZ) Prostate Carcinoma Tumors in Nude Female Mice

```
                    10        20        30        40        50
            ....|....|....|....|....|....|....|....|....|....|....|....
hLiv22 HA   QVQLVQSGAEVKKPGASVKVSCKASGYTFTDYYMHWVKQAPGQGLEWMGWIDPENGDTEY
hLiv22 HB   ............................KE..............................
hLiv22 HC   ............................................................
hLiv22 HD   ............................G...............................
hLiv22 HE   ............................LNIK................E...........
hLiv22 HF   ............................L.IE..............................
hLiv22 HG   ............................L.IE..............................
mLiv22 H    E...Q.....LVES.....L..T...LNIK.......E.E.E.....I.............
CDRs                                     *****                 ***********

            60        70        80        90       100       110
            |....|....|....|....|....|....|....|....|....|....|....|...
hLiv22 HA   GPKFQGRVTMTRDTSISTAYMELSRLRSDDTAVYYCARHNAMYGTWFAYWGQGTLVTVSS
hLiv22 HB   ................N...........................................
hLiv22 HC   ......KA...A...................................................
hLiv22 HD   ......................................TV......................
hLiv22 HE   ......KA...A....N...................TV......................
hLiv22 HF   ......................................V.......................
hLiv22 HG   ................N.....................V.......................
mLiv22 H    ......KA...A...SN...LQ..S.T.G.......TV......................A
CDRs        ******                                 ***********

hLiv22 HA
hLiv22 HB
hLiv22 HC
hLiv22 HD
hLiv22 HE
hLiv22 HF
hLiv22 HG
mLiv22 H
```

FIGURE 16A

```
                    10        20              30        40        50
            ....|....|....|....|....|.........|....|....|....|....|....|
hLiv22 LA   DVVMTQSPLSLPVTLGQPASISCRSSQSLLHSSGNTYLHWFQQRPGQSPRRLIYKISNRF
hLiv22 LB   ........................................Y.....................
hLiv22 LC   ........................................L.....................
hLiv22 LD   ......................................................M.......
hLiv22 LE   ......................................................P.......
hLiv22 LF   ........................................YL......KP...........
hLiv22 LG   ........................................Y........P...........
mLiv22 L    ..L...T......S..DQ......................YL......KP...........
CDRs                                 ***************              ******

                60        70        80        90        100
            ....|....|....|....|....|....|....|....|....|....|...
hLiv22 LA   SGVPDRFSGSGSGTDFTLKISRVEAEDVGVYYCFQGSHVPYTFGGGTKVEIKR
hLiv22 LB   ..................................................
hLiv22 LC   ..................................................
hLiv22 LD   ..................................................
hLiv22 LE   ..................................................
hLiv22 LF   ..................................................
hLiv22 LG   ..................................................
mLiv22 L    ............................L.L...................L....
CDRs        *                                *********
```

FIGURE 16B

LIV22 Back Mutations (round2)

| | L36 | L37 | L45 | L46 | # back mutations |
|---|---|---|---|---|---|
| LA | F | Q | R | R | 0 |
| LB | Y | Q | R | R | 1 |
| LC | F | L | R | R | 1 |
| LD | F | Q | K | R | 1 |
| LE | F | Q | R | P | 1 |
| LF | Y | L | K | P | 4 |

| | H27 | H28 | H29 | H30 | H48 | H66 | H67 | H71 | H76 | H93 | H94 | # back mutations |
|---|---|---|---|---|---|---|---|---|---|---|---|---|
| HA | Y | T | F | T | M | R | V | R | S | A | R | 0 |
| HB | Y | T | I | (E) | M | R | V | R | N | A | R | 3 |
| HC | Y | T | F | T | M | K | A | A | S | A | R | 3 |
| HD | L | T | F | T | M | R | V | R | S | T | V | 3 |
| HE | L | N | I | (E) | I | K | A | A | N | T | V | 11 |

Additional LIV22 Mutations (round3)

| | L36 | L37 | L45 | L46 | # back mutations |
|---|---|---|---|---|---|
| LF | Y | L | K | P | 4 |
| LF-1 | F | L | K | P | 3 |
| LF-2 | Y | Q | K | P | 3 |
| LF-3 | Y | L | R | P | 3 |
| LF-4 | Y | L | K | R | 3 |

| | H27 | H28 | H29 | H30 | H48 | H66 | H67 | H71 | H76 | H93 | H94 | # back mutations |
|---|---|---|---|---|---|---|---|---|---|---|---|---|
| HE | L | N | I | (E) | I | K | A | A | N | T | V | 11 |
| HE-1 | Y | N | I | (E) | I | K | A | A | N | T | V | 10 |
| HE-2 | L | T | I | (E) | I | K | A | A | N | T | V | 10 |
| HE-3 | L | N | F | (E) | I | K | A | A | N | T | V | 10 |
| HE-4 | L | N | I | T | I | K | A | A | N | T | V | 10 |
| HE-5 | L | N | I | (E) | M | K | A | A | N | T | V | 10 |
| HE-6 | L | N | I | (E) | I | R | A | A | N | T | V | 10 |
| HE-7 | L | N | I | (E) | I | K | V | A | N | T | V | 10 |
| HE-8 | L | N | I | (E) | I | K | A | R | N | T | V | 10 |
| HE-9 | L | N | I | (E) | I | K | A | A | S | T | V | 10 |
| HE10 | L | N | I | (E) | I | K | A | A | N | A | V | 10 |
| HE11 | L | N | I | (E) | I | K | A | A | N | T | R | 10 |

FIGURE 18

Additional LIV22 Back Mutations: LF

| | L38 | L37 | L46 | L48 | # back mutations |
|---|---|---|---|---|---|
| LF | Y | L | K | P | 4 |
| LF-1 | F | L | K | P | 3 |
| LF-2 | Y | Q | K | R | 3 |
| LF-3 | Y | L | R | R | 3 |
| LF-4 | Y | L | K | R | 3 |

residues to maintain antigen binding:

Y36 (Tyrosine) & P46 (Proline)

Additional hLIV22 Back Mutations: HE

| | H27 | H28 | H29 | H30 | H48 | H66 | H67 | H71 | H76 | H93 | H94 | # back mutations |
|---|---|---|---|---|---|---|---|---|---|---|---|---|
| HE | L | N | I | E | I | K | A | A | N | T | V | 11 |
| HE-1 | Y | N | I | E | I | K | A | A | N | T | V | 10 |
| HE-2 | L | T | I | E | I | K | A | A | N | T | V | 10 |
| HE-3 | L | N | F | E | I | K | A | A | N | T | V | 10 |
| HE-4 | L | N | I | T | I | K | A | A | N | T | V | 10 |
| HE-5 | L | N | I | E | M | K | A | A | N | T | V | 10 |
| HE-6 | L | N | I | E | I | R | A | A | N | T | V | 10 |
| HE-7 | L | N | I | E | I | K | V | A | N | T | V | 10 |
| HE-8 | L | N | I | E | I | K | A | R | N | T | V | 10 |
| HE-9 | L | N | I | E | I | K | A | A | S | T | V | 10 |
| HE-10 | L | N | I | E | I | K | A | A | N | A | V | 10 |
| HE-11 | L | N | I | E | I | K | A | A | N | T | R | 10 |

residues to maintain antigen binding:

L27 (Leucine)

I29 (Isoleucine)

E30 (Glutamic Acid)

N76 (Asparagine)

V94 (Valine)

| | # Back mutations | EC50 (ug/mL) |
|---|---|---|
| HGLG | 7 | 0.5 |
| HGLF | 9 | 0.4 |
| HFLG | 6 | 0.8 |
| HFLF | 8 | 0.8 |

Apparent Kd (nM) of BR2-14a, BR2-22a, hLIV14 and hLIV14 for human and cyno LIV-1

| antigen | BR-14a | hLIV14 | BR-22a | hLIV22 |
|---|---|---|---|---|
| Human LIV1 | 12.5 | 4.3 | 1.2 | 1.2 |
| Cyno LIV1 | 14.0 | 2.1 | 4.2 | 1.3 |

Negative control: m2H12

EC50 table. Average from 2 experiments

| | EC50 (ng/ml) |
|---|---|
| hLIV22 - 1006 | 0.9 |
| h00 - 1006 | 4961 |

Cytotoxic Activity of hLIV22-mcMMAF
MCF-7 (ATCC) cells. 144 hour treatment

EC50 table. Average from 2 experiments

| -1269 ADC | EC50 (ng/ml) |
|---|---|
| hLIV22 | 0.7 |
| h00 | >10000 |

HUMANIZED ANTIBODIES TO LIV-1 AND USE OF SAME TO TREAT CANCER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[The present application] *This application is a reissue application of U.S. Pat. No. 9,228,026 B2 which issued from U.S. patent application Ser. No. 13/990,778, with the International Filing date of Dec. 6, 2011, which* is the U.S. National Stage of PCT/US2011/063612 filed Dec. 6, 2011, which is a nonprovisional and claims the benefit of *U.S. Provisional Application No.* 61/420,291, filed Dec. 6, 2010, and *U.S. Provisional Application No.* 61/446,990, filed Feb. 25, 2011, each incorporated by reference in its entirety for all purposes.

[This application includes an electronic sequence listing in a file named 433583SEQLIST.txt, created on Jan. 20, 2015, and having a size of 98 kilobytes. The information in this file is hereby incorporated by reference.]

*SUBMISSION OF SEQUENCE LISTING ON ASCII TEXT FILE*

*The content of the following submission on ASCII text file is incorporated herein by reference in its entirety: a computer readable form (CRF) of the Sequence Listing (file name: 761682000530seqlist.txt, date recorded: Dec. 26, 2017, size: 99 KB).*

BACKGROUND

LIV-1 is a member of the LZT (LIV-1-ZIP Zinc Transporters) subfamily of zinc transporter proteins. Taylor et al., Biochim. Biophys. Acta 1611:16-30 (2003). Computer analysis of the LIV-1 protein reveals a potential metalloprotease motif, fitting the consensus sequence for the catalytic zinc-binding site motif of the zinc metalloprotease. LIV-1 mRNA is primarily expressed in breast, prostate, pituitary gland and brain tissue.

The LIV-1 protein has also been implicated in certain cancerous conditions, e.g. breast cancer and prostate cancer. The detection of LIV-1 is associated with estrogen receptor-positive breast cancer, McClelland et al., Br. J. Cancer 77:1653-1656 (1998), and the metastatic spread of these cancers to the regional lymph nodes. Manning et al., Eur. J. Cancer 30A: 675-678 (1994).

SUMMARY OF THE CLAIMED INVENTION

The invention provides a humanized antibody comprising a mature heavy chain variable region having an amino acid sequence at least 90% identical to SEQ ID NO:53 provided that position H27 is occupied by L, position H29 is occupied by I, H30 by E and H94 by V and a mature light chain variable region at least 90% identical to SEQ ID NO:60 provided position L36 is occupied by Y and position L46 by P. Optionally, the humanized antibody comprises three CDRs of SEQ ID NO:53 and three CDRs of SEQ ID NO:60.

Those CDRs are shown in FIG. 16. Optionally, position H76 is occupied by N. Optionally, the humanized comprises a mature heavy chain variable region having an amino acid sequence at least 95% identical to SEQ ID NO:53 and a mature light chain variable region at least 95% identical to SEQ ID NO:60. Optionally, the mature heavy chain variable region is fused to a heavy chain constant region and the mature light chain constant region is fused to a light chain constant region. Optionally, the heavy chain constant region is a mutant form of natural human constant region which has reduced binding to an Fcgamma receptor relative to the natural human constant region. Optionally, the heavy chain constant region is of IgG1 isotype. Optionally, the heavy chain constant region has an amino acid sequence comprising SEQ ID NO:44 and the light chain constant region has an amino acid sequence comprising SEQ ID NO:42. Optionally, the heavy chain constant region has an amino acid sequence comprising SEQ ID NO:46 (S239C) and the light chain constant region has an amino acid sequence comprising SEQ ID NO:42. In some such humanized antibodies, any differences in CDRs of the mature heavy chain variable region and mature light variable region from SEQ ID NOS. 52 and 60 respectively reside in positions H60-H65. In some such humanized antibodies, the mature heavy chain variable region has an amino acid sequence designated SEQ ID NO:52 or 53 and the mature light chain variable region has an amino acid sequence designated SEQ ID NO: 59 or 60. In some such humanized antibodies, the mature heavy chain variable region has an amino acid sequence designated SEQ ID NO:53 and the mature light chain variable region has an amino acid sequence designated SEQ ID NO:60. Some such humanized antibodies are conjugated to a cytotoxic or cytostatic agent. Some such humanized antibodies have an association constant for human or cynomolgus monkey LIV-1 of 0.5 to $2\times10^8$ $M^{-1}$.

The invention also provides a humanized antibody comprising a mature heavy chain variable region comprising the three Kabat CDRs of SEQ ID NO:52, wherein position H27 is occupied by L, position H29 is occupied by I, H30 by E, H76 by N, and H94 by V and a mature light chain variable region comprising the three Kabat CDRs of SEQ ID NO:60 provided position L36 is occupied by Y and position L46 by P.

The invention also provides a nucleic acid encoding a mature heavy chain variable region and/or a mature light chain variable region of any of the above defined humanized antibodies.

The invention further provides a method of treating a patient having or at risk of cancer, comprising administering to the patient an effective regime of any of the above defined humanized antibodies. The cancer can be for example a breast cancer, cervical cancer, melanoma, or a prostate cancer.

The invention further provides a pharmaceutical composition comprising a humanized antibody as defined above.

The invention further provides methods of treating a subject afflicted with a melanoma that expresses the LIV-1 protein by administering to the subject a LIV-1 specific antibody or a LIV-1 antibody drug conjugate, in an amount sufficient to inhibit growth of the melanoma cancer cells.

The invention further provides methods of treating a subject afflicted with a cervical cancer that expresses the LIV-1 protein by administering to the subject a LIV-1 specific antibody or a LIV-1 antibody drug conjugate, in an amount sufficient to inhibit growth of the cervical cancer cells.

The invention further provides a humanized antibody comprising a mature heavy chain variable region having an amino acid sequence at least 90% identical to HB (SEQ ID NO:10) and a mature light chain variable region at least 90% identical to LB (SEQ ID NO:5). Optionally, the antibody comprises a mature heavy chain variable region having an amino acid sequence at least 95% identical to HB and a mature light chain variable region at least 95% identical to LB. Optionally, in any such antibody, positions H29, H30 and H76 are occupied by I, E and N, and L36 is occupied by Y. Optionally, any difference in the variable region frameworks of the mature heavy chain variable region and SEQ ID NO:10 is/are selected from the group consisting of H27 occupied by F, H28 occupied by N, H48 occupied by I, H66 occupied by K, H67 occupied by A, H71 occupied by A, H76 occupied by N, H93 occupied by N, H94 occupied by V, L37 occupied by L, L39 occupied by K, L45 occupied by K, and L46 occupied by L. Optionally, the 3 CDRs of the mature heavy chain variable region are those of SEQ ID NO: 10 and the 3 CDRs of the mature light chain variable region are those of SEQ ID NO:15. The CDRs are shown in FIG. 1. Optionally, the mature heavy chain variable region is fused to a heavy chain constant region and the mature light chain constant region is fused to a light chain constant region. Optionally, the heavy chain constant region is a mutant form of natural human constant region which has reached binding to an Fegamma receptor relative to the natural human constant region. Optionally, the heavy chain constant region is of IgG1 isotype. Optionally, the heavy chain constant region has an amino acid sequence comprising SEQ ID NO:6 and the light chain constant region has an amino acid sequence comprising SEQ ID NO:4. Optionally, the heavy chain constant region has an amino acid sequence comprising SEQ ID NO:8 (S239C) and the light chain constant region has an amino acid sequence comprising SEQ ID NO:4. Optionally, any differences in CDRs of the mature heavy chain variable region and mature light variable region from SEQ ID NOS. 10 and 15 respectively reside in positions H60-H65. Optionally, the mature heavy chain variable region has an amino acid sequence comprising SEQ ID NO:10 and the mature light chain variable region has an amino acid sequence comprising SEQ ID NO:15. Optionally, the antibody is conjugated to a cytotoxic or cytostatic agent. Preferred humanized antibodies having greater affinity for LIV-1 than the antibody BR2-14a. In another embodiment, the humanized antibody has an association constant for human or cynomolgus monkey LIV-1 of 0.5 to $2\times10^{8}$ $M^{-1}$.

The invention further provides a humanized antibody comprising a mature heavy chain variable region comprising the 3 CDRs of SEQ ID NO:10 and wherein positions H29, H30 and H76 are occupied by I, E and N respectively, and a mature light chain variable region comprising the 3 CDRs of SEQ ID NO:15, and wherein position L36 is occupied by Y.

The invention further provides a nucleic acid encoding a mature heavy chain variable region and/or a mature light chain variable region of any of the humanized antibodies described above.

The invention further provides a method of treating a patient having or at risk of cancer, comprising administering to the patient an effective regime of a humanized antibody as described above. Optionally, the cancer is breast cancer, cervical cancer, melanoma, or a prostate cancer.

The invention further provides a pharmaceutical composition comprising a humanized antibody as described above.

The invention further provides a method of treating a patient having or at risk of triple negative breast cancer, comprising administering to the patient an effective regime of an antibody that specifically binds to LIV-1. Optionally, in such methods, the antibody is conjugated to a cytotoxic or cytostatic agent.

BRIEF DESCRIPTION OF THE FIGURES

FIG. 1 shows an alignment of the amino acid sequences of humanized LIV-1 heavy chain variable regions for hLIV-1 HA (SEQ ID NO:9), hLIV-1 HB (SEQ ID NO:10), hLIV-1 HC (SEQ ID NO:11), hLIV-1 HD (SEQ ID NO:12), and hLIV-1 HE (SEQ ID NO:13) with the heavy chain variable region of the parental murine mAb (referred to as BR2-14a) (SEQ ID NO:86) (upper two panels). FIG. 1 further shows an alignment of the amino acid sequences of humanized light chain variable regions for hLIV-1 LA (SEQ ID NO:14), hLIV-1 LB (SEQ ID NO:15), hLIV-1 LC (SEQ ID NO:16), hLIV-1 LD (SEQ ID NO:17), hLIV-1 LE (SEQ ID NO:18), and hLIV-1 LF (SEQ ID NO:19) with the light chain variable region of the parental murine mAb (referred to as BR2-14a) (SEQ ID NO:87) (lower two panels).

FIG. 7 shows an analysis of LIV-1 protein expression by IHC on hormone-refractory metastatic prostate cancer patient samples.

FIGS. 16A and 16B show alignments of humanized heavy chain (FIG. 16A) and light chain (FIG. 16B) mature variable regions with those of the mouse BR2-22a. FIG. 16A shows an alignment of the amino acid sequences of humanized heavy chain variable regions for hLIV-22 HA (SEQ ID NO:47), hLIV-22 HB (SEQ ID NO:48), hLIV-22 HC (SEQ ID NO:49), hLIV-22 HD (SEQ ID NO:50), hLIV-22 HE (SEQ ID NO:51), hLIV-22 HF (SEQ ID NO:52), and hLIV-22 HG (SEQ ID NO:53) with the heavy chain variable region of the parental murine mAb (referred to as BR2-22a) (SEQ ID NO:88). FIG. 16B shows an alignment of the amino acid sequences of humanized light chain variable regions for hLIV-22 LA (SEQ ID NO:54), hLIV-22 LB (SEQ ID NO:55), hLIV-22 LC (SEQ ID NO:56). hLIV-22 LD (SEQ ID NO:57), hLIV-22 LE (SEQ ID NO:58), hLIV-22 LF (SEQ ID NO:59), and hLIV-22 LG (SEQ ID NO:60) with the light chain variable region of the parental murine mAb (referred to as BR2-22a) (SEQ ID NO:89).

FIG. 18 shows systemic variation of the HE and LF chains to test contribution of individual backmutations to antigen binding. Sites of potential somatic hypermutations are in parentheses. Mouse residues are underlined. The remaining residues are human germline residues.

DEFINITIONS

Figure 2:
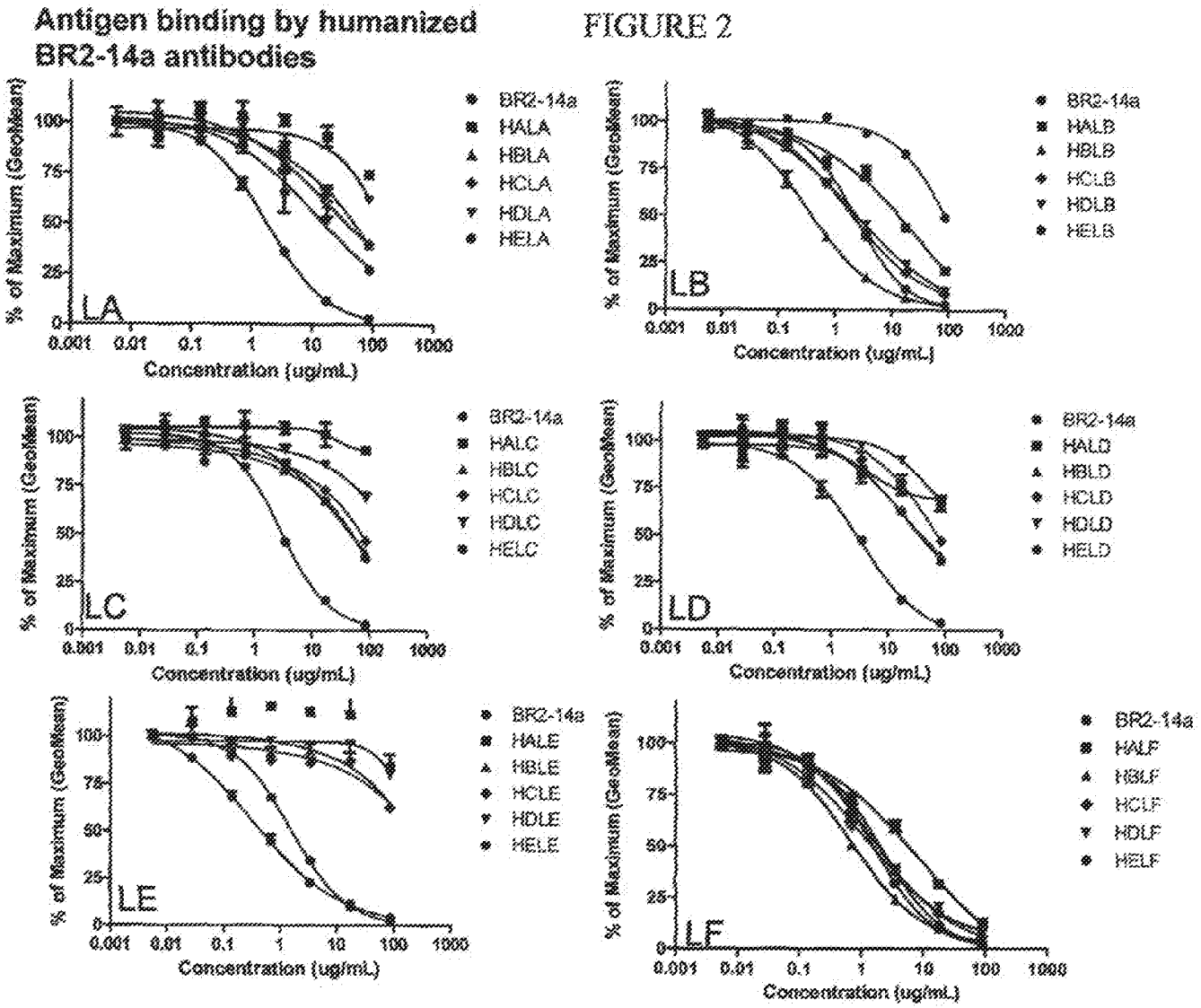
FIG. 2 shows the binding curves for the humanized LIV-1 mAbs and the parental murine antibody (referred to as BR2-14a).

Monoclonal antibodies are typically provided in isolated form. This means that an antibody is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Sometimes monoclonal antibodies are at least 60%, 70%, 80%, 90%, 95 or 99% w/w pure of interfering proteins and contaminants from production or purification.

Specific binding of a monoclonal antibody to its target antigen means an affinity of at least $10^6$, $10^7$, $10^8$, $10^9$, or $10^{10}$ $M^{-1}$. Specific binding is detachably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, antibody fragments compete with the intact antibody from which they were derived for specific binding to the target including separate heavy chains, light chains Fab, Fab', $F(ab')_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$-$V_H$-$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148: 1547-53 (1992)). The term "antibody" includes an antibody by itself (naked antibody) or an antibody conjugated to a cytotoxic or cytostatic drug.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90%, or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, len, ile; Group II (neutral hydrophilic side chains): cys, ser, thr; Group III (acidic side chains): asp, glu; Group IV (basic side chains): asn, gln, his, lys, arg: Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identifies are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

An antibody effector function refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the LIV-1 targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, nentrophils and eosinophils. Engagement of FcγR by IgG activates antibody-dependent cellular cytotoxicity (ADCC) or antibody-dependent cellular phagocytosis (ADCP), ADCC is mediated by $CD16^+$ effector cells through the secretion of membrane pore-forming proteins and proteases, while phagocytosis is medicate by $CD32^+$ and $CD64^+$ effector cells (see Fundamental Immunology, $4^{th}$ ed., Paul ed., Lippincott-Raven, N.Y., 1997, Chapters 3, 17 and 30; Uchida et al., 2004, J. Exp. Med. 199:1659-69; Akewanlop et al., 2001, Cancer Res. 61:4061-65; Watanabe et al., 1999, Breast Cancer Res. Treat 53:199-207). In addition to ADCC and ADCP, Fc regions of cell-bound antibodies can also activate the complement classical pathway to elicit complement-dependent cytotoxicity (CDC). Clq of the complement system binds to the Fc regions of antibodies when they are complexed with antigens. Binding of Clq to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see Immunobiology, $6^{th}$ ed., Janeway et al., Garland Science, N.Y., 2005, Chapter 2).

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component Clq which in turn activates the complement cascade leading to target cell death. Activation of complement may also result in deposition of complement components on the target cell surface that facilitate ADCC by binding complement receptors (e.g., CR3) on lenkocytes.

A "cytotoxic effect" refers to the depletion, elimination and/or the killing of a target cell. A "cytotoxic agent" refers to an agent that has a cytotoxic effect on a cell. Cytotoxic agents can be conjugated to an antibody or administration in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" means approved or approvable by a regulatory agency of the Federal or a state government or listed in the U.S. Pharmacopenia or other generally recognized pharmacopeia for use in animals, and more particularly in humans. The term "pharmaceutically compatible ingredient" refers to a pharmaceutically acceptable diluent, adjuvant, excipient, or vehicle with which an anti-LIV-1 antibody.

The phrase "pharmaceutically acceptable salt," refers to pharmaceutically acceptable organics or inorganic salts of an anti-LIV-1 antibody or conjugate thereof or agent administered with an anti-LIV-1 antibody. Exemplary salts includes sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, glyconate, glucuronate, saccharate, formate, benzoate, glutamate, methanesulfonate, ethanesulfonate, benzenesulfonate, p-toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise apparent from the context, the term "about" encompasses values within a standard deviation of a stated value.

DETAILED DESCRIPTION

I. General

The invention provides monoclonal antibodies that specifically bind to LIV-1.

The antibodies are useful for treatment and diagnoses of various cancers as well as detecting LIV-1.

II. Target Molecules

Unless otherwise indicated, LIV-1 means a human LIV-1. An exemplary human sequence is assigned Swiss Prot accession number Q13433. Q13433 is included herein as SEQ ID NO:83. Three variant isoforms and one polymorphism are known. A second version of the human LIV-1 protein, accession number AAA96258.2, is included herein as SEQ ID NO:84. Four extracellular domains are bounded by residues 29-325, 377-423, 679-686 and 746-755 of Q13433 respectively.

Unless otherwise apparent from the context reference LIV-1 means at least an extracellular domain of the protein and usually the complete protein other than a cleavable signal peptide (amino acids 1-28 of Q13433).

III. Antibodies of the Invention

A. Binding Specificity and Functional Properties

Figure 22:
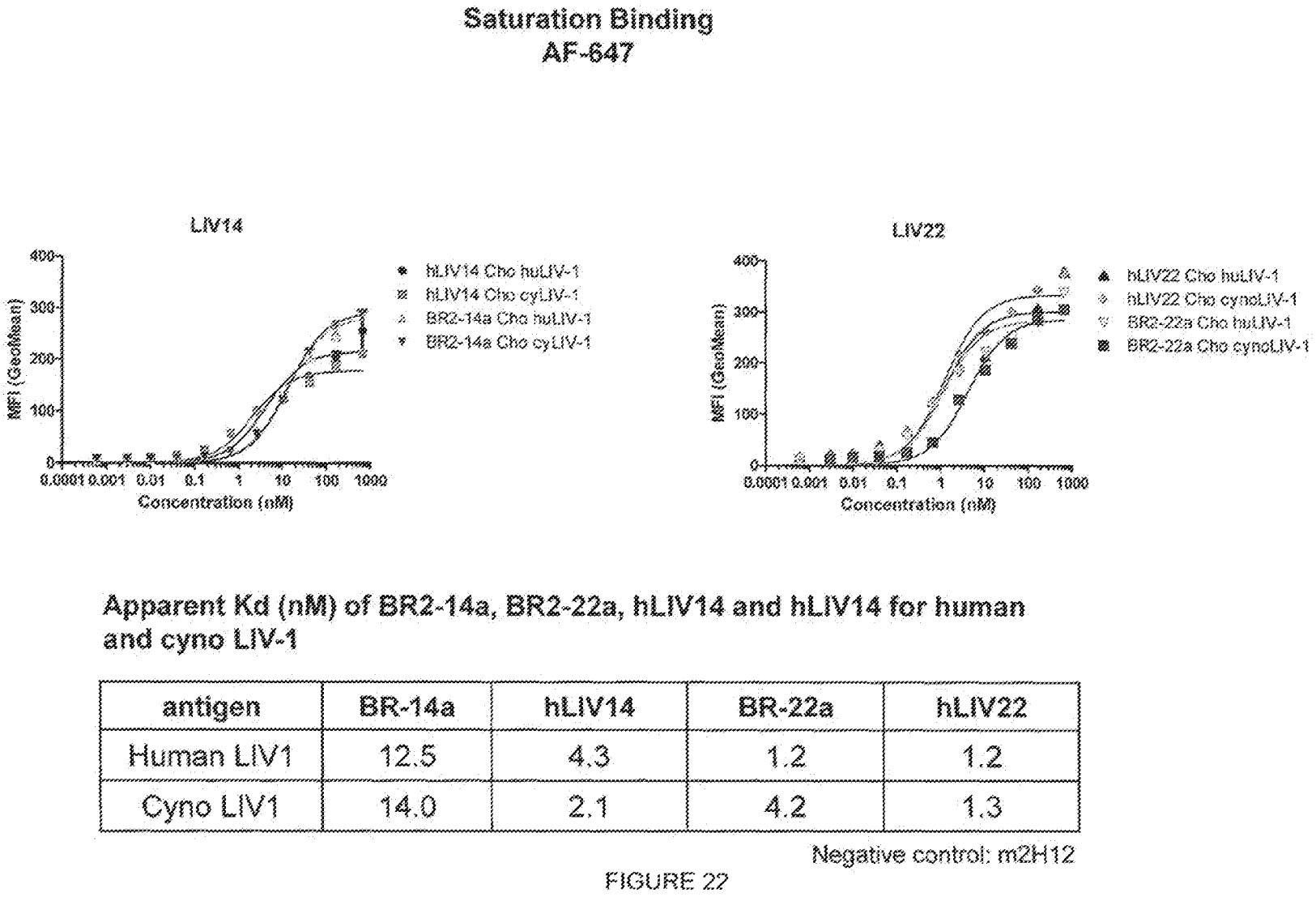
FIG. 22 shows saturation binding of humanized LIV 14 antibody and humanized LIV22 antibody on human and cynomolgus LIV-1 expressed from CHO cells.

The invention provides humanized antibodies derived from two mouse antibodies, BR-2-14and BR2-22a. Unless specifically indicated otherwise, the present disclosures relate to both antibodies. The two mouse antibodies show 94% and 91% sequence identity to one another in the nature heavy and light chain variable regions. The two antibodies bind to the same or overlapping epitopes on human LIV-1. However, the BR2-22a antibody has about ten-fold higher affinity for human LIV-1 and about 3-fold higher affinity for cynomolgus monkey LIV-1 than BR2-14a as shown in FIG. 22.

The affinity of humanized forms of the mouse BR2-14a antibody (i.e., Ka) is preferably within a factor of five or a factor of two of that of the mouse antibody BR2-14a for human LIV-1. Humanized BR2-14a antibodies specifically bind to human LIV-1 in native form and/or recombinantly expressed from CHO cells as does the mouse antibody from which they were derived. Preferred humanized BR2-14a antibodies have an affinity the same as or greater than (i.e., greater than beyond margin of error in measurement) that of BR2-14a for human LIV-1 (e.g., 1.1-5 fold, 1.1 to 3 fold, 1.5 to 3-fold, 1.7 to 2.3-fold or 1.7-2.1-fold the affinity or about twice the affinity of BR2-14a). Preferred humanized BR2-14a antibodies bind to the same epitope and/or compete with BR2-14a for binding to human LIV-1. Preferred humanized BR2-14a antibodies also bind to the cyno-homolog of LIV-1 thus permitting preclinical in nonhuman primates.

The affinity of humanized forms of the mouse BR2-22a antibody (i.e., Ka) for human LIV-1, natively expressed or expressed from CHO cells, is preferably within a factor of five or a factor of two of that of the mouse antibody BR2-22. Some humanized BR2-22a antibodies have an association constant that is essentially the same as that of BR2-22a (i.e., within experimental error). Some humanized BR2-22a antibodies have an association constant within a range of 0.5 to 1 or 0.5-1.5 that of the association constant of the BR2-22a antibody. Preferred humanized BR2-22a antibodies have an association constant greater than $5\times10^8$ $M^{-1}$, or in a range of 0.5 to $2\times10^9$ $M^{-1}$ or about $0.8\times10^9$ $M^{-1}$ (+/− error in measurement) for human LIV-1 expressed from CHO cells. Here as elsewhere in this application, affinities can be measured in accordance with the methods of the Examples. Preferred humanized BR2-22a antibodies bind to the same epitope and/or compete with BR2-22a for binding to human LIV-1. Humanized BR2-22a antibodies bind to the cyno-homolog of LIV-1 as well as human LIV-1. Preferred humanized BR2-22a antibodies bind with essentially the same association constant to human and cynomolgus monkey LIV-1 both expressed from CHO cells (within experimental error) thus permitting and increasing the predictive accuracy of preclinical testing in nonhuman primates.

Preferred antibodies (both humanized BR2-14a and humanized BR2-22a) inhibit cancer (e.g., growth of cells, metastasis and/or lethality to the organisms) as shown on cancerous cells propagating in culture, in an animal model or clinical trial. Animal models can be formed by implanting LIV-1-expressing human tumor cell lines into appropriate immunodeficient rodent strains, e.g., athymic nude mice or SCID mice. These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-LIV-1 antibodies or conjugated forms thereof as described in the Examples.

B. Humanized Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101, and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. A preferred acceptor sequence for the heavy chain is the germline $V_H$ exon $V_H$1-2 (also referred to in the literature as HV1-2) (Shin et al., 1991, EMBO J, 10:364-3645) and for the hinge region ($J_H$), exon $J_H$-6 (Mattila et al., 1995, Eur. J. Immunol. 25:2578-2582). For the light chain, a preferred acceptor sequence is exon VK2-30 (also referred to in the literature as KV2-30) and for the hinge region exon Jκ-4 (Hieter et al., 1982, J. Biol. Chem. 257:1516-1522). Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dABs, a humanized antibody comprises a humanized heavy chain and a humanized light chain. A CDR in a humanized antibody is substantially from a corresponding CDR in a non-human antibody when at least 60%, 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Certain amino acids from the human variable region framework residues can be selected for substitution based on their possible influence on CDR configuration and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g., is within about 6 Å of a CDR region); or
(4) medicates interaction between the heavy and light chains.

The invention provides humanized forms of the mouse BR2-14a antibody including five exemplified humanized heavy chain mature variable regions (HA-HE) and six exemplified humanized light chain mature variable regions (LA-LF). The permutations of these chains having the strongest binding (lowest BC50) and HBLB, HBLF, HCLB, HCLF, HDLB, HDLF, HELE and HELF. Of these permutations, HBLB (also know as hLIV14) is preferred because it has the strongest binding, about 2 fold stronger than the mouse donor antibody, and has the fewest back mutations (four).

The invention provides variants of the HBLB humanized antibody in which the humanized heavy chain mature variable region shows at least 90%, 95% or 99% identity to SEQ ID NO:10 and the humanized light chain mature variable region shows at least 90%, 95% or 99% sequence identity to SEQ ID NO:15. Preferably, in such antibodies some or all of the backmutations in HBLB are retained. In other words, at least 1, 2 or preferably all 3 of heavy chain positions H29, H30 and H76 are occupied by I and E and N, respectively. Likewise position L36 is preferably occupied by Y. The CDR regions of such humanized antibodies are preferably substantially identical to the CDR regions of HBLB, which are the same as those of the mouse donor antibody. The CDR regions can be defined by any conventional definition (e.g., Chothia) but are preferably as defined by Kabat. In one embodiment, the humanized antibody comprises a heavy chain comprising the 3 CDRs of SEQ ID NO:10 and variable region frameworks with a least 95% identity to the variable region frameworks of SEQ ID NO: 10. In another embodiment, the humanized antibody comprises a light chain comprising the 3 CDRs of SEQ ID NO:15 and variable region frameworks with at least 95% identity to variable region frameworks of SEQ ID NO:15. In a further embodiment, the humanized antibody comprises a heavy chain comprising the 3 CDRs of SEQ ID NO:10 and variable region frameworks with at least 95% identity to the variable region frameworks of SEQ ID NO:10, and a light chain comprising the 3 CDRs of SEQ ID NO:15, and variable region frameworks with at least 95% identity to the variable region frameworks of SEQ ID NO:15.

Insofar as humanized antibodies show any variation from the exemplified HBLB humanized antibody, one possibility for such additional variation is additional backmutations in the variable region frameworks. Any or all of the positions backmutated in other exemplified humanized heavy or light chain mature variable regions can also be made (i.e., 1, 2, 3, 4, 5, 6, 7, 8 or all 9 of H27 occupied by P, H28 occupied by N, H48 occupied by I, H66 occupied by K, H67 occupied by A, H71 occupied by A, H76 occupied by N, H93 occupied by N and H94 occupied by V in the heavy chain and 1, 2, 3, 4 or all 5 of L37 occupied by L, L39 occupied by K, L45 occupied by K, and L46 occupied by L in the light chain. However, such additional backmutations are not preferred because they in general do not improve affinity and introducing more mouse residues may give increased risk of immunogenicity.

Figure 21:
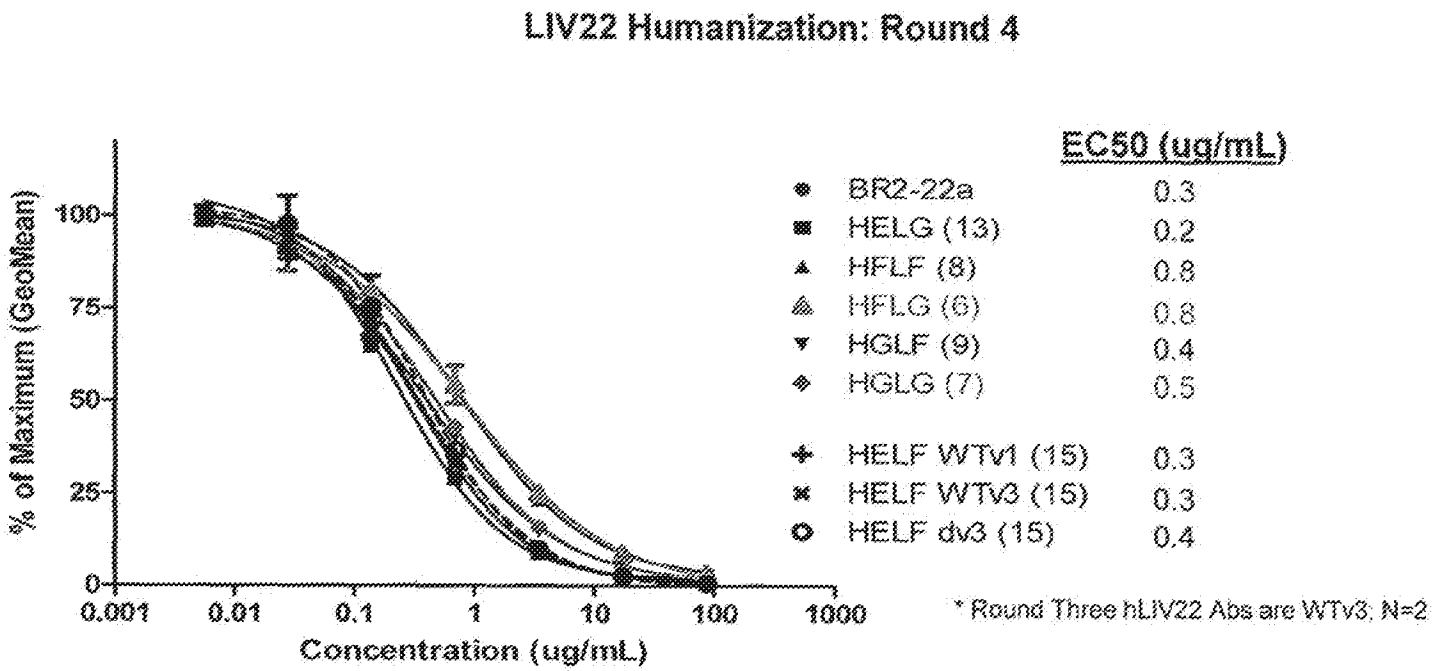
FIG. 21 shows competition binding of different permutations of HE, HF, HG and LF and LG.

The invention provides humanized forms of the mouse BR2-22a antibody including three exemplified humanized heavy chain mature variable regions (HE, HF and HG) and two exemplified humanized light chain (LF and LG) which can be combined in different permutations with adequate binding (see FIG. 21). Of these permutations, HGLG (also known as hLIV22) is preferred because it has the best combination of binding properties (essentially the same as the mouse BR2-22a antibody within experimental error) and fewest back mutations (seven).

The invention provides variants of the HGLG humanized antibody in which the humanized heavy chain mature variable region shows at least 90%, 95%, 98% or 99% identity to SEQ ID NO:53 and the humanized light chain mature variable region shows at least 90%, 95%, 98% or 99% sequence identity to SEQ ID NO:60. Preferably, in such antibodies some or all of the backmutations in HGLG are retained. In other words, at least 1, 2, 3, 4 or preferably all 5 of heavy chain positions H27, H29, H30, H76, and H94 are occupied by L, I, E, N and V (here, as elsewhere in this application Kabat numbering is used to describe positions in the nature variable heavy and light chain variable regions). Of these backmutations, H94 contributes the most to retention of binding affinity and H76 the least. Likewise positions L36 and L46 are preferably occupied by Y and P respectively. The CDR regions of such humanized antibodies are preferably substantially identical to the CDR regions of HGLG, which are the same as those of the mouse donor antibody. The CDR regions can be defined by any conventional definition (e.g., Chothia) but are preferably as defined by Kabat. In one embodiment, the humanized antibody comprises a heavy chain comprising the 3 CDRs of SEQ ID NO:53 and variable region frameworks with at least 95% identity to the variable region frameworks of SEQ ID NO:53. In another embodiment, the humanized antibody comprises a light chain comprising the 3 CDR's of SEQ ID NO:60 and variable region frameworks with at least 95% identity to the variable region frameworks of SEQ ID NO:60. In a further embodiment, the humanized antibody comprises a heavy chain comprising the 3 CDRs of SEQ ID NO:53 and variable region frameworks with at least 95% identity to the variable region frameworks of SEQ ID NO:53, and a light chain comprising the 3 CDRs of SEQ ID NO:60, and variable region frameworks with at lest 95% identity to the variable region frameworks of SEQ ID NO:60.

Insofar as humanized BR2-22a antibodies show any variation from the exemplified HGLG humanized antibody, one possibility for such additional variation is additional backmutations in the variable region frameworks. Any or all of the positions backmutated in other exemplified humanized heavy or light chain mature variable regions can also be made (i.e., 1, 2, 3, 4, 5 or all 6, of H28 occupied by N, H48 occupied by I, H66 occupied by K, H67 occupied by A, H71 occupied by A, H93 occupied by T in the heavy chain and 1 or, 2 of L37 occupied by L37 occupied by L, and L45 occupied by K. However, such additional backmutations are not preferred because they in general do not improve affinity and introducing more mouse residues may give increased risk of immunogenicity.

Another possible variation is to substitute certain residues in the CDRs of the mouse antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically; or as described in Gonzales et al., Mol. Immunol. 41: 863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflect a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. In a further variation, one or more residues in a CDR of a humanized BR2-22a antibody (which would otherwise be the same as the CDR of the mouse BR2-22a antibody) can be replaced by corresponding residues from a CDR from the mouse BR2-14a antibody (or vice versa). Positions for substitution within CDRs and amino acids to substitute can also be selected empirically.

Although not preferred other amino acid substitutions can be made, for example, in framework residues not in contact with the CDRs, or even some potential CDR-contact residues amino acids within the CDRs. Often the replacements made in the variant humanized sequences are conservative with respect to the replaced HBLB amino acids (in the case of humanized BR2-14a) or HGLG amino acids (in the case of humanized BR2-22). Preferably, replacements relative to HBLB or HGLG (whether or not conservative) have no substantial effect on the binding affinity or property of the humanized mAb, that is, its ability to bind human LIV-1 and inhibit growth of cancer cells.

Variants typically differ from the heavy and light chain mature variable region sequences of HBLB (hLIV14) or HGLG (hLIV22) by a small number (e.g., typically no more than 1, 2, 3,5 or 10 in either the light chain or heavy chain mature variable region, or both) of replacements, deletions or insertions.

C. Selection of Constant Region

The heavy and light chain variable regions of humanized antibodies can be linked to at least a portion of a human constant region. The choice of constant region depends, in part, whether antibody-dependence cell-mediated cytotoxicity, antibody dependent cellular phagocytosis and/or complement dependent cytotoxicity are desired. For example, human isotopes IgG1 and IgG3 have strong complement-dependent cytotoxicity, human isotype IgG2 week complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue is introduced at amino acid positions 234, 235, 237, 239, 267, 298, 299, 326, 330, or 332, preferably an S239C mutation in a human IgG1 isotype (US 200100158909). The presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. Nos. 6,624,821, 5,624,821.)

The in vivo half-life of an antibody can also impact on its effector functions. The half-life of an antibody can be increased or decreased to modify its therapeutic activities. FcRn is a receptor that is structurally similar to MHC Class 1 antigen that non-covalent associates with β2-microglobulin. FcRn regulates the catabolism of IgGs and their transcytosis across tissues (Ghetie and Ward, 2000, Annu. Rev. Immunol. 18:739-766; Ghetie and Ward, 2002, Immunol. Res. 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, Ann. Rev. Immunol. 18:739-766; Ghetie and Ward, 2002, Immunol. Res. 25:97-113). The region on human IgG 1 involved in FcRn binding has been mapped (Shields, et al., 2001, J. Biol. Chem. 276:6591-604). Alanine substitutions at positions Pro238, Thr256, Thr307, Gln311, Asp312, Gln380, Gla382, or Asn434 of human IgG1 enhance FcRn binding (Shields et al., 2001, J. Biol. Chem. 276:6591-604). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gln at position 250 and/or a Len at position 248. EU numbering is used for all position in the constant region.

Oligosaccharides covalently attached to the correspond Asn297 are involved in the ability of the Fc region of an IgG to bind FcγR (Lund et al., 1996, J. Immunol. 157:4963-69; Wright and Morrison, 1997, Trends Biotechnol. 15:26-31). Engineering of this glycoform on IgG can significantly improve IgG-mediated ADCC. Addition of bisecting N-acetylglucosamine modifications (Umana et al., 1999, Nat. Biotechnol. 17:176-180, Davies et al., 2001, Biotech. Bioeng. 74:288-94) to this glycoform or removal of fucose (Shields et al., 2002, J. Biol. Chem. 277:26733-40; Shinkawa et al., 2003, J. Biol. Chem. 278:6591-604; Niwa et al., 2004, Cancer Res. 64:2127-33) form this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., 2001, J. Biol. Chem. 276:6591-604). When compared to parental IgG1, a subset of these variants involving substitutions at Thr256/Ser298, Ser298/Glu333, Ser398/Lys344, or Ser298/Glu333/Lys334 to Ala demonstrate increased in both binding affinity toward FcγR and ADCC activity (Shields et al., 2001, J. Biol. Chem. 276:6591-604; Okazaki et al., 2004, J. Mol. Biol. 336:1239-49).

Complement fixation activity of antibodies (both Clq binding and CDC activity) can be improved by substitutions at Lys326 and Glu333 (Idusogie et al., 2001, J. Immunol. 166:2571-2575). The same substitutions on a human IgG2 back bone can convert an antibody isotype that binds poorly to Clq and is severely deficient in complement activation activity to one that can both bond Clq and mediate CDC (Idusogie et al., 2001, J. Immunol. 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., 1995, J. Immunol. 154:2226-36). also, substituting Ser444 located close to the carboxy-terminal of IgG1 heavy chain with Cys induced tail-to-tail dimerization of IgG1 with a 200-fold increase of CDC activity over monomeric IgG1 (Shopes et al., 1992, J. Immunol. 148:2918-22). In addition, a bispecific diabody construct with specificity for Clq also confers CDC activity (Kontermann et al., 1997, Nat. Biotech. 15:629-31).

Complement activity can be reduced by mutating at least one of the amino acid residues 318, 320, and 322 of the heavy chain to a residue having a different side chain, such as Ala. Other alkyl-substituted non-ionic residues, such as Gly, Ile, Leu, or Val, or such aromatic non-polar residues as Phe, Tyr, Trp and Pro in place of any one of the three residues also reduce or abolish Clq binding. Ser, Thr, Cys, and Met can be unused at residues 320 and 322, but not 318, to reduce or abolish Clq binding activity. Replacement of the 318 (Glu) residue by a polar residue may modify but not abolish Clq binding activity. Replacing residue 297 (Asn) with Ala results in removal of lytic activity but only slightly reduces (about three fold weaker) affinity for Clq. This alteration destroys the glycosylation site and the presence of carohydrate that is required for complement activation. Any other substitutions at this site also destroys the glycosylation site. The following mutations and any combination therefore also reduce Clq binding: D270A, K322A, P329A, and P311S (see WO 06/036291).

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcgamma receptor binding or increase binding to FcRN.

D. Expression of Recombinant Antibodies

Humanized antibodies are typically produced by recombinant expression. Recombinant polynucleotide constructs typically include an expression control sequence operably linked to the coding sequences of antibody chains, including naturally-associated of heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines (e.g., DG44), various COS cell lines. HeLa cells, HEK293 cells, L cells, and non-antibody-producing myelomas including Sp2/0 and NS0, Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Once expressed, antibodies can be purified according to standard procedures of the art, including HPLC purification, column chromatography, gel electrophoresis and the like (see generally, Scopes, Protein Purification (Springer-Verlag, NY, 1982)).

IV. Nucleic Acids

The invention further provides nucleic acids encoding any of the humanized heavy and light chains described above. Typically, the nucleic acids also encode a signal peptide fused to the mature heavy and light chains. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

V. Antibody Drug Conjugates

Anti-LIV-1 antibodies can be conjugated to cytotoxic or cyostatic moieties (including pharmaceutically compatible salts thereof) to form an antibody drug conjugate (ADC). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-LIV-1 antibody can be conjugated to a cytotoxic agent such as a chemotherapeutic agent, or a toxin (e.g., a cytostatic or cytocidal agent such as, e.g., abrin, ricin A, pseudomonas exotoxin, or diphtheria toxin).

An anti-LIV-1 antibody can be conjugated to a pro-drug converting enzyme. The pro-drug converting enzyme can be recombinantly fused to the antibody or chemically conjugated thereto using known methods. Exemplary pro-drug converting enzymes are carboxypeptides G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al., "Monoclonal Antibodies For Immunotargeting Of Drugs in Cancer Therapy," in Monoclonal Antibodies And Cancer Therapy (Reisfeld et al. eds., Alan R. Liss, Inc., 1985), Hellstrom et al., "Antibodies For Drug Delivery," in Controlled Drug Delivery (Robinson et al., eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624).

The therapeutic agent can be conjugated in a manner that reduces its activity unless it is cleaved off the antibody (e.g., by hydrolysis, by antibody degradation or by a cleaving agent). Such therapeutic agent is attached to the antibody with a cleavable linker that is sensitive to cleavage in the intracellular environment of the LIV-1-expressing cancer cell but is not substantially sensitive to the extracellular environment such that the conjugate is cleaved from the antibody when it is internalized by the LIV-1-expressing cancer cell (e.g., in the endosomal or, for example by virtue of pH sensitivity or protease sensitivity, in the lysosomal environment or in the caveolear environment).

Typically the ADC comprises a linker region between the therapeutic agent and the anti-LIV-1 antibody. As noted supra, typically, the linker is cleavable under intracellular conditions, such that the cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Typically, the peptidyl linker is at least two amino acids long or at least three amino acids long. Cleaving agents can include cathepsins B and D and plasmin (see, e.g., Dubowchik and Walker, 1999, Pharm. Therapeutics 83:67-123). Most typical are peptidyl linkers that are cleavable by enzymes that are present in LIV-1-expressing cells. For example, a peptidyl linker that is cleavable by the thiol-dependent protease cathepsin-B, which is highly expressed in cancerous tissue, can be used (e.g., a linker comprising a Phe-Leu or a Gly-Phe-Leu-Gly (SEQ ID NO:90) peptide). Other such linkers are described, e.g., in U.S. Pat. No. 6,214,345. In specific embodiments, the peptidyl linker cleavable by an intracellular protease comprises a Val-Cit linker or a Phe-Lys dipeptide (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

The cleavable linker can e pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929, Dubowchik and Walker, 1999, Pharm. Therapeutics 83:67-123; Neville et al., 1989, Biol. Chem. 264:14653-14661). Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In Immunoconjugates: Antibody Conjuates in Radioimagery and Therapy of Cancer (C. W. Vogel ed., Oxford U, Press 1987. See also U.S. Pat. No. 4,880,935.)

The linker can also be a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

The linker also can be a non-cleavable linker, such as an maleimido-alkylene- or maleimide-aryl linker that is directly attached to the therapeutic agent (e.g., a drug). An active drug-linker is released by degradation of the antibody.

Typically, the linker is not substantially sensitive to the extracellular environment meaning that no more than about 20%, typically no more than about 15%, more typically no more than about 10%, and even more typically no more than about 5%, no more than about 3%, or no more than about 1% of the linkers in a sample of the ADC is cleaved when the ADC present in an extracellular environment (e.g., in plasma). Whether a linker is not substantially sensitive to the extracellular environment can be determined, for example, by including independently with plasma both (a) the ADC (the "ADC sample") and (B) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

This linker can also promote cellular internalization. The linker can promote cellular internalization when conjugated to the therapeutic agent (i.e., in the milieu of the linker-therapeutic agent moiety of the ADC or ADC derivative as described herein). Alternatively, the linker can promote cellular internalization when conjugated to both the therapeutic agent and the anti-LIV-1 antibody (i.e., in the milieu of the ADC as described herein).

A variety of linkers that can be used with the present compositions are described in WO 2004-010957 and have the form $$-A_a-W_w—Y_y— \quad (1)$$

wherein:

-A- is a stretcher unit;

a is 0 or 1;

each —W— is independently an amino acid unit;

w is independently an integer ranging from 0 to 12;

—Y— is a spacer unit; and y is 0, 1 or 2.

Representative stretcher units are depicted within the square brackets of Formulas (Ia) and (Ib: see infra), wherein A-, —W—, —Y—, -D, w and y are as defined above and $R^1$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_8$-$C_{10}$ alkylene, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene, —$(CH_2CH_2O)_2$—, and —$(CH_2CH_2O)_2$—$CH_2$—; and r is an integer ranging from 1-10. Ab is antibody.

(Ia)

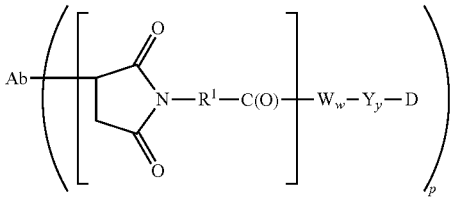

(Ib)

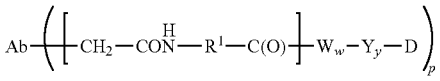

The drug loading is represented by p, the number of drug-linker molecules per antibody. Depending on the context, p can represent the average number of drug-linker molecules per antibody, also referred to the average drug loading, P ranges from 1 to 20 and is preferably from 1 to 8. In some preferred embodiments, when p represents the average drug loading, p ranges from about 2 to about 5. In some embodiments, p is about 2, about 3, about 4, or about 5. The average number of drugs per antibody in a preparation may be characterized by conventional means such as mass spectroscopy, ELISA assay, and HPLC.

The Amino Acid unit (—W—), if present, links the Stretcher unit (-A-) to the Spacer unit (—Y—) if the Spacer unit is present, and links the Stretcher unit to the cytotoxic or cytostatic agent (Drug unit; D) if the spacer unit is absent.

If present, —$W_w$— is preferably a dipeptide, tripeptide, tetrapeptide, pentapeptide, hexapeptide, heptapeptide, octapeptide, nonapeptide, decapeptide, undecapeptide or dodecapeptide unit.

The Spacer unit (—Y—), when present, links an Amino Acid unit to the Drug unit. Spacer units are of two general types: self-immolative and non self-immolative. A non self-immolative spacer unit is one in which part or all of the Spacer unit remains bound to the Drug unit after enzymatic cleavage of an amino acid unit from the anti-LIV-1 antibody-linker-drug conjugate or the drug-linker compound. Examples of a non self-immolative Spacer unit include a (glycine-glycine) spacer unit and a glycine spacer unit. When an anti-LIV-1 antibody-linker-drug conjugate containing a glycine-glycine spacer unit or a glycine spacer unit undergoes enzymatic cleavage via a tumor-cell associated-protease, a cancer-cell-associated protease or a lymphocyte-associated protease, a glycine-glycine-drug moiety or a glycine-drug moiety is cleaved from Ab-$A_a$-$W_w$,—. To liberate the drug, an independent hydrolysis reaction should take place within the target cell to cleave the glycine-drug unit bond.

Alternatively, an anti-LIV-1 antibody drug conjugate containing a self-immolative spacer unit can release the drug (D) without the need for a separate hydrolysis step. In some of these embodiments, —Y— is a p-aminobenzyl alcohol (PAB) unit that is linked to —$W_w$— via the nitrogen atom of the PAB group, and connected directly to -D via a carbonate, carbamate or ether group. Other examples of self-immolative spacers include aromatic compounds that are electronically equivalent to the PAB group such as 2-aminoimidazol-5-methanol derivatives (see Hay et al., 1999, Bioorg. Med. Chem. Lett. 9:2237 for examples) and ortho or para-aminobenzylacetals. Spacers can be used that undergo facile cyclization upon amide bond hydrolysis, such as substituted and unsubstituted 4-aminobutyric acid amides (Rodrigues et al., 1995, Chemistry Biology 2:223), appropriately substituted bicyclo[2.2.1] and bicyclo[2.2.2] ring systems (Storm et al., 1972, J. Amer. Chem. Soc. 94:5815) and 2-aminophenylpropionic acid amides (Amsberry et al., 1990, J. Org. Chem. 55:5867). Elimination of amine-containing drugs that are substituted at the α-position of glycine (Kingsbury, et al., 1984, J. Med. Chem. 27:1447) are also examples of self-immolative spacer strategies that can be applied to the anti-LIV-1 antibody-linker-drug conjugates. Alternatively, the spacer unit is a branched bis(hydroxymethyl)styrene (BHMS) unit, which can be used to incorporate additional drugs.

Useful classes of cytotoxic agents to conjugate to anti-LIV-1 antibodies include, for example, antitubulin agents. DNA minor groove binding agents, DNA replication inhibitors, chemotherapy sensitizers, or the like. Other exemplary classes of cytotoxic agents include anthracyclines, auristatins, camptothecins, duocarmycins, etoposides, maytansinoids and vinca alkaloids. Some exemplary cytotoxic agents include auristatins (e.g., auristatin E, AFP, MMAF, MMAE), DNA minor groove binders (e.g., enediynes and lexitropsins), duocarmycins, taxanes (e.g., paclitaxel and docetaxel), vinca alkaloids, doxorubicin, morpholino-doxorubicin and cyano-morpholino-doxorubicin.

The cytotoxic agent can be a chemotherapeutic such as, for example, doxorubicin, paclitaxel, melphalan, vinca alkaloids, methotrexate, mitomycin C or etoposide. The agent can also be a CC-1065 analogue, calicheamicin, maytansine, an analogue of dolastatin 10, rhizoxin, or palytoxin.

The cytotoxic agent can also be an auristatin. The auristatin can be an auristatin E derivative is, e.g., an ester formed between auristatin E and a keto acid. For example, auristatin E can be reacted with paraacetyl benzoic acid or benzoylvaleric acid to produce AFB and AEVB, respectively. Other typical auristatins include AFP, MMAF, and MMAE. The synthesis and structure of various auristatins are described in, for example, US 2005-0238649 and US2006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin).

The cytotoxic or cytostatic agent can be an anti-rubulin agent. Examples of anti-tubulin agents include taxanes (e.g., Taxol® (paclitaxel), Taxotere® (docetaxel)), T67 (Tularik), vinca alkyloids (e.g., vincristine, vinblastine, vindesine, and vinorelbine), and auristatins (e.g., auristatin E, AFP, MMAF, MMAE, AEB, AEVB). (Exemplary auristatins are shown below in formulae III-XIII. Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and elemtherobin.

(III)

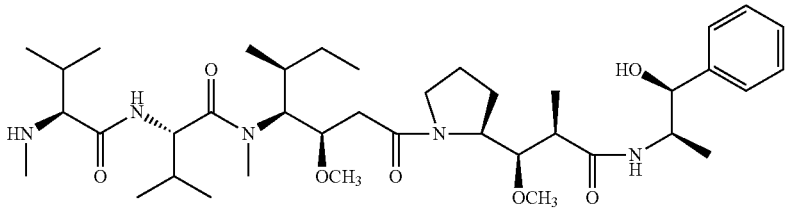

(IV)

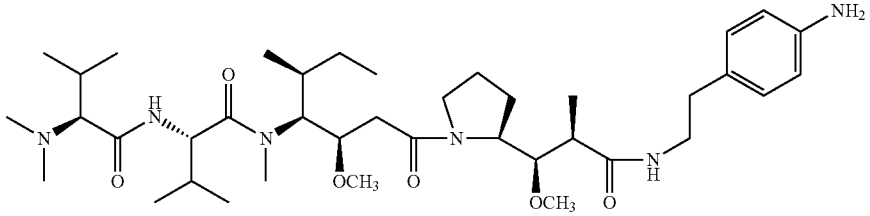

(V)

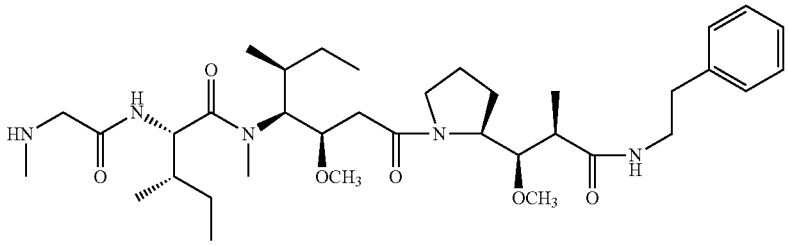

(VI)

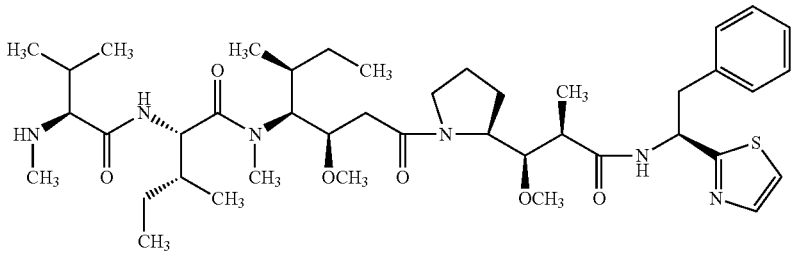

(VII)

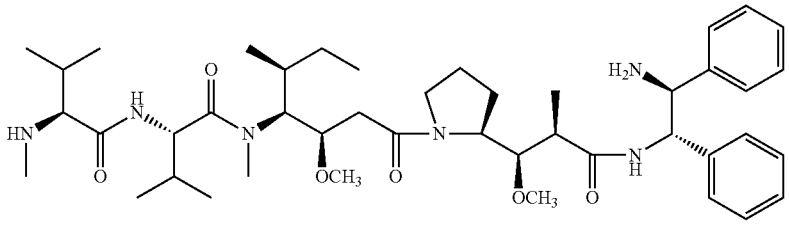

(VIII)

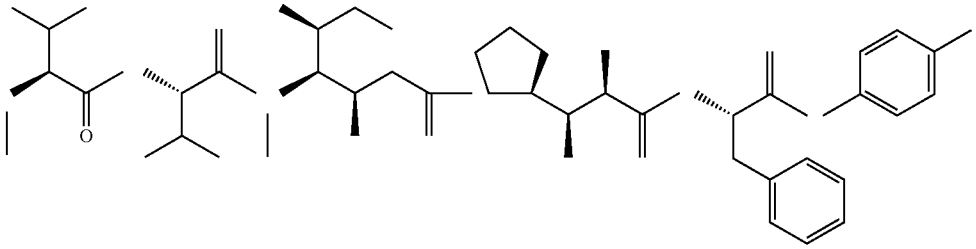

-continued
(IX)
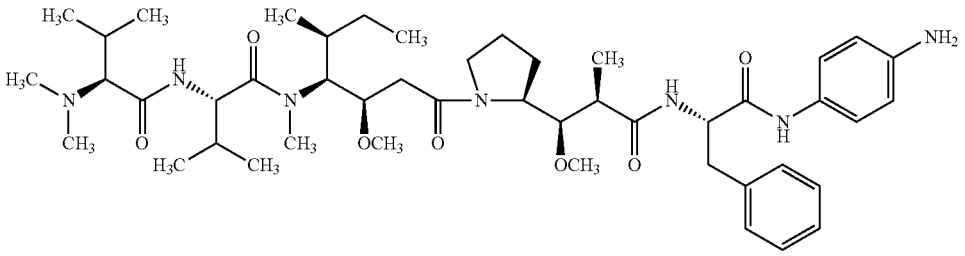
(X)
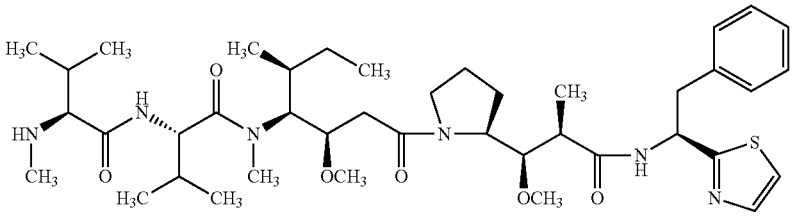
(XI)
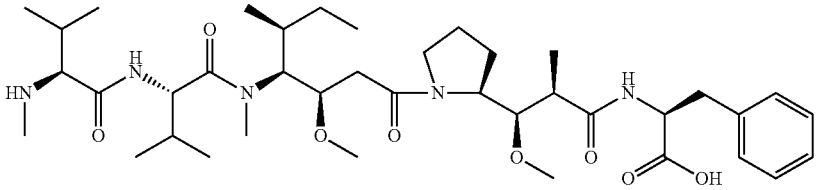
(XII)
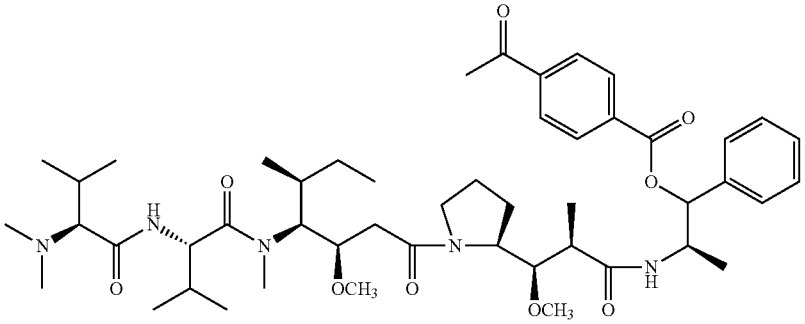
(XIII)
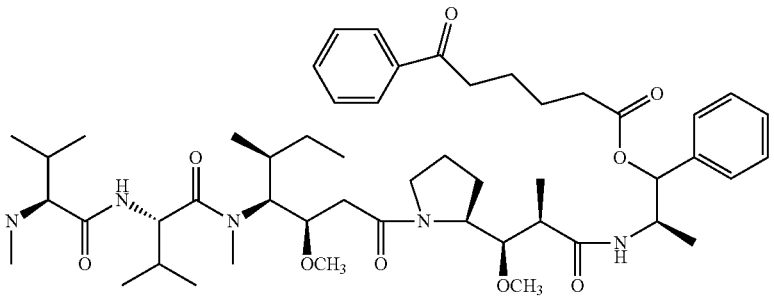
The cytotoxic agent can be a maytanisinoid, another group of anti-tubulin agents. For example, the maytansinoid can be maytansine or a maytansine containing drug linker such as DM-1 or DM-4 (ImmunoGen, Inc.; see also Chari et al., 1992. Cancer Res. 52:127-131).

Exemplary antibody drug conjugates include vcMMAE and mcMMAF antibody drug conjugates as follows wherein p and Ab are as previously described herein:

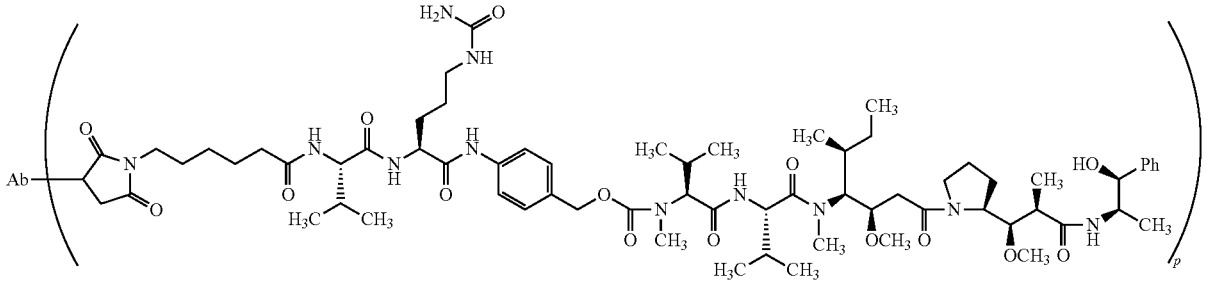

vcMMAE

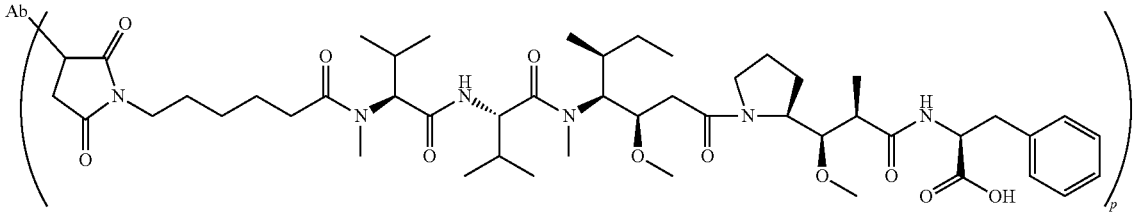

mcMMAF or a pharmaceutically acceptable salt thereof.

VI. Other Antibodies to LIV-1

As well as humanized forms of the BR2-14a and BR2-22a antibodies discussed above, other antibodies binding to an extracellular domain of LIV-1 can be used in some of the methods of the invention, particularly the treatment of triple negative breast cancers. A collection of mouse antibodies to LIV-1 is described in US20080175839. These antibodies include 1.1F10, 1.7A4, BR2-10b, BR2-11a, BR2-13a, BR2-14a, BR2-15a, BR2-16a, BR2-17a, BR2-18a, BR2-19a, BR2-20a, BR2-21a, BR2-22a, BR2-23a, BR2-24a, and BR2-25a, of which BR2-19a produced by the hybridoma ATCC Accession No. PTA-5706 or BR2-23a produced by the hybridoma ATCC Accession No. PTA-5707 in addition to BR2-14a and BR2-22a are preferred. Humanized, chimeric or veneered forms of these antibodies can be made by conventional methods summarized below.

Other antibodies to LIV-1 can be made de novo by immunizing with LIV-1 or one or more extracellular domains thereof. The production of other non-human monoclonal antibodies, e.g., murine, guinea pig, primate, rabbit or rat, against an immunogen can be performed by as described by Harlow & Lane, Antibodies, A Laboratory Manual (CSHP NY, 1988) (incorporated by reference for all purposes). Such an immunogen can be obtained from a natural source, by peptide synthesis or by recombinant expression.

Humanized, chimeric or veneered forms of non-human antibodies can be made. General methodology for producing humanized antibodies is described by Queen, U.S. Pat. Nos. 5,530,101 and 5,586,089; Winter, U.S. Pat. No. 5,225,539; Carter, U.S. Pat. No. 6,407,213; Adair, U.S. Pat. No. 5,859,205; and Foote, U.S. Pat. No. 6,881,557). A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence. A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

Human antibodies against LIV-1 can be provided by a variety of techniques described below. Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,886,397, 5,874,299, 5,814,318, 5,789,650, 5,770,429, 5,661,016, 5,633,425, 5,625,126, 5,569,825, 5,545,806, Nature 138, 1547-1553 (1994), Nature Biotechnology 14, 826 (1996), Kucherlapati, WO 91/10741 (1991) and phage display methods (see, e.g., Dower et al., WO 91/17271 and McCafferty et al., WO 92/01047, U.S. Pat. Nos. 5,877,218, 5,871,907. 5,858,657, 5,837,242, 5,733,743 and 5,565,332.

Any of the antibodies can be selected to have the same or overlapping epitope specificity as an exemplary antibody, such as the BR2-14a antibody, by a competitive binding assay or otherwise.

VII. Therapeutic Applications

The humanized antibodies of the invention, alone or as LIV-1 antibody drug conjugates thereof, can be used to treat cancer. Some such cancers show detectable levels of LIV-1measured at either the protein (e.g., by immunoassay using one of the exemplified antibodies ) or mRNA level. Some such cancers show elevated levels of LIV-1 relative to noncancerous tissue of the same type, preferably from the same patient. An exemplary level of LIV-1 on cancer cells amenable to treatments is 5000-150000 LIV-1 molecules per cell, although higher or lower levels can be treated. Optionally, a level of LIV-1 in a cancer is measured before performing treatment.

Examples of cancers associated with LIV-1 expression and amenable to treatment include breast cancer, prostate cancer, ovarian cancer, endometrial cancer, cervical, liver, gastric, kidney, and squamous cell carcinomas (e.g., bladder, head, neck and lung), skin cancers, e.g., melanoma, small lung cell carcinoma or lung carcinoid. The treatment can be applied to patients having primary or metastatic tumors of these kinds. The treatment can also be applied to patients who are refractory to conventional treatments (e.g., hormones, tamoxifen, herceptin), or who have replaced following a response to such treatments. The methods can also be used on triple negative breast cancers. A triple negative breast cancer is a term of art for a cancer lacking detectable estrogen and progesterone receptors and lacking overexpression of HER2/neu when stained with an antibody to any of these receptors, such as described in the examples. Staining can be performed relative to an irrelevant control antibody and lack of expression shown from a background level of straining the same or similar to that of the control within experimental error. Likewise lack of overexpression is shown by staining at the same or similar level within experimental error of noncancerous breast tissue, preferably obtained from the same patient. Alternatively or additionally, triple native breast cancers are characterized by lack of responsiveness to hormones interacting with these receptors, aggressive behavior and a distinct pattern of metastasis.

hLIV14 antibodies can be used to treat cancers that express LIV-1. In one embodiment, an hLIV14 antibody is used treat a subject with a LIV-1-expressing breast cancer. In another embodiment, an hLIV14 antibody is used treat a subject with a LIV-1-expressing prostate cancer. In another embodiment, an hLIV14 antibody is used treat a subject with a LIV-1-expressing melanoma. In another embodiment, an hLIV14 antibody is used treat a subject with a LIV-1-expressing ovarian cancer. In another embodiment, an hLIV14 antibody is used treat a subject with a LIV-1-expressing endometrial cancer. In another embodiment, an hLIV14 antibody is used treat a subject with a LIV-1-expressing cervical cancer. In another embodiment, an hLIV14 antibody is used treat a subject with a LIV-1-expressing liver cancer. In another embodiment, an hLIV14 antibody is used treat a subject with a LIV-1-expressing gastric cancer. In another embodiment, an hLIV14 antibody is used treat a subject with a LIV-1-expressing kidney cancer. In another embodiment, an hLIV14 antibody is used treat a subject with a LIV-1-expressing squamous cell carcinomas (e.g., bladder, head, neck and lung cancer). In another embodiment, an hLIV14 antibody is used treat a subject with a LIV-1-expressing breast cancer. In another embodiment, an hLIV14 antibody is used treat a subject with a LIV-1-expressing skin cancer. In another embodiment, an hLIV14 antibody is used treat a subject with a LIV-1-expressing small lung cell carcinoma or lung carcinoid. hLIV22 antibodies can be used to treat cancers that express LIV-1. In one embodiment, an hLIV22 antibody is used treat a subject with a LIV-1-expressing breast cancer. In another embodiment, an hLIV22 antibody is used treat a subject with a LIV-1-expressing prostate cancer. In another embodiment, an hLIV22 antibody is used treat a subject with a LIV-1-expressing melanoma. In another embodiment, an hLIV22 antibody is used treat a subject with a LIV-1-expressing ovarian cancer. In another embodiment, an hLIV22 antibody is used treat a subject with a LIV-1-expressing endometrial cancer. In another embodiment, an hLIV22 antibody is used treat a subject with a LIV-1-expressing cervical cancer. In another embodiment, an hLIV22 antibody is used treat a subject with a LIV-1-expressing liver cancer. In another embodiment, an hLIV22 antibody is used treat a subject with a LIV-1-expressing gastric cancer. In another embodiment, an hLIV22 antibody is used treat a subject with a LIV-1-expressing kidney cancer. In another embodiment, an hLIV22 antibody is used treat a subject with a LIV-1-expressing squamous cell carcinomas (e.g., bladder, head, neck, and lung cancer). In another embodiment, an hLIV22 antibody is used treat a subject with a LIV-1-expressing breast cancer. In another embodiment, an hLIV22 antibody is used treat a subject with a LIV-1-expressing skin cancer. In another embodiment, an hLIV22 antibody is used treat a subject with a LIV-1-expressing small lung cell carcinoma or lung carcinoid. This application provides the first disclosure that LIV-1 protein is expressed on the surface of the melanoma cells. Thus, antibodies that bind to LIV-1 can be used to treat patients that are afflicted with melanomas that express LIV-1. Such antibodies include antibodies disclosed herein, e.g., hLIV14 and hLIV22, but are not limited to the antibodies disclosed herein.

Humanized antibodies, alone or as conjugates thereof, are administered in an effective regime meaning a dosage, route of administration and frequency of administration that delays the onset, reduces the severity, inhibits further deterioration, and/or ameliorates at least one sign or symptom of cancer. If a patient is already suffering from cancer, the regime can be referred to as a therapeutically effective regime. If the patient is at elevated risk of the cancer relative to the general population but is not yet experiencing symptoms, the regime can be referred to as a prophylactically effective regime. In some instances, therapeutic or prophylactic efficiency can be observed in an individual patient relative to historical controls or past experiences in the same patient. In other instances, therapeutic or prophylactic efficacy can be demonstrated in a preclinical or clinical trial in a population of treated patients relative to a control population of untreated patients.

Exemplary dosages for a monoclonal antibody are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kgl, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kb. Exemplary dosages for a monoclonal antibody or antibody drug conjugates thereof are 1 mg/kg to 7.5 mg/kg, or 2 mg/kg to 7.5 mg/kg or 3 mg/kg to 7.5 mg/kg of the subject's body weight, or 0.1-20, or 0.5 mg/kg body weight (e.g., 0.5, 1, 2, 3, 4, 5, 6, 7, 8, 9 or 10 mg/kg) or 10-1500 or 200-1500 mg as a fixed dosage. In some methods, the patient is administered a dose of at least 1.5 mg/kg, at least 2 mg/kg or at least 3 mg/kb, administered once every three weeks or greater. The dosage depends on the frequency of administration, condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequency dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical composition can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution. Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 1-100 mg/mL such as 10 mg/ml.

Treatment with antibodies of the invention can be combined with chemotherapy, radiation, stem cell treatment, surgery other treatments effective against the disorder being treated. Useful classes of other agents that can be administered with humanized antibodies to LIV-1 include, for example, antibodies to other receptors expressed on cancerous cells, antitubulin agents (e.g., auristatins), DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with the humanized anti-LIV-1 antibody, optionally in combination with any of the other agents or regimes described above along or as an antibody drug conjugate, can increase the median progression-free survival or overall survival time of patients with tumors (e.g., breast, prostate, melanoma), especially when relapsed or refractory, by at least 30% or 40% but preferably 50%, 60% to 70% or even 100% or longer, compared to the same treatment (e.g., chemotherapy) but without an anti-LIV-1 antibody alone or as a conjugate. In addition or alternatively, treatment (e.g., standard chemotherapy) including the anti-LIV-1 antibody alone or as a conjugate can increase the complete response rate, partial response rate, or objective response rate (complete+partial) of patients with tumors by at least 30% or 40% but preferably 50%, 60% to 70% or even 100% compared to the same treatment (e.g., chemotherapy) but without the anti-LIV-1 antibody.

Typically, in a clinical trial (e.g., a phase II, phase II/III or phase III trial), the aforementioned increased in medium progression-free survival and/or response rate of the patients treated with standard therapy plus the humanized anti-LIV-1 antibody, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

VIII. Other Applications

The anti-LIV-1 humanized antibodies can be used for detecting LIV-1 in the context of clinical diagnosis or treatment or in research. Expression of LIV-1 on a cancer provides an indication that the cancer is amenable to treatment with the antibodies of the present invention. The antibodies can also be sold as research reagents for laboratory research in detecting cells bearing LIV-1 and their response to various stimuli. In such uses, monoclonal antibodies can be labeled with fluorescent molecules, spin-labeled molecules, enzymes or radioisotypes, and can be provided in the form of kit with all the necessary reagents to perform the assay for LIV-1. The antibodies described herein, BR2-14a, BR2-22a and humanized versions thereof, e.g., hLIV14 and hLIV22, can be used to detect LIV-1 protein expression and determine whether a cancer is amenable to treatment with LIV-1 ADCs. As an example, BR2-14a, BR2-22a and humanized versions thereof, e.g., hLIV14 and hLIV 22 can be used to detect LIV-1 expression on breast cancer cells, melanoma cells, cervical cancer cells, or prostate cancer cells. The antibodies can also be used to purify LIV-1, e.g., by affinity chromatography.

IX. Cynomolgus Monkey LIV-1

The invention further provides an amino acid sequence for LIV-1 (CY LIV-1) from cynomolgus monkeys at SEQ ID NO:85 with or without a signal peptide, which occupies approximately residues 1-28 of SEQ ID NO:85, as well as nucleic acids that encode that amino acid sequences. Variants differing by up to 1, 2, 3, 4, or 5 substitutions, deletions or insertions are also included provided CY variants do not include a natural human LIV-1 sequence. Analogous to human LIV-1, reference to CY-LIV-1 means at least one extracellular domain of the protein and usually the complete protein other than a cleavable signal peptide (amino acids 1-28). The invention further provides antibodies that specifically bind to SEQ ID NO:85 with or without specifically binding to human LIV-1 (i.e., binding to human LIV-1 at level of negative control irrelevant antibody). The invention further provides antibodies that preferentially bind CY-LIV-1 over human LIV-1 and vice versa. Preferential binding means an association higher beyond experimental error and preferably at least 2, 3 or 4 fold higher. The invention further provides antibodies that show the same binding profile to human and CY-LIV-1 within experimental error as any of the exemplified antibodies described below. The invention further provides methods of analyzing binding of an antibody to CY LIV-1. Such methods involve contacting an antibody with CY LIV-1, determining whether the antibody specifically binds to CY LIV-1 and optionally determining a measure of binding strength, such as an association constant.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The efective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

I. Humanization of BR2-14a

Materials

Cell lines described in the following examples were maintained in culture according to the conditions specified by the American Type Culture Collection (ATCC), the National Cancer Institute (NCI) or the Deutsche Sammlung von Mikroorganismen and Zellkulturen GmbH, Braunschweig, Germany (DMSZ). Cell culture reagents were obtained from Invitrogen Corp. (Carlsbad, Calif.) or other suppliers.

Methodologies:

Saturation Binding Assays $1\times10^5$ antigen expressing cells (either MCF7 cells (ATCC) expressing human LIV-1, a transfected CHO cell line expressing human LIV-1 or a transferred CHO cell line expressing cyno LIV-1) were aliquoted per well of a 96-well v-bottom plates. AlexaFluor-647 labeled murine LIV-1 mAb, e.g., BR2-14a, was added in concentrations ranging from 0.66 pM to 690 nM and incubated on ice for 30 minutes. Cells were pelleted and washed 3× with PBS/BSA. The cells were the pelleted and resuspended in 125 μL of PBS/BSA. Fluorescence was analyzed by flow cytometry, using percent of saturated fluorescent signal to determine percent bound and to subsequently calculate apparent Kd.

Competition Binding Assays $1\times10^5$ CHO cells expressing recombinant human LIV-1 in PBS/BSA were aliquoted on ice. The cells were incubated for 1 hours with 5 nM AlexaFluor-647 (AF) labeled parental murine LIV-1 mAb and increasing concentrations (from 0.038 nM to 600 nM) of unlabeled humanized LIV-1 mAb, combinations of humanized light chains LA-LF and humanized heavy chains HA-HE. Cells were pelleted and washed 3 times with PBS/BSA. The cells were pelleted and resuspended in 125 μL of PBS/BSA. Fluorescence was analyzed by flow cytometry, using percent of saturated fluorescent signal to determine percent labeled murine LIV-1 mAb bound and to subsequently extrapolate the EC50 by fitting the data to a sigmoidal dose-response curve with variable slope.

$1\times10^5$ MCF7 cells expressing LIV-1 in PBS/BSA were aliquoted in each well of a 96-well v-bottom plates on ice. The cells were incubated for 1 hour with 5 nM AlexaFluor-647 labeled murine LIV-1 mAb and increasing concentrations (from 0.38 nM to 600 nM) of unlabeled humanized LIV-1 mAb, combinations of humanized light chains LA-LF and humanized heavy chains HA-HE. Cells were pelleted and washed 3 times with PBS. The cells were pelleted and resuspended in 125 μL of PBS/BSA. Fluorescence was analyzed by flow cytometry, using percent of saturated fluorescent signal to determine percent labeled murine LIV-1 mAb bound and to subsequently extrapolate the BC50 by fitting the data to a sigmoidal dose-response curve with variable slope.

$1\times10^5$ CHO cells expressing recombinant cyno LIV-1 in PBS were aliquoted in each well of a 96-well v-bottom plates on ice. The cells were incubated for 1 hour with 5 nM AlexaFluor-647 labeled murine LIV-1 mAb and increasing concentrations (from 0.038 nM to 600 nM) of unlabeled humanized LIV-1 mAb, combinations of humanized light chains LA-LF and humanized heavy chains HA-HE. Cells were pelleted and washed 3 times with PBS. The cells were pelleted and resuspended in 125 μL of PBS/BSA. Fluorescence was analyzed by flow cytometry, using percent of saturated fluorescent signal to determine percent labeled murine LIV-1 mAb bound and to subsequently extrapolate the EC50 by fitting the data to a sigmoidal dose-response curve with variable slope.

Quantitative Flow Cytometric Analysis

Quantification of LIV-1 copy number on the cell surfaces was determined using murine LIV-1 mAb as primary antibody and the DAKO QiFiKit flow cytometric indirect assay as described by the manufacturer (DAKO A/S, Glostrup, Denmark) and evaluated with a Becton Dickinson FACS®can flow cytometer.

Cytotoxicity Assay

Tumor cells were incubated with LIV-1 antibody drug conjugates for 96-144 hours at 37° C. A non-binding (H00) ADC was used as a negative control. Cell viability was measured by resazurin (Sigma) at the final concentration of 50 μM. Cells were incubated for four to six hours at 37°. Fluorescent signal was measured on a Fusion HT fluorescent plate reader (Perkin concentration of compound needed to yield a 50% reduction in viability compound to vehicle-treated cells (control=100%).

Production of antibody Drug Conjugates

Antibody drug conjugates of the LIV-1 antibodies were prepared as described in US20050238649. The drug linkers vcMMAE (also referred to as 1006) and mcMMAF (referred to as 1269) are both described in US20050238649. Preparation of cysteine mutants of IgG1 antibodies is generally described in US20100158919. US20050238649 and US20100158919 are herein incorporated by reference for all purposes.

Production of Non-fucosylated Anti-LIV-1 mAb

A CHO DG44 cell line producing the humanized IgG1 anti-LIV-1 monoclonal antibody, HBLB mAb (hLIV-14), was cultured at $3.0\times10^5$ cells per mL in 30 mL of CHO culture media at 37°, 5% $CO_2$ and shaking at 100 RPM in a 125 mL shake flask. Media was supplemented with insulin like growth factor (IGF), penicillin, streptomycin and 65 μM 2-fluorofucose peracetate (SGD-2084) (see US20090317869). Cultures were fed on day 3 with 2% volume of feed media. On day four, the culture was split L4 into fresh culture media. Cultures were fed with a 6% volume of production feed media on days 5, 7, 9 and 10. Conditioned media was collected on day 13 by passing the culture through 0.2 μm filter. Antibody purification was performed by applying the conditioned media to a protein A column pre-equilibrated with 1× phosphate buffered saline (PBS), pH 7.4.

After washing column with 20 column volumes of 1×PBS, antibodies were eluted with 5 column volumes of Immunopure IgG elution buffer (Pierce Biotechnology, Rockford, Ill.). A 10% volume of 1M Tris pH 8.0 was added to eluted fraction. Sample was dialyzed overnight into 1×PBS.

ADCC activity was measured using the standard $^{31}$Cr-release assay. Briefly, the MCP-7 target tumor cells were labeled with 100 μCi $Na^{51}CrO_4$, washed, and pre-incubated with test antibodies prior to addition of effector (natural killer, NK) cells. NK ($Cd16^+$ $CD56^+$) cells were prepared from non-adherent peripheral blood mononuclear cells (PBMCs) obtained from normal FcγRIIIA 158V/V donors (Lifeblood, Memphis, Tenn.) with immunomagnetic beads (EasyStep, StemCell Technologies, Vancouver, BC, Canada). Viable NK cells were added to target cells at an effector to target cell ratio of 10:1. A human IgG1κ (Ancell, Bayport, Minn.) was used as negative control in this assay. After 4 hours of incubation, supernatants were collected and dried overnight on Luma plates. Gamma radiation emitted from lysed MCF-7 cells was then detected using the TopCount Microplate Scintillation and Luminescence Counter (Perkin Elmer, Waltham, Mass.). ADCC activity is reported as % specific lysis.

In Vivo Activity Study

Nude (m/m) mice (7-8 animals/group) were implanted with tumor cells grown in culture. MCF-7 from NCl ($5\times10^6$ cells in 25% matrigel), PC3 from ATCC ($2.5\times10^6$ cells in 25% matrigel), and PC3 from DSMZ ($5\times10^5$ in 25% matrigel). For in vivo growth of MCF-7 cells, female mice also received estrogen supplementation by implanting a slow-release estrogen pellet (90 day release). Dosing with either chimeric or humanized LIV-1 ADC or nonbinding control ADC (3 mg/kg) started when tumors reached 100 $mm^3$ (q4d×4 intra-peritoneal injections). Tumor volumes were monitored using calipers and animals were euthanized when tumor volume reached ~800 $mm^3$ Median tumor volume plots were continued for each group until one or more animals were euthanized. All animal procedures were performed under a protocol approved by the Institutional Animal Care and Use Committee in a facility accredited by the Association for Assessment and Accreditation of Laboratory Animal Care.

LIV-1 Immunohistochemical (IHC) Staining Method

Tumor microarrays (TMAs) and individual tumor samples were obtained from commercial sources. Tissue microarrays from normal or tumor formalin fixed and paraffin embedded (FFPE) tissues were purchased either from US Biomax Inc. or Cybrdi. A frozen array was purchased from BioChain. Single sections were purchased from NDRI, Asterand, Tissue Solution or CHTN. A set of 25 paraffin-embedded samples of metastatic hormone refractory prostate cancer (corresponding bone and soft tissue metastatic sites) was provided by Dr. R. Vessella, University of Washington, Genitourinary Cancer Department. All samples were processed on Bond-Max™ auto-stainer (Leica).

IHC Staining of FFPE Tissues:

FPPE slides or TMAs sectioned on glass slides were deparaffinized using Bond™ Dewax solution (Leica, cat #AR9222) at 72° C. and rehydrated. Antigen retrieval was performed using EDTA based Bond™ Epitope Retrieval Solution 2 (Leica, cat #AR9640) for 20 min at 95-100° C. before incubation with the primary murine LIV-1 mAb (1-2 μg/ml for 30-45 minutes at 25° C.). Isotype-matched murine IgG1 (Sigma; cat #M5284) was used as negative control for background staining. For automated IHC staining we used either a Refine DAB kit or an alkaline phosphatase based detection kit: Bond™ Polymer AP Red Detection kit (Leica, cat #DS9305). Slides were incubated with murine monoclonal primary antibodies against murine LIV-1 mAb for 45 min at 1 μg/ml with a preliminary 30 min protein block (DAKO cat #X0909). After chromogen development, sections were counterstained with hematoxylin and coverslipped. Slides were evaluated and scored by a pathologist and images were taken using a Zeiss Axiovert 200M microscope (Car Zeiss, Inc., Thornwood, N.Y.).

IHC of Frozen Tissues:

5 μm sections of frozen/OCT samples were acetone fixed for 10 min., air dried for 30 min, and pretreated 20 min with 1× Morphosave at room temperature. The slides were loaded into Bond-Max™ auto-stainer (Leica) and stained for 45 min with primary antibody with preliminary 30 min protein block (DAKO cat# X0909). Mouse IgG1 (BD Pharmingen cat #550878) was used as negative control. For detection we used DAB-based Bond Polymer Refine kit (Leica, cat #DS9800). After chromogen development, sections were counterstained with hematoxylin and coverslipped. Slides were evaluated and scored by pathologist.

Results

1. Binding of Mouse Antibody

The $K_D$ for the murine LIV-1 monoclonal antibody BR2-14a antibody (US2004141983) was determined for human LIV-1 expressed as an endogenous protein in a human breast cancer cell line or as a recombinant protein in a CHO cell line. The $K_D$ for the murine LIV-1 antibody BR2-14a was also determined for cyano LIV-1 expressed as a recombinant protein in a CHO cell line. MCF7 is a human breast cancer cell line. 293F is a human embryonic kidney cell line. Table 1 shows that the antibody had about 5-fold lower dissociation constant for non-recombinant LIV-1 expressed from a human cell line than recombinant LV-1, wherein human (hLIV-1) or from cynomolgus monkeys (cyLIV-1).

TABLE 1

| Cell line | Antigen | Kd (nM) |
|---|---|---|
| MCF-7 (ATCC) | hLIV-1 | 2.4 |
| 293F (hLIV-1) | hLIV-1 | 2.7 |
| CHO (hLIV-1) | hLIV-1 | 12.5 |
| CHO (cyLIV-1) | cLIV-1 | 14.0 |

2. Design and Testing of Humanized Antibodies

The starting point or donor antibody for humanization in this Example is the mouse antibody BR2-14a produced by the hybridoma having ATCC Accession No. PTA-5705A and descried in US2004141983. Suitable human acceptor sequences are genomic sequences provided by VH1-02 and JH5 for the heavy chain and by VK2-30 and Jk4 for the light chain. The human acceptor sequences show 68 and 85 percentage identity to the donor sequences in the variable region frameworks. The light chain CDRs of the human acceptor sequences are of the same canonical type as the CDRs of the donor sequences. In contrast, the heavy chain CDRs of the human acceptor sequences differed in their canonical type (the germline was 1-3 versus 1-2 for the murine donor).

Alignment of the donor sequences identified eleven positions in the heavy chain (H27, H28, H29, H30, H48, H66, H67, H71, H76, H93 and H94) and five positions in the light chain (L36, L37, L45, L46 and L39) at which the human acceptor sequence differed from the donor sequence and that may affect antibody binding as a result of contacting antigen directly, affecting conformation of CDRs or affecting packing between heavy and light chains. Five humanized heavy chains and six humanized light chains were made incorporating back mutations at different permutations of these positions (FIG. 1 (sequence alignment) and Table 2).

TABLE 2

Backmutations

| $V_H$ variant | VH exon acceptor sequence | donor framework residues |
|---|---|---|
| $hV_HA$ | VH1-02 | none |
| $hV_HB$ | VH1-02 | H29, H30, H76 |
| $hV_HC$ | VH1-02 | H66, H67, H71 |
| $hV_HD$ | VH1-02 | H27, H93, H94 |
| $hV_HE$ | VH1-02 | H27, H28, H29, H30, H48, H76, H66, H67, H71, H93, H94 |
| **$V_L$ variant** | **VL exon acceptor sequence** | **donor framework residues** |
| $hV_KA$ | VK2-30 | none |
| $hV_KB$ | VK2-30 | L36 |
| $hV_KC$ | VK2-30 | L37 |
| $hV_KD$ | VK2-30 | L45 |
| $hV_KE$ | VK2-30 | L46 |
| $hV_KF$ | VK2-30 | L36, L37, L39, L45, L46 |

Humanized antibodies were then expressed representing every permutation of these chains (30 possibilities) of the humanized heavy and light chains. The binding curves for recombinant human LIV-1 expressed from CHO cells are shown in FIG. 2. The EC50's are summarized in the Table 3 below.

TABLE 3

$EC_{50}$s for humanized LIV-1 mAb antibodies, derived from BR2-14a, on human LIV-1 expressed in CHO cells

| Ab | EC50 (μg/mL) |
|---|---|
| HALA | DNB |
| HALB | 37.8 |
| HALC | 25.5 |
| HALD | 4.9 |
| HALE | DNB |
| HALF | 8.8 |
| HBLA | 19.9 |
| HBLB | 0.3 |
| HBLC | 44.0 |
| HBLD | 17.4 |
| HBLE | DNB |
| HBLF | 0.7 |
| HCLA | DNB |
| HCLB | 1.8 |
| HCLC | DNB |
| HCLD | 66.6 |
| HCLE | DNB |
| HCLF | 1.3 |
| HDLA | DNB |
| HDLB | 2.3 |
| HDLC | DNB |
| HDLD | 67.9 |
| HDLE | DNB |
| HDLF | 1.4 |
| HELA | 12.5 |

TABLE 3-continued $EC_{50}$s for humanized LIV-1 mAb antibodies, derived from BR2-14a, on human LIV-1 expressed in CHO cells

| Ab | EC50 (μg/mL) |
|---|---|
| HELB | 173.3 |
| HELC | DNB |
| HELD | 24.2 |
| HELE | 0.3 |
| HELF | 1.5 |

DNB means "did not bind"

These data indicate considerable variation of EC50 between the 30 humanized antibodies tested with HBLB and HELE showing at least two fold better binding that the next humanized antibody HBLF and larger margins over most of the humanized antibodies. The binding curves of FIG. 2 show that both HBLB and HELE had stronger binding than the original mouse antibody.

The HBLB antibody was selected as the best of the humanized antibodies because it has (together with HELE) the strongest binding but has fewer backmutations versus HELE, there being four back mutations in HBLB and twelve in HELE.

Figure 3:
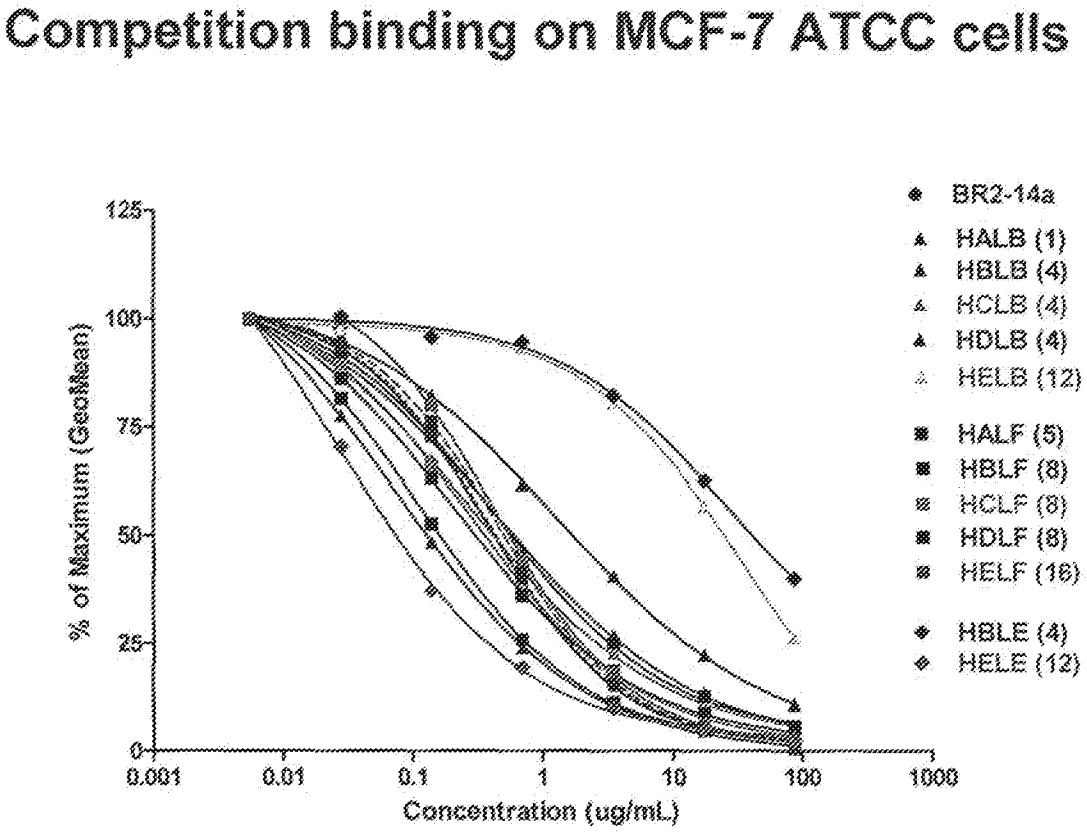
FIG. 3 shows the results of competition binding studies of the humanized LIV-1 mAbs and the parental murine antibody (referred to as BR2-14a). The numbers in parentheses after each variant indicate the number of back mutations.

The EC50s for the humanized LIV-1 mAb which bound human LIV-1 expressed on CHO cells were determined for human LIV-1 expressed as a native protein in an MCF7 cell line (FIG. 3). Again, LIV-1 mAb HBLB and HELE were determined to be the tightest binders.

Figure 4:
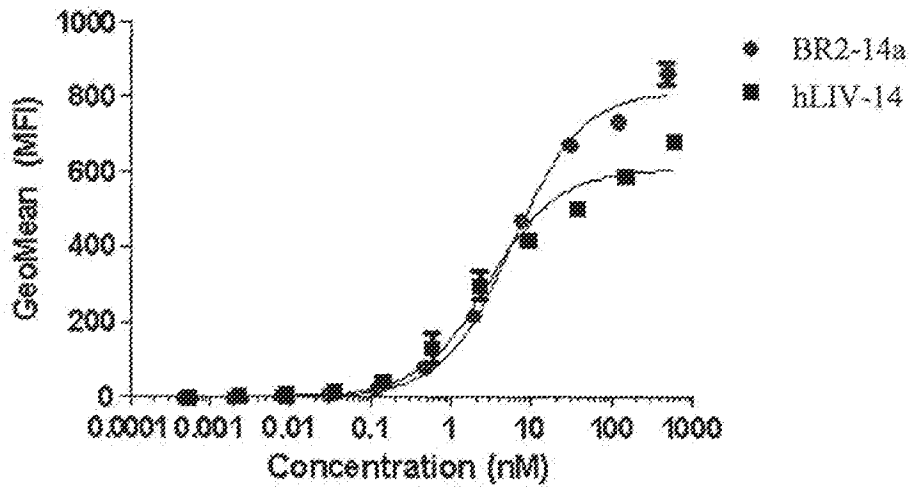
FIG. 4 shows the results of saturation binding studies on MCF7 cells. BR2-14a-AF refers to AF-labeled parental murine antibody hLIV-14 refers to AF-labeled HBLB antibody, a humanized antibody that specifically binds to LIV-1.

The Kd for HBLB to human LIV-1 on the MCF7 cell line was determined from the average of several saturation binding curves as 1.5 nM whereas that for the mouse antibody is 2.9 nM. In other words, the HBLB antibody has about twice the affinity for native human LIV-1 as the mouse antibody. The saturation binding curve shown in FIG. 4 is a representative example.

Figure 5:
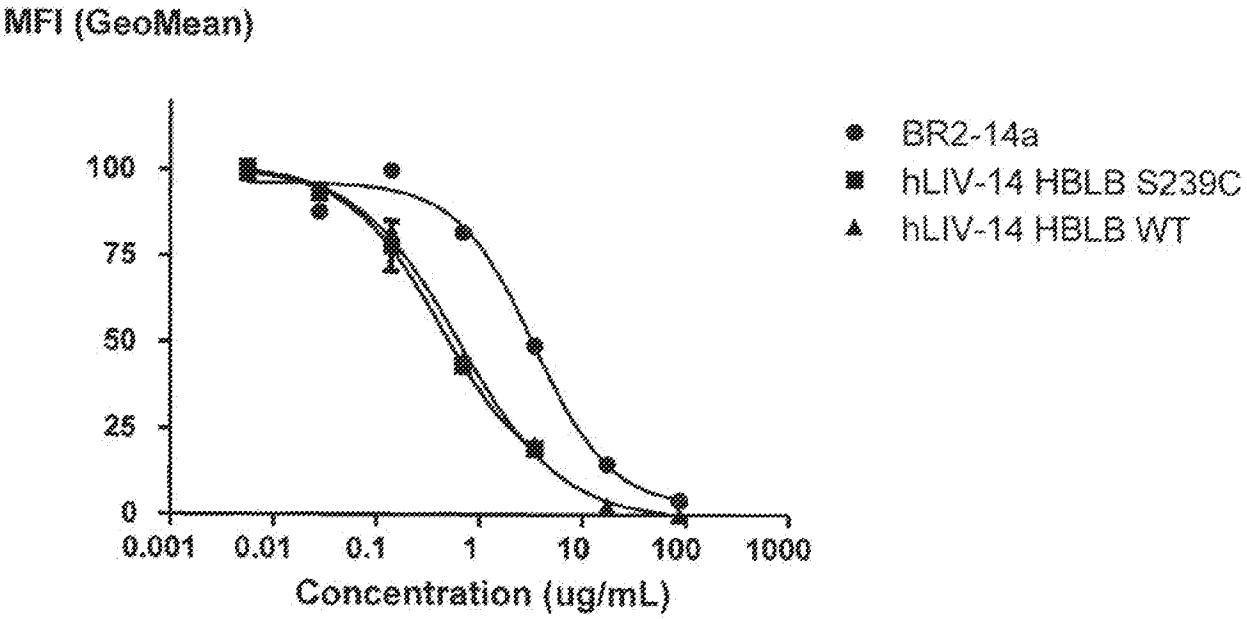
FIG. 5 shows the results of competition binding studies on CHO cells expressing recombinant LIV-1 protein. BR2-14a refers to the parental murine antibody. hLIV-14 HBLB WT refers to the HBLB antibody, hLIV-14 HBLB S239C refers to the HBLB antibody having serine to cysteine substitutions at each position in the heavy chain.

Two forms of the HBLB were compared for binding to human LIV-1 recombinantly expressed from CHO cells. One form was expressed with wildtype human IgG1 and kappa constant regions. The other form was the same except for an S239C mutation (EU numbering) in the IgG1 heavy chain (referred to as LIV-14d or HBLB S239C), which reduces binding of the antibody to Fc gamma receptors. The binding curves and EC50's of these antibodies compared with the mouse donor antibody are shown in FIG. 5. The EC50's of both forms of HBLB were similar to one another (within the error of the study), and both were stronger than the mouse antibody.

The EC50s for the humanized LIV-1 mAb HBLB and HBLB S239C were also determined for cyno LIV-1 expressed as a recombinant protein in a CHO cell line. Both antibodies bound with equal affinity (better than murine LIV-1 mAb).

Expression Data for LIV-1

Murine LIV-1 mAbs (at least 2 for concordance) were used for immunohistochemical analysis of various tumor types using formalin-fixed paraffin embedded tissues.

TABLE 4

Summary of the expression data for LIV-1 in tumor samples

| Origin | Type | LIV-1+ | # cases | % |
|---|---|---|---|---|
| Breast | Primary & metastatic (TMA) | | | 28-46 |
| | Primary tumors | 12 | 12 | 100 |
| | Metastatic tumors | 17 | 19 | 89 |
| | Post-hormone treatment | 19 | 22 | 86 |
| | Triple Negative | 13 | 20 | 65 |

TABLE 4-continued

Summary of the expression data for LIV-1 in tumor samples

| Origin | Type | LIV-1+ | # cases | % |
|---|---|---|---|---|
| Prostate | Metastatic hormone refractory: bone mets | 15 | 25 | 60 |
| | soft tissue mets | 21 | 25 | 84 |
| Ovarian | Primary (TMA) | 9 | 72 | 13 |
| | Metastatic (TMA) | 4 | 11 | 36 |
| | Post-chemo treated | 5 | 17 | 29 |
| Endometrial | | 7 | 56 | 12 |
| Squamous cell carcinoma (uterine and multiple organs) | Primary tumors | 8 | 114 | 7 |
| Pancreatic | Primary tumors | 9 | 95 | 9 |
| Lung | Primary tumors (TMA) | 3 | 192 | 2 |

Figure 6:
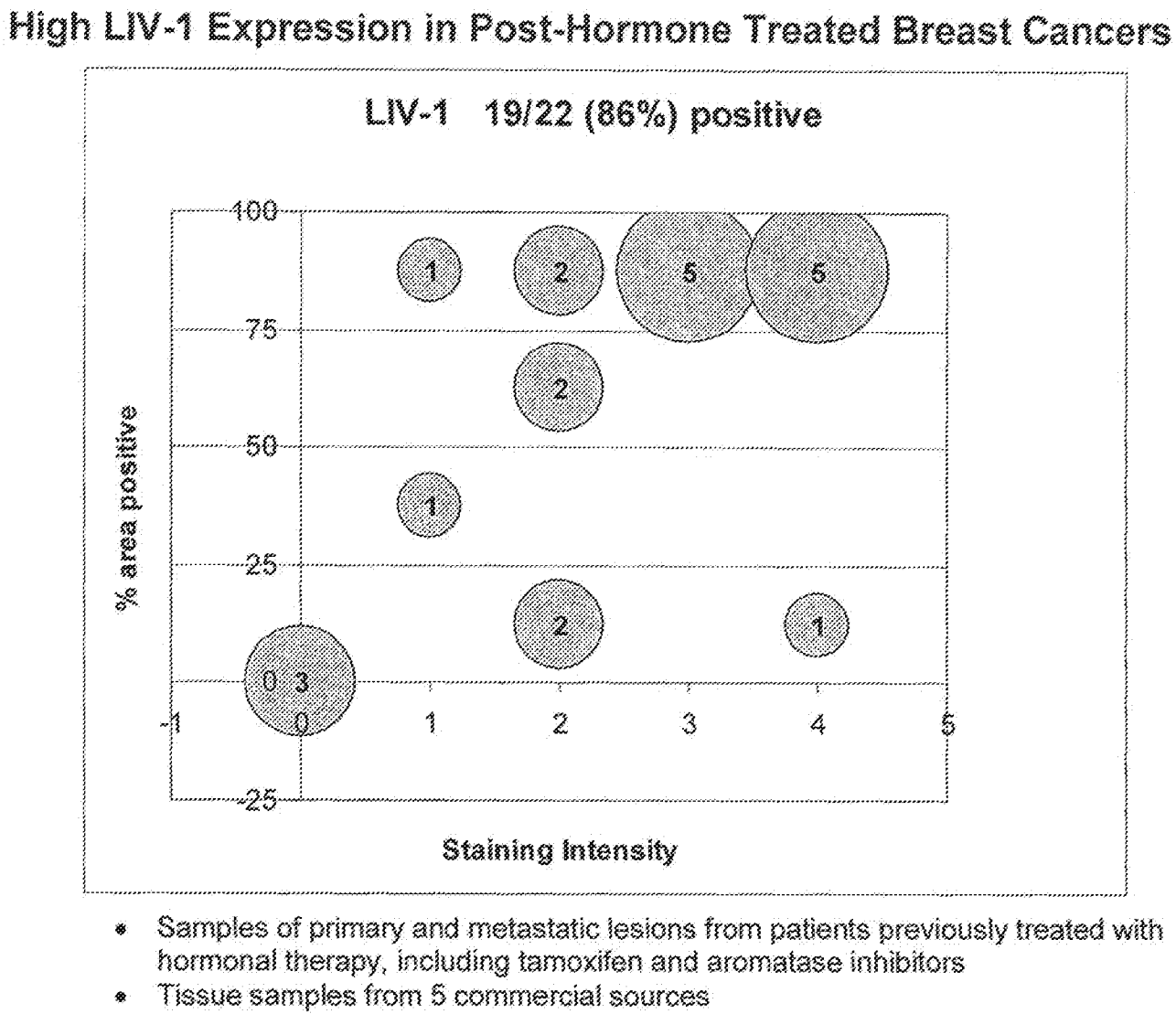
FIG. 6 shows an analysis of LIV-1 protein expression by IHC on post-hormone treated breast cancer patient samples.
Figure 8:
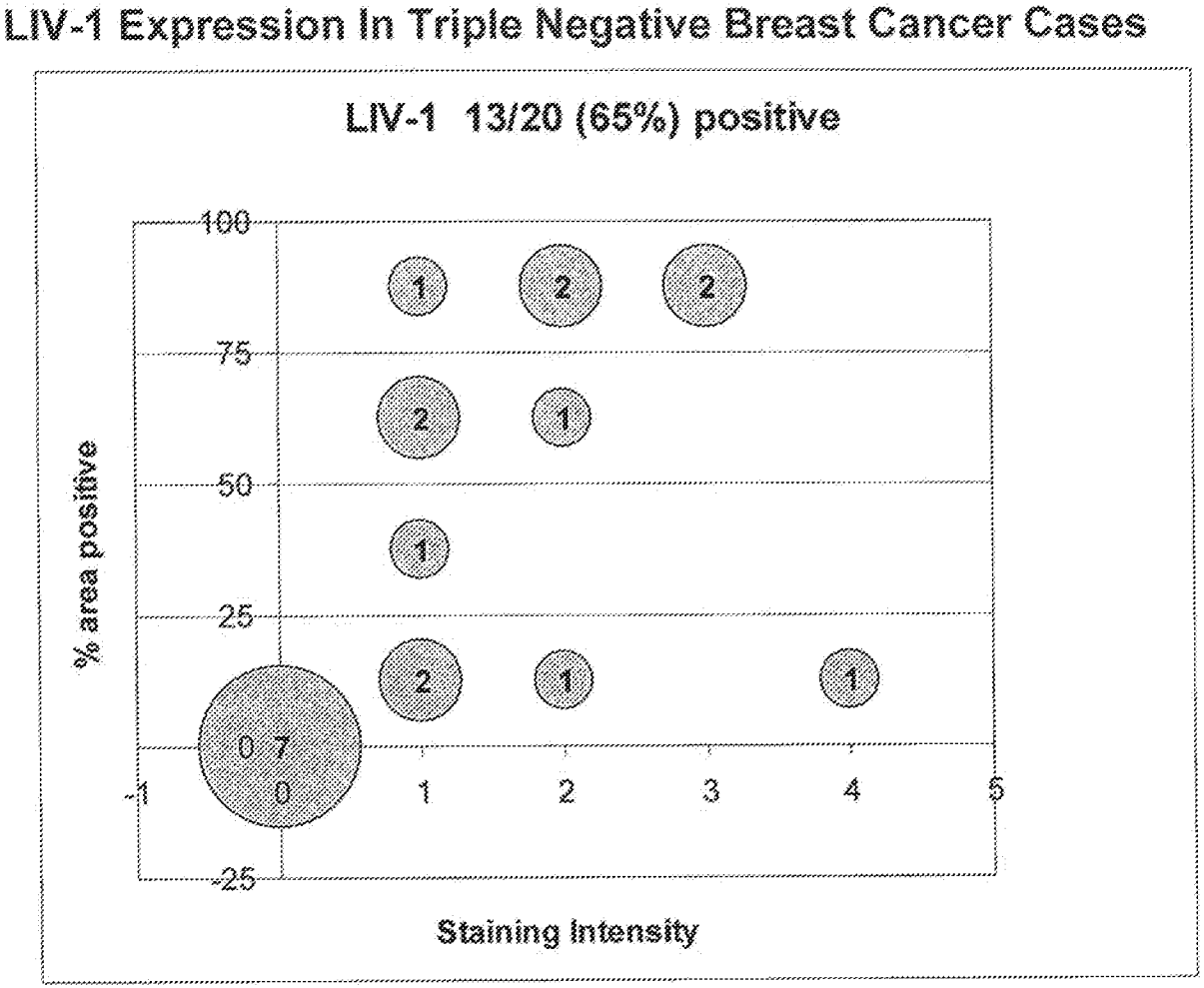
FIG. 8 shows an analysis of LIV-1 protein expression by IHC on triple negative breast cancer patient samples.

We observed lower LIV-1 IHC positivity in studies done using tissue microarrays compared to large tissue sections. The difference in expression is highly significant suggesting analysis of LIV-1 expression in larger tissue sections is preferred. There was good concordance of expression using at least 2 different anti-LIV-1 mAbs. FIGS. 6 and 7 show a high level of LIV-1 expression in post-hormone (tamoxifen or aromatase inhibitors) treated breast and prostate tumors providing a strong rationale to target these tumors using a LIV-1 ADC. FIG. 8 shows detectable LIV-1 expression in triple negative (ER-, PgR-, Her2-) breast cancer tissues. The LIV-1 level of expression in triple negative breast cancer by immunohistochemistry staining was comparable to the level in the PC3 animal model, where we demonstrated anti-tumor activity of LIV-1 ADC. Triple negative breast cancers were therefore a potential target population, particularly triple negative breast cancers which have been found to express LIV-1.

In Vitro Anti-tumor Activity of hLIV-14 mAb as ADC and Effector Function Enhanced mAb (SEA)

Figure 9:
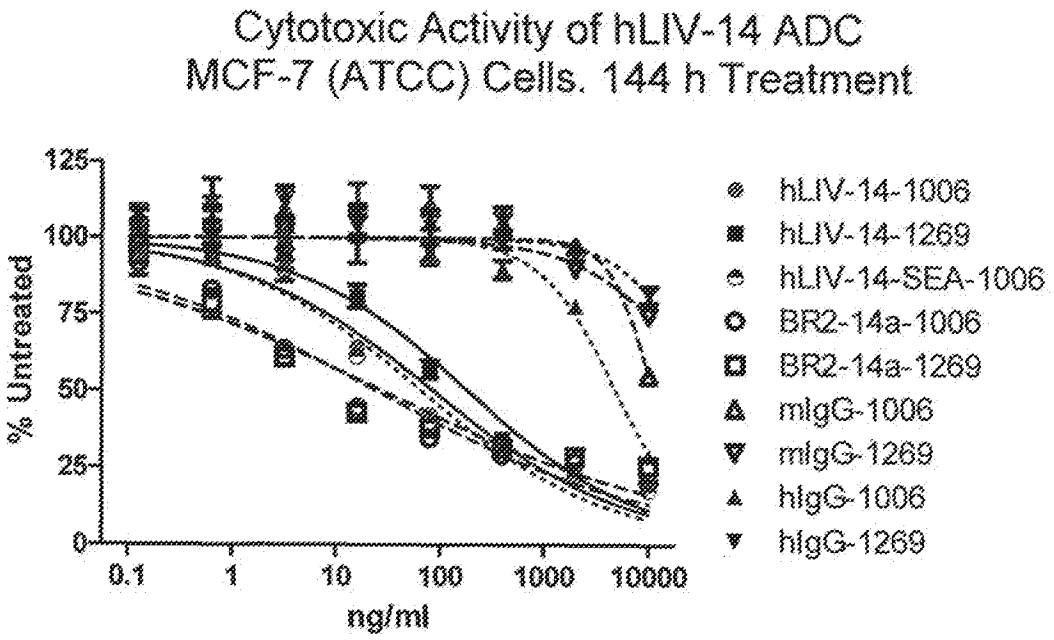
FIG. 9 shows the results of cytotoxicity assays on hLIV-14 antibody drug conjugates, i.e., the HBLB mAb conjugated to vcMMAE (1006) or mcMMAF (1269), as well as conjugates of control murine (mIgG) and human (hIgG) antibodies. hLIV-14-SEA-1006 refers to a non-fucosylated form of the HBLB mAb conjugated to vcMMAE (1006).
Figure 10:
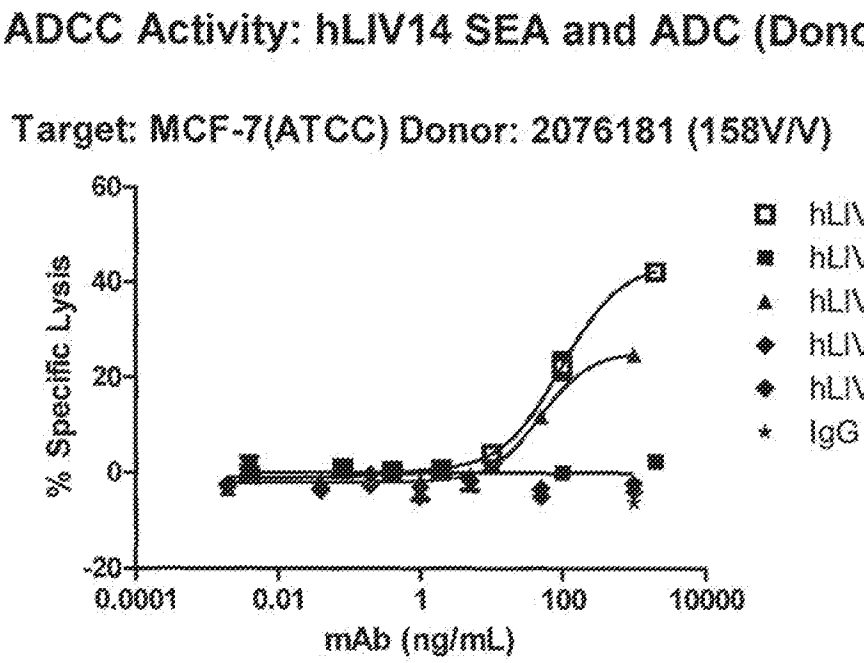
FIG. 10 shows the results of an in vitro ADCC assay on MCF7 cells using human NK cells (donor 1; V/V). hLIV-14 WT refers to the HBLB mAb. hLIV-14 SEA refers to the non-fucosylated form of the HBLB mAb. hLIV-14 mcMMAF refers to an antibody drug conjugate of the HBLB mAb conjugated to mcMMAF. hLIV-14 vcMMAE refers to an antibody drug conjugate of the HBLB mAb conjugated to vcMMAE. hLIV-14 SEA vcMMAE refers to a non-fucosylated form of the HBLB mAb-vcMMAE antibody drug conjugate.
Figure 11:
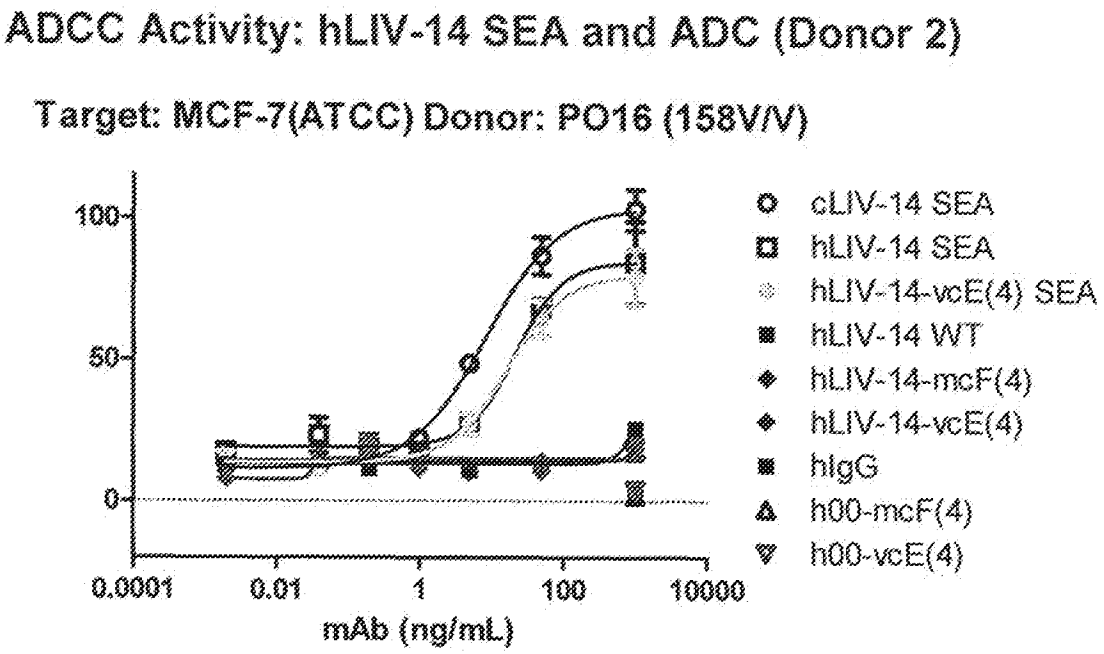
FIG. 11 shows the results of an in vitro ADCC assay on MCF7 cells using human NK cells (donor 2). hLIV-14 WT refers to the HBLB mAb. hLIV-14 SEA refers to the non-fucosylated form of the HBLB mAb. cLIV-14 SEA refers to the non-fucosylated form of the chimeric parental murine antibody hLIV-14 mcF(4) refers to an antibody drug conjugate of the HBLB mAb with an average of 4 mcMMAF drug linker molecules per antibody. hLIV-14 vcE(4) refers to an antibody drug conjugate of the HBLB mAb with an average of 4 vcMMAE drug linker molecules per antibody. hLIV-14 vcE(4) SEA refers to a non-fucosylated form of the HBLB mAb-vcMMAE antibody drug conjugate having an average of four vcMMAE drug linker molecules per antibody. hIgG refers to control human IgG. H00-mcF(4) refers to a control antibody drug conjugate of a nonbinding antibody with an average of 4 mcMMAF drug linker molecules per antibody. H00-vcE(4) refers to a control antibody drug conjugate of a nonbinding antibody with an average of 4 vcMMAE drug linker molecules per antibody.

Anti-tumor activity of LIV-1 ADCs in vitro was measured using both cytotoxicity assays (FIG. 9) and antibody dependent cell cytotoxicity (ADCC) (FIGS. 10 and 11). First, we performed a survey of LIV-1 expression in various cell lines by quantitative FACS analysis. The breast cancer cell line MCF-7 from ATCC had the highest level of LIV-1 binding sites/cell, as compared to the MCF-7 cell line from other sources (data not shown). We used this cell line for both assays in vitro. Referring to FIG. 9, various hLIV-14 ADCs (the HBLB antibody conjugated with vcMMAE (referred to as 1006) or mcMMAF (referred to as 1269) (both small molecules and/or linkers described in US20050238649)) were highly effective in killing MCF-7 cells, as compared with the nonbinding and murine control conjugates (mIgG-1006, mIgG-1269, hIgG-1006, and hIgG-1269). In addition cysteine mutant LIV-14d ADCs, having an average of two drug linkers per antibody were also highly effective in killing MCF-7 cells as measured by the cytotoxic assay. Referring to FIGS. 10 and 11, in ADCC assays the activity of the fucosylated/wild-type (WT) mAb and ADC's were compared with the effector-function enhanced versions (non-fucosylated mAbs and ADCs, referred to as SEA). The results demonstrated that effector function enhanced LIV-1 mAbs and ADCs have good ADCC activity against MCF-7 cells, as computed to non-effector function enhanced mAbs or ADCs (compare, for example, FIG. 10 hLIV-1 SEA and vcMMAE with hLIV-1 vcMMAE). Referring again to FIG. 9, an effector function enhanced LIV-1 ADC (indicated as SEA) also had a similar level of cytotoxic activity as wildtype (non-fucosylated) ADCs (compare hLIV-1 SEA 1006 (vcMMAE) with hLIV-1 1006 (vcMMAE)). Thus cytotoxicity can be affected by both effector function and conjugate action.

In Vivo Anti-tumor Activity of hLIV-14 ADC

Figure 12:
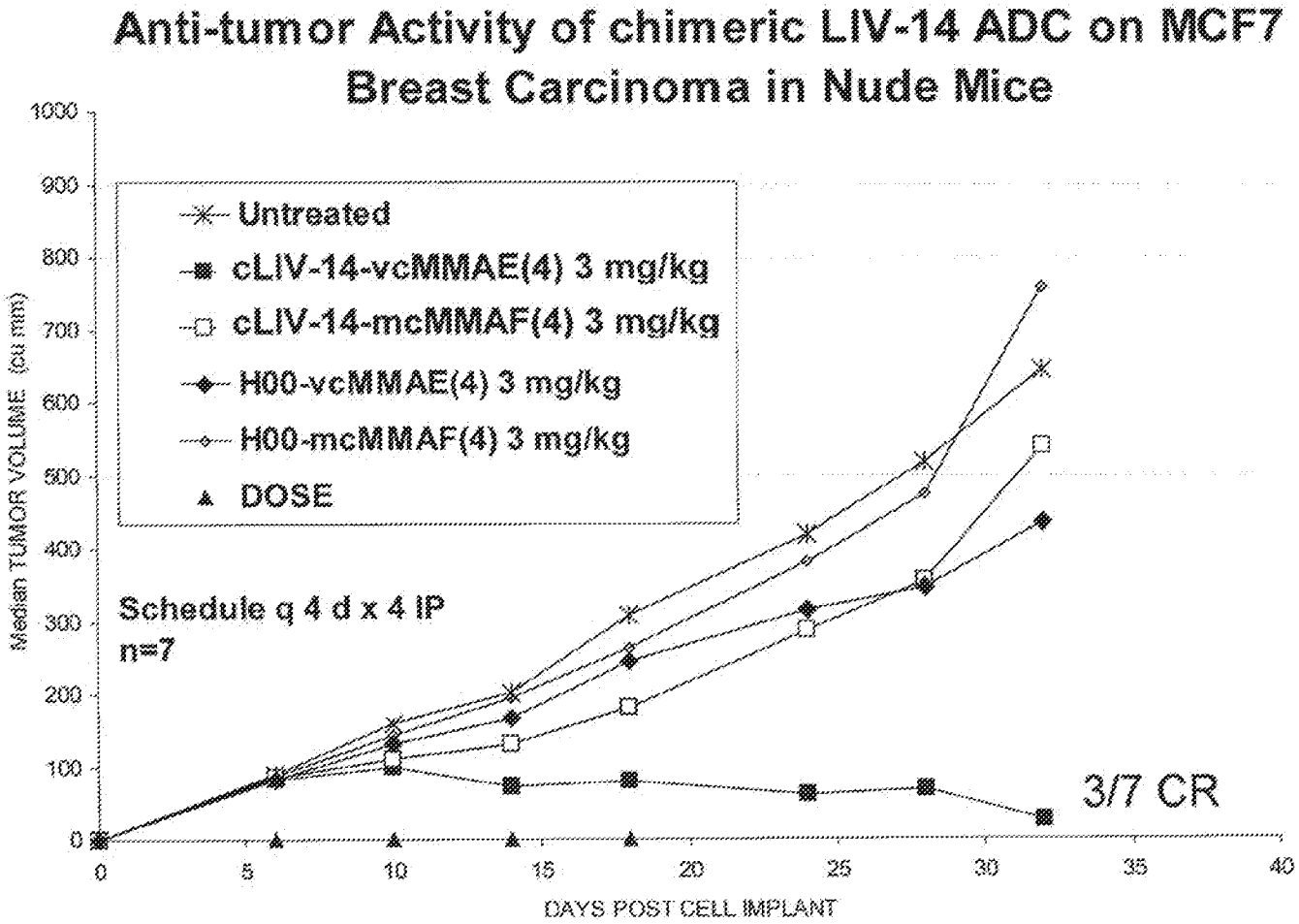
FIG. 12 shows the results of a xenograft study of the MCF7 breast cancer line in nude mice. cLIV-14-mcMMAF (4) refers to an antibody drug conjugate of the chimeric form of the parental murine antibody having an average of 4 mcMMAF drug linker molecules per antibody. cLIV-14-vcMMAE(4) refers to an antibody drug conjugate of the chimeric form of the present murine antibody having an average of 4 vcMMAE drug linker molecules per antibody. H00-mcMMAF(4) refers to an antibody drug conjugate of a nonbinding control antibody having an average of 4 mcMMAF drug linker molecules per antibody. H00-vcMMAE(4) refers to an antibody drug conjugate of a nonbinding control antibody having an average of 4 vcMMAE drug linker molecules per antibody. The dose and time of administration of indicated on the figures.
Figure 13:
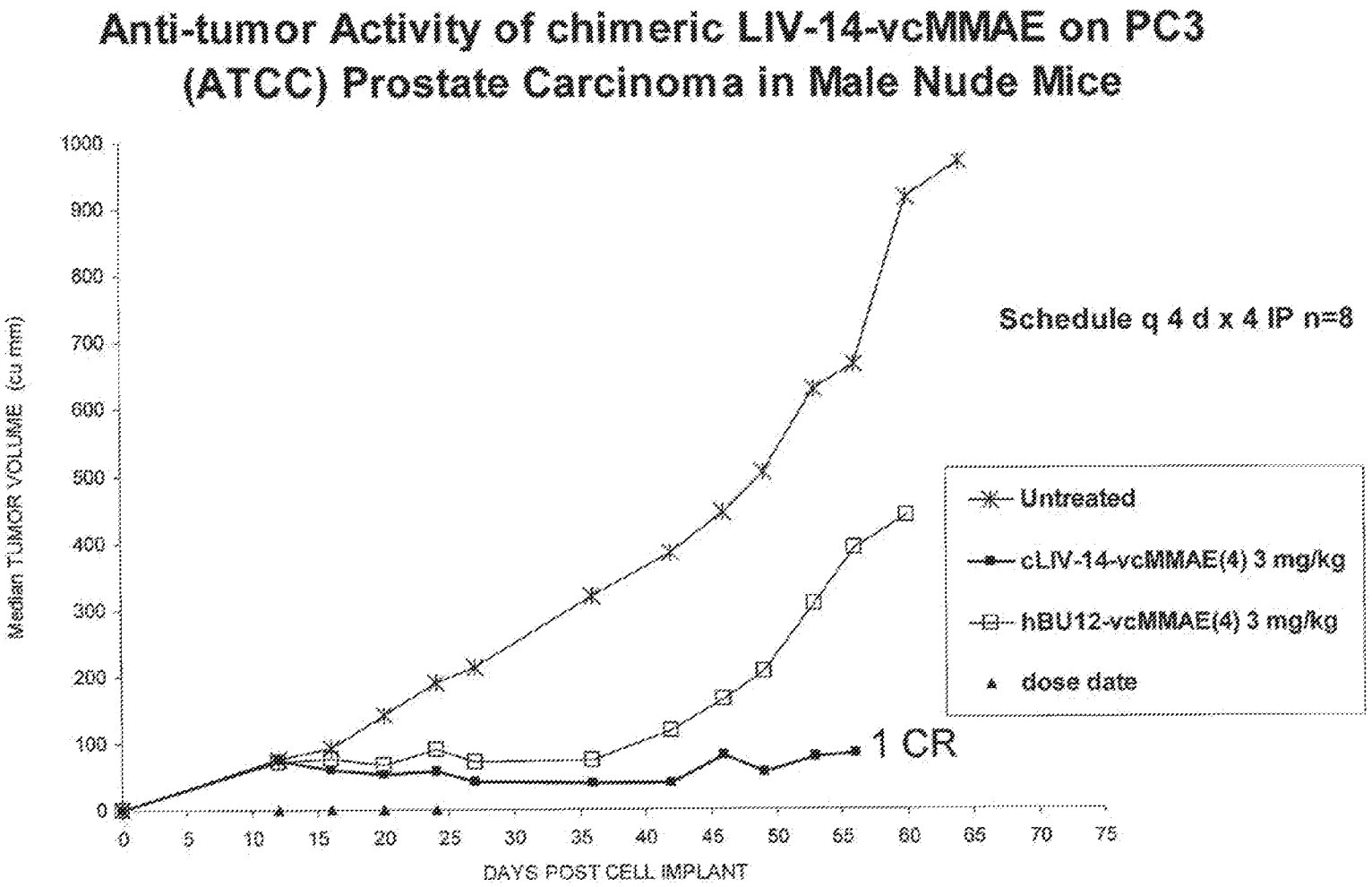
FIG. 13 shows the results of a xenograft study of the PC3 prostate cancer line in male nude mice. cLIV-14-vcMMAE (4) refers to an antibody drug conjugate of the chimeric form of the parent murine antibody having an average of 4 vcMMAE drug linker molecules per antibody. hBUC12-vcMMAE(4) refers to an antibody drug conjugate of an anti-CD19 antibody having an average of 4 vcMMAE drug linker molecules per antibody. The dose and time of administration of indicated on the figure.
Figure 14:
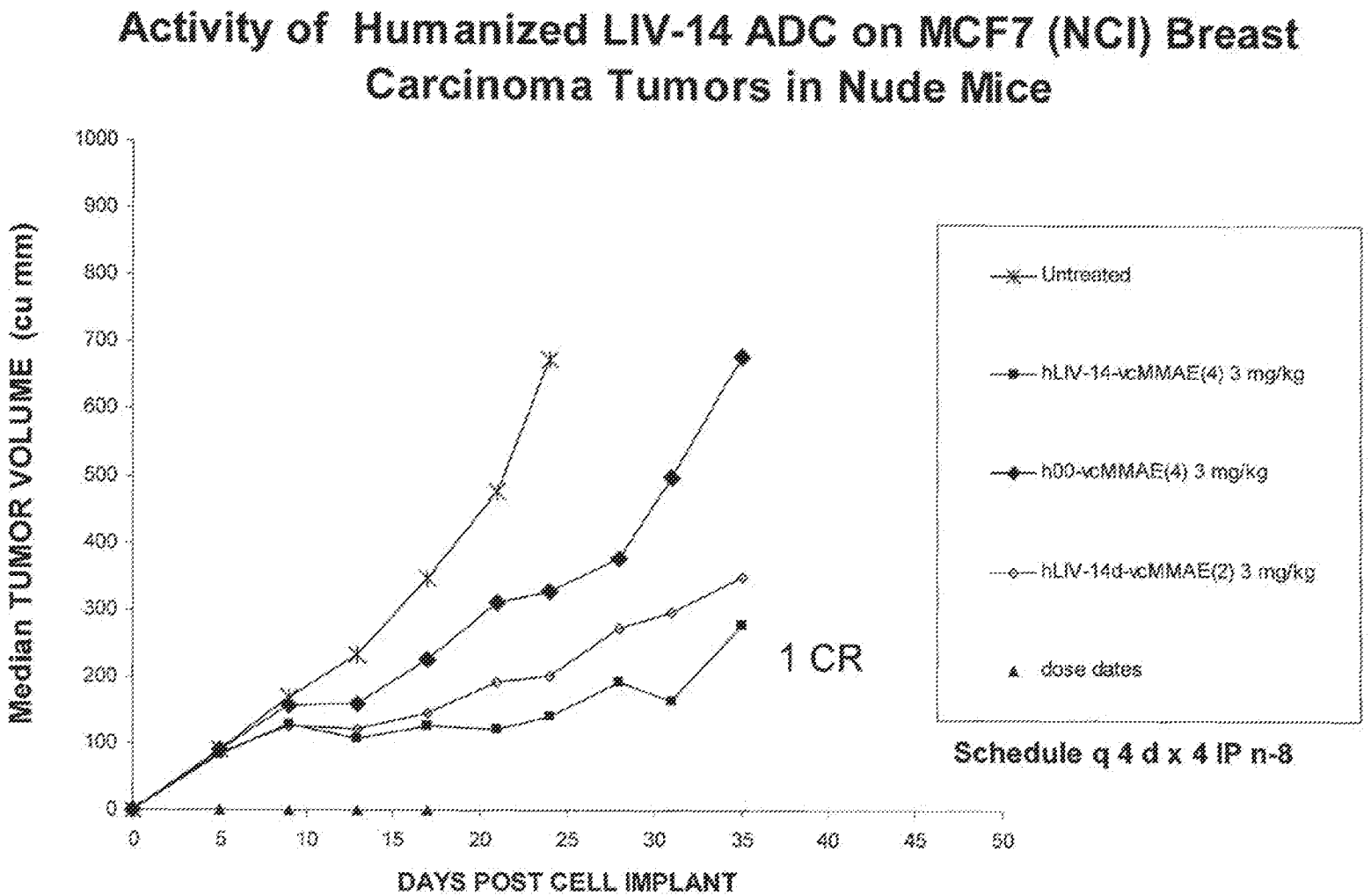
FIG. 14 shows the results of a xenograft study of the MCF7 breast cancer line in nude mice hLIV-14-vcMMAE (4) refers to an antibody drug conjugate of the HBLB antibody having an average of 4 vcMMAE drug linker molecules per antibody. hLIV-14d-vcMMAE(2) refers to an antibody drug conjugate of the HBLB antibody having an average of 2 vcMMAE drug linker molecules per antibody, each conjugated at the S239C position of each heavy chain. H00-vcMMAE(4) refers to an antibody drug conjugate of a nonbinding control antibody having an average of 4 vcMMAE drug linker molecules per antibody. The dose and time of administration of indicated on the figure.
Figure 15:
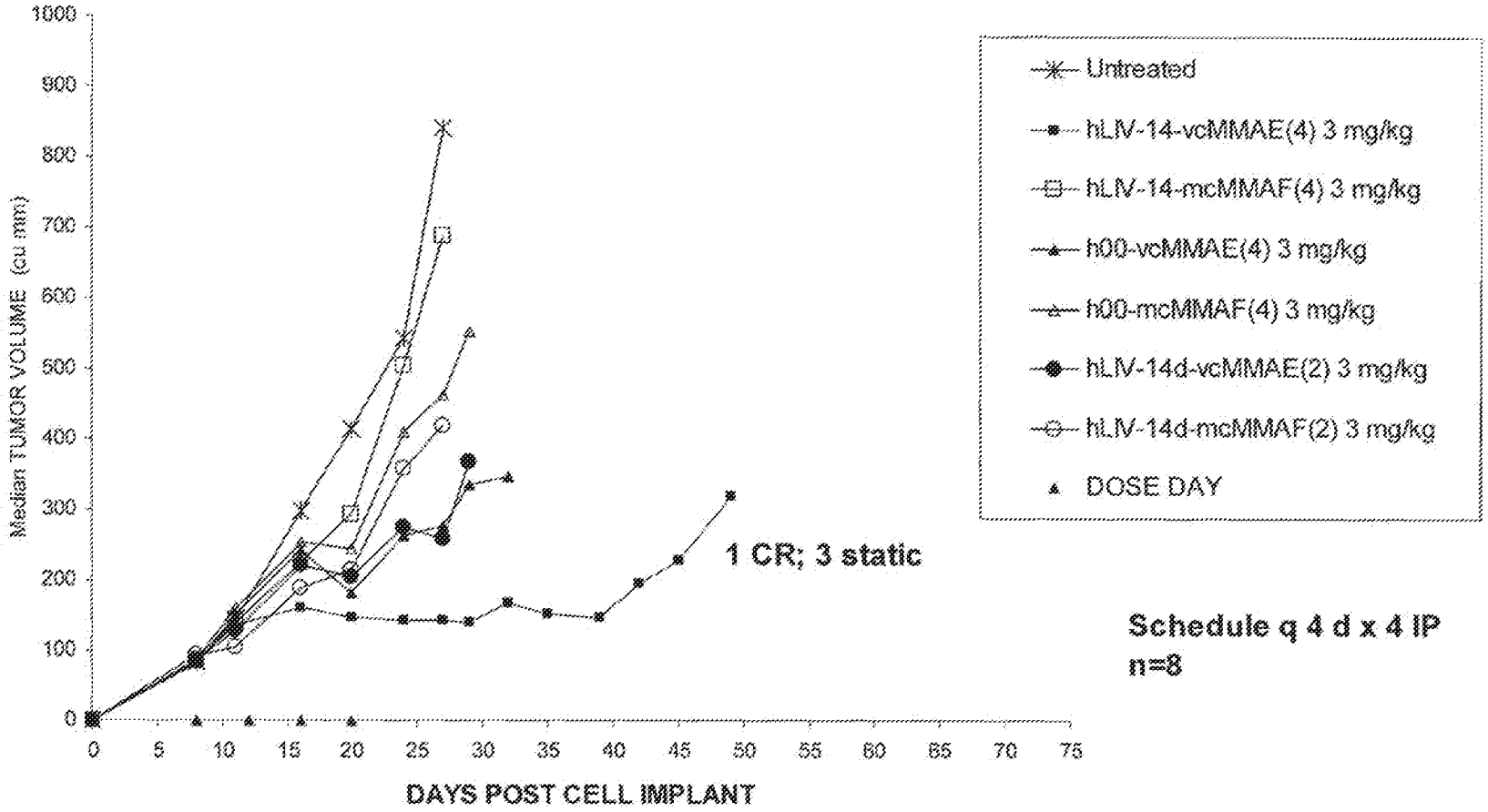
FIG. 15 shows the results of a xenograft study of the PC3 prostate cancer line in male nude mice. hLIV-14-vcMMAE (4) refers to an antibody drug conjugate of the HBLB antibody having an average of 4 vcMMAE drug linker molecules per antibody. hLIV-14-mcMMAF(4) refers to an antibody drug conjugate of the HBLB antibody having an average of 4 mcMMAF drug linker molecules per antibody. hLIV-14d-mcMMAE(2) refers to an antibody drug conjugate of the HBLB antibody having an average of 2 vcMMAE drug linker molecules per antibody, each conjugated at the S239C position of each heavy chain. hLIV-14d-mcMMAF(2) refers to an antibody drug conjugate of the HBLB antibody having an average of 2 mcMMAF drug linker molecules per antibody, each conjugated at the S239C position of each heavy chain. H00-vcMMAE(4) refers to an antibody drug conjugate of a nonbinding control antibody having an average of 4 vcMMAE drug linker molecules per antibody. H00-mcMMAF(4) refers to an antibody drug conjugate of a nonbinding control antibody having an average of 4 mcMMAF drug linker molecules per antibody. The dose and time of administration of indicated on the figure.

Using breast cancer (MCF-7) and prostate cancer (PC-3) models, we determined the anti-tumor activity of LIV-1 ADCs (chimeric and humanized (HBLB) mAbs with an average of 4 drugs per antibody) in vivo (FIGS. 12-15). LIV-1 ADCs conjugated to vcMMAE showed significant tumor delay compared to untreated and control ADCs. At least one complete regression (CR) was observed in all the studies using LIV-1-vcMMAE at 3 mg/kg with a number of animals having tumors that were static or grew slowly compared to controls. Referring to FIG. 12, a chimeric form of the parental murine antibody conjugated to vcMMAE resulted in complete regressions in 3 out of 7 mice. Referring to FIG. 13, the same chimeric ADC produced a complete regression in 1 out of 8 mice. Referring to FIG. 14, a humanized ADC (HBLB) conjugated to vcMMAE (hLIV-14-mvMMAE)(4)) produced a complete regression in 1 out of 8 times. In addition, a cysteine mutant form of the HBLB antibody, a vcMMAE drug linker conjugated to each heavy chain at position 239, producing at conjugate with an average drug load of 2 drug linkers per antibody; designated hLIV-14d-vcMMAE(2)) exhibited similar activity as the 4-loaded form. Referring to FIG. 15, the humanized ADC (HBLB) conjugated to vcMMAE (hLIV-14-vcMMAE(4)) produced a complete regression in 1 out of 8 mice in a prostate carcinoma model. In contrast, the activity of the two loaded cysteine mutants was not as pronounced in this model (compare hLIV-14-vcMMAe(4) with hLIV-14d-vcMMAE(2), and hLIV-14-mcMMAF(4) with hLIV-14d-mcMMAF(2). In summary, these studies demonstrate that LIV-1 ADC can stop or delay growth of LIV-1 expressing cancers including breast and prostate.

II. Humanization of BR2-22a

BR2-22a, sometimes also referred to as an mAb2, in a mouse monoclonal antibody of isotype IgG1Kappa.

Methodologies:

Unless otherwise stated below, methods described for humanization and testing of BR2-14a are also applicable to BR2-22.

Saturation Binding Assays $1\times10^5$ antigen expressing cells (either MCF7 cells expressing human LIV-1, 293F cells, a transfected CHO cell line expressing human LIV-1 or a transfected CHO cell line expressing cyno LIV-1) were aliquoted per wall of 96-well v-bottom plates. AtexaFlour-647 labeled murine BR2-22a was added in concentrations ranging from 0.66 pM to 690 nM and incubated on ice for 30 minutes. Cells were pelleted and washed 3× with PBS/BSA. The cells were then pelleted and resuspended in 125 μL of PBS/BSA. Fluorescence was analyzed by flow cytometry, using percent of saturated fluorescent signal to determine percent bound and to subsequently calculate apparent Kd.

Competition Binding Assays $1\times10^5$ CHO cells expressing recombinant LIV-1 in PBS were aliquoted into each cell well of a 96-well v-bottom plates on ice. The cells were incubated for 1 hour with 5 nM AlexaFluor-647 (AF) labeled parental BR2-22a and increasing concentrations (from 0.038 nM to 600 mM) of unlabeled humanized BR2-22a antibody in all combinations of humanized light Chains LA-LG and humanized heavy chains HA-HG. Cells were pelleted and washed 3 times with PBS. The cells were then pelleted and resuspended in 125 μL of PBS/BSA. Fluorescence was analyzed by flow cytometry, using percent of saturated fluorescent signal to determine percent labeled humanized BR2-22a antibody bound and to subsequently extrapolate the EC50 by fitting the data to a sigmoidal dose-response curve with variable slope.

In Vitro Activity Study

Nude (nn/nn) mice (7-8 animals/group) were implanted with tumor cells grown in culture MCF-7 (NCI) at $5\times10^6$ in 25% matrigel, PC3 from ATCC ($2.5\times10^6$ cells in 25% matrigel), and PC3 from DSMZ ($5\times10^5$ in 25% matrigel). For in vivo growth of MCF-7 cells, female mice also received estrogen supplementation by implanting a slow-release estrogen pellet (90 day release). Dosing with either chimeric or humanized LIV-1 ADC or nonbinding control ADC (3 mg/kg) started when tumors reached 100 $mm^3$ (q4d×4 intraperitoneal injections). Tumor volumes were monitored using calipers and animals were euthanized when tumor volume reached ~800 $mm^3$ Median tumor volume plots were continued for each group until one or more animals were euthanized. All animal procedures were performed under a protocol approved by the Institutional Animal Care and Use Committee in a facility accredited by the Association for Assessment and Accreditation of Laboratory Animal Care.

Summary of Results and Discussion

Saturation Binding

BR2-22a shows 94% identity to BR2-14a in the mature heavy chain variable region and 91% identity in the mature light chain variable region. The KD for the murine LivI of BR2-22a (Table 5) was determined for human LIV-1 expressed as an endogenous protein in a human breast cancer cell line, in 293F cells or as a recombinant protein in a CHO cell line. The KD for BR2-22a was also determined for cyno LIV-1 expressed as a recombinant protein in a CHO cell line.

TABLE 5

Affinity measurements of BR2-22a for human (hLIV-1) and cyno LIV-1 (cyLIV-1).

| Cell line | Antigen | Kd (nM) |
|---|---|---|
| MCF7 (ATCC) | hLIV-1 | 1.1 |
| 293F (hLIV-1) | hLIV-1 | 0.5 |
| Cho hLIV-1 | hLIV-1 | 1.5 |
| Cho cyLIV-1 | cLIV-1 | 4.2 |

Humanization Study

The BR2-22a antibody was humanized using a VH1-02 JH5 germline acceptor sequence for the heavy chain and a VK2-30 JK4 acceptor sequence for the light chain. These acceptor sequences were chosen based on their having the highest sequence identity to the mature variable region frameworks of BR2-22A heavy and light chains. Initially five variant heavy chains were constructed. Each included the three Kabat CDRs from the heavy chain of BR2-22a, the chains differing in having from zero (VA) to 11 (VE) backmutations. Initially six variant light chains were constructed. Each included the three Kabat CDRs from the light chain of BR2-22a and from zero (LA) to four backmutations (LF). These backmutations were chosen as a result of modeling the BR2-22A antibody to identify positions with potential to interact with antigen directly, affect CDR conformation or affect the interface between heavy and light chains and based on prior experience in humanizing BR2-14a because of the high sequence identity between BR2-14a and BR2-22a. In fact, the same eleven positions in the heavy chain and same four positions in the light chain were considered for backmutation in both BR2-14a and BR2-22a (1.39 was not considered in BR2-22a because the mouse residue is the same as the human residue). The back mutations present in each variant of humanized BR2-22a are shown in Tables 6 and 7 below.

TABLE 6

| $V_H$ variant | VH exon acceptor sequence | donor framework residues |
|---|---|---|
| $hV_HA$ | VH1-02 | None |
| $hV_HB$ | VH1-02 | H29, H30, H76 |
| $hV_HC$ | VH1-02 | H66, H67, H71 |
| $hV_HD$ | VH1-02 | H27, H93, H94 |
| $hV_HE$ | VH1-02 | H27, H28, H29, H30, H48, H66, H67, H71, H76, H93, H94 |
| $hV_HF$ | VH1-02 | H27, H29, H30, H94 |
| $hV_HG$ | VH1-02 | H27, H29, H30, H76, H94 |

TABLE 7

| $V_L$ variant | VL exon acceptor sequence | donor framework residues |
|---|---|---|
| $hV_KA$ | VK2-30 | None |
| $hV_KB$ | VK2-30 | L36 |
| $hV_KC$ | VK2-30 | L37 |
| $hV_KD$ | VK2-30 | L45 |
| $hV_KE$ | VK2-30 | L46 |
| $hV_KF$ | VK2-30 | L36, L37, L45, L46 |
| $hV_KG$ | VK2-30 | L36, L46 |

The full sequence of the mature variable region of each variant is shown in FIGS. 16A and 16B.

Figure 17:
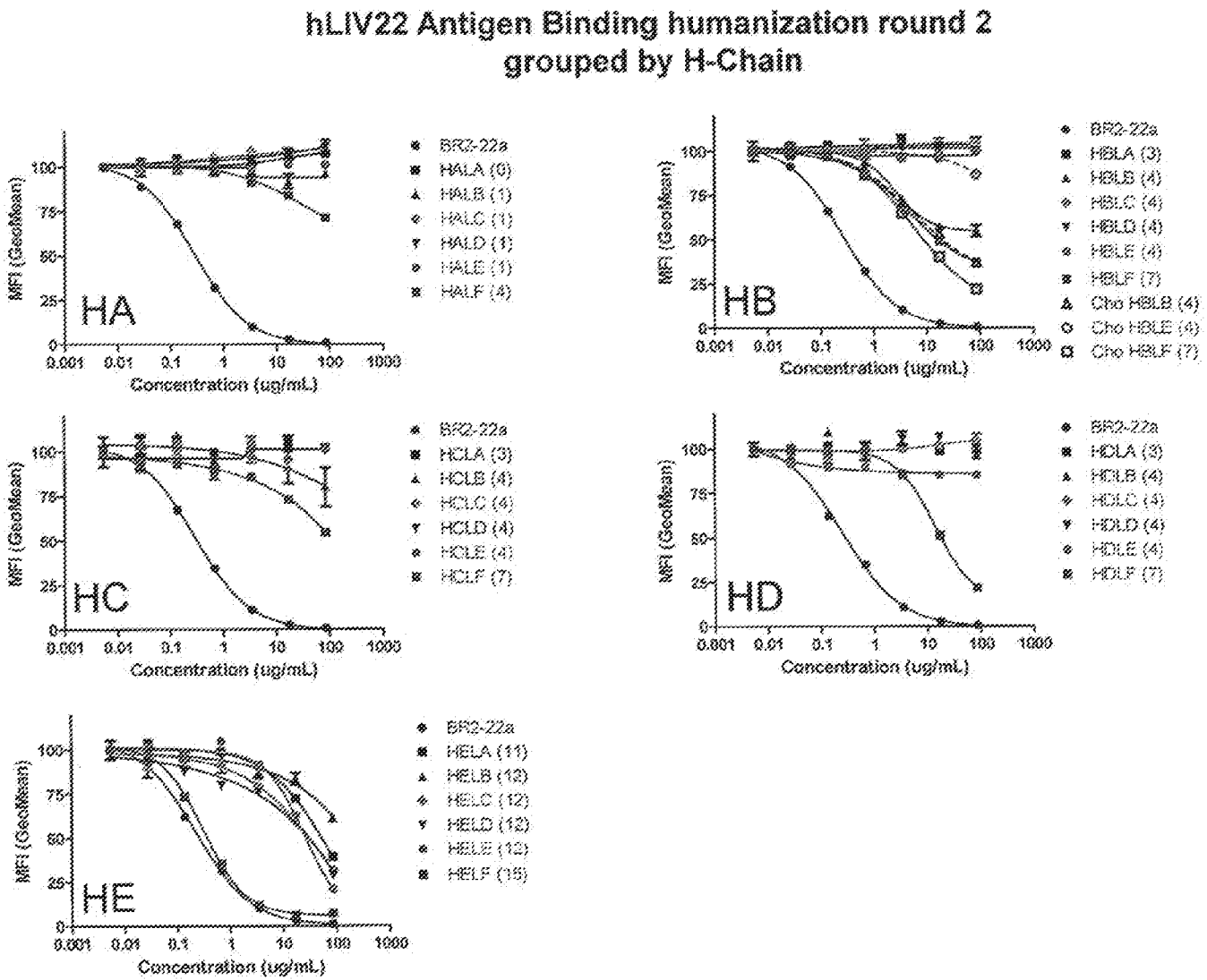
FIG. 17 shows competition binding assays of different permutations of humanized heavy chains HA-HF and humanized light chains LA-LF derived from the murine monoclonal anti LIV-1antibody BR2-22a. The total number of murine back mutations in each light or heavy chain is shown in parentheses. Only HELF showed sufficient retention of binding.

All permutations of these five heavy chains and six light chains were then tested in a competition assay compared with BR2-22a (see FIG. 17). Surprisingly, in view of the experience with the BR2-14a antibody in which improved binding relative to the mouse antibody was obtained with only four backmutations and further backmutations did not necessarily improve binding affinity, the only combination of humanized chains that showed binding affinity approximating that of BR2-22a was HELF with 15 backmutations. The other permutations showed poor or no significant binding to LIV-1. The EC50s of the different permutations are shown in Table 8 below.

TABLE 8

EC50s for humanized BR2-22a antibodies

| Ab | EC50 (μg/mL) |
|---|---|
| HALA | DNB |
| HALB | DNB |
| HALC | DNB |
| HALD | DNB |
| HALE | DNB |
| HALF | 33.2 |
| HBLA | DNB |
| HBLB | 4.9 |
| HBLC | DNB |
| HBLD | DNB |
| HBLE | DNB |
| HBLF | 6.5 |
| HCLA | DNB |
| HCLB | >100 |
| HCLC | DNB |
| HCLD | DNB |
| HCLE | DNB |

TABLE 8-continued

EC50s for humanized BR2-22a antibodies

| Ab | EC50 (μg/mL) |
|---|---|
| HCLF | >100 |
| HDLA | DNB |
| HDLB | DNB |
| HDLC | DNB |
| HDLD | DNB |
| HDLE | DNB |
| HDLF | 14.4 |
| HELA | 68.2 |
| HELB | >100 |
| HELC | 65.7 |
| HELD | >100 |
| HELE | 25.1 |
| HELF | 0.3 |
| HELG | 0.2 |
| HFLF | 0.8 |
| HFLG | 0.8 |
| HGLF | 0.4 |
| HGLG | 0.5 |

DNB means did not bind

Figure 19:
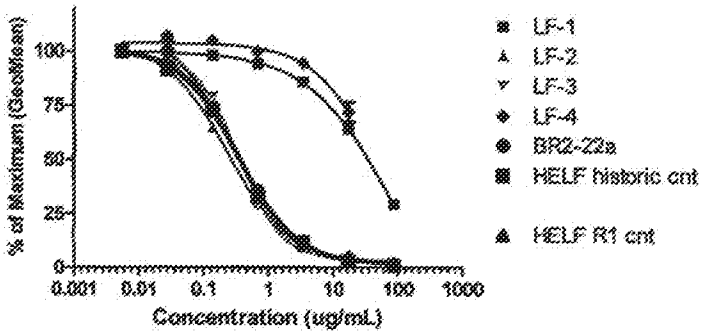
FIG. 19 shows competition binding of the LF variants on the top of the figure. The tested back mutations are shown in the bottom of the figure. Mouse residues are underlined. The remaining residues are human germline residues.
Figure 20:
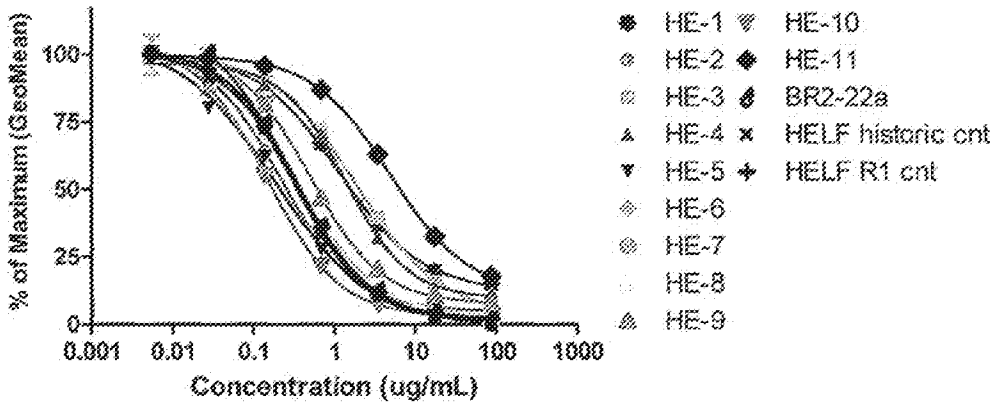
FIG. 20 shows competition binding of the HE variants on the top of the figure. The tested back mutations are shown in the bottom of the figure. Mouse residues are underlined. The remaining residues are human germline residues.

Although HELF shows satisfactory binding, the antibody contains a total of 15 backmutations, a number larger than ideal with respect to potential immunogenicity. Therefore, the HE and LF chains were systematically varied to test the effect of removing individual backmutations. FIG. 18 shows the variants tested. LF-1 through LF-4 differ from LF in each lacking a different backmutation prevent in LF. Similarly, HE-I through HE-I1 lack one of the backmutations present in HE. FIG. 19 compares LF-1 through LF-4 (each paired with HE). FIG. 19 shows that LF-2 and LF-3 lose substantial binding affinity relative to LF (indicated as HELF historic control in the graph), whereas LF-1 and LF-4 do not. It is concluded that backmutations L36 and L46 contribute substantially to retention to binding affinity, while backmutations at positions L37 and L45 can be dispensed without significant effect on binding. FIG. 20 shows similar binding curves for the HE variants. FIG. 20 shows that HF-11 lost most of its binding indicating that backmutation at position H94 has the greatest effect on binding affinity of the backmutations tested. Loss of backmutations at positions H27, H29 and H30 also caused significant loss of affinity. The role of H30 can be rationalized by the mouse residue being the result of somatic mutation. Loss of a back mutation at position H76 caused some loss of affinity. The other back mutations at positions H28, H48, H66, H67, H71 and H93 could be dispensed with little or no effect on binding affinity.

In light of these experiments, heavy chains HF and HG were constructed as was light chain LG. HF included backmutations at H27, H29, H30 and H94 and HG included these mutations and a backmutation at H76. LG contains backmutations at L36 and L46. Several permutations of HF, HG, LE and LF were tested for competition binding as shown in FIG. 21 and all showed binding within a factor of three of that of mouse BR2-22a.

In light of this experiment, HGLG was selected for further experiments as representing the best combination of binding affinity and fewest backmutations. This antibody is hereafter referred to as hLIV22. The saturation binding affinity of hLIV22 for human and cyano LIV-1 expressed from CHO cells is shown in FIG. 22 compared with that of hLIV14. FIG. 22 shows that hLIV22 has about four fold higher affinity (inverse of dissociation constant) for human LIV-1 that does hLIV14. Furthermore, the affinity of hLIV22 for human LIV-1 is the same within experimental error as its affinity for cynomolgus LIV-1, whereas hLIV14 shows twice the affinity for human LIV-1 as for cynomolgus LIV-1. The affinity of hLIV22 for human LIV-1 is the same within experimental error as that of the parent mouse antibody, BR2-22a.

In Vitro Anti-tumor Activity of hLIV22 ADCs

Figure 23:
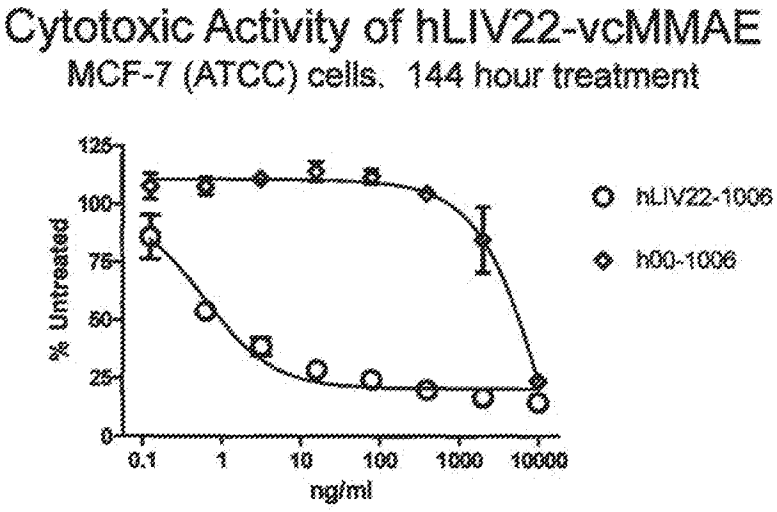
FIG. 23 shows cytotoxic activity of humanized LIV22-vcMMAE on MCF-7 cells after 144 hr of treatment. h00-1006 is a control drug-conjugated antibody.
Figure 24:
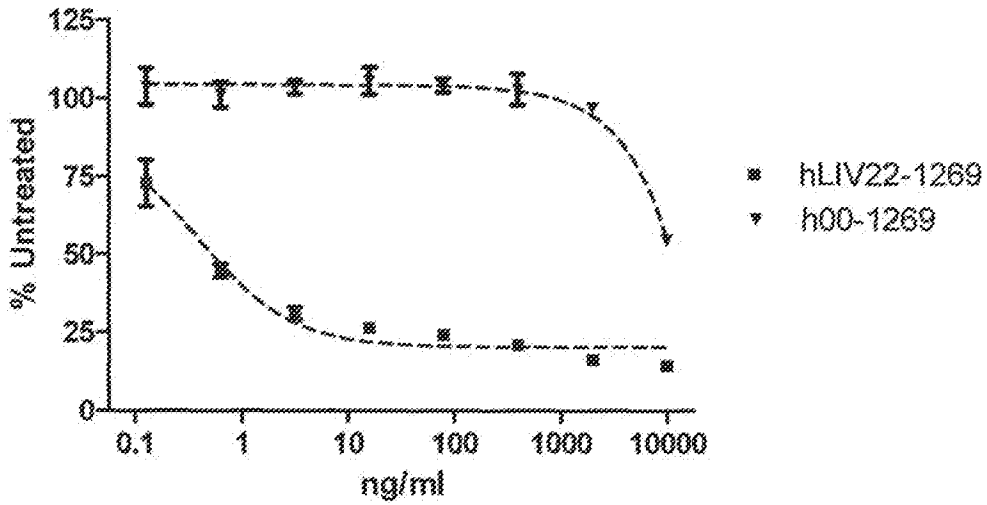
FIG. 24 shows cytotoxic activity of hLIV22-mcMMAF on MCF-7 cells after 144 hr of treatment. h00-1269 is a control drug-conjugated antibody.

Anti-tumor activity of hLIV22 ADC in vitro was measured using cytotoxicity assays. First, we performed a survey of LIV-1 expression in various cell lines by quantitative FACS analysis. The breast cancer cell line MCF-7 from ATCC had the highest level of LIV-1 binding sites/cell, as compared to the MCF-7 cell line from other sources (data not shown). We used this cell line for in vitro assays. We observed that various hLIV22 ADCs (configured with vcMMAE (referred to as 1006) or mcMMAF (referred to as 1269) (both small molecules described in US 2005-0238469)) were highly effective in killing MCF-7 cells as measured by the in vitro cytotoxic assay. FIGS. 23 and 24 compare hLIV22-conjugated to 1006 or 1269 with a non-binding control antibody conjugated to 1006 or 1269.

In Vitro Anti-tumor Activity of LIV-1 ADC

Figure 25:
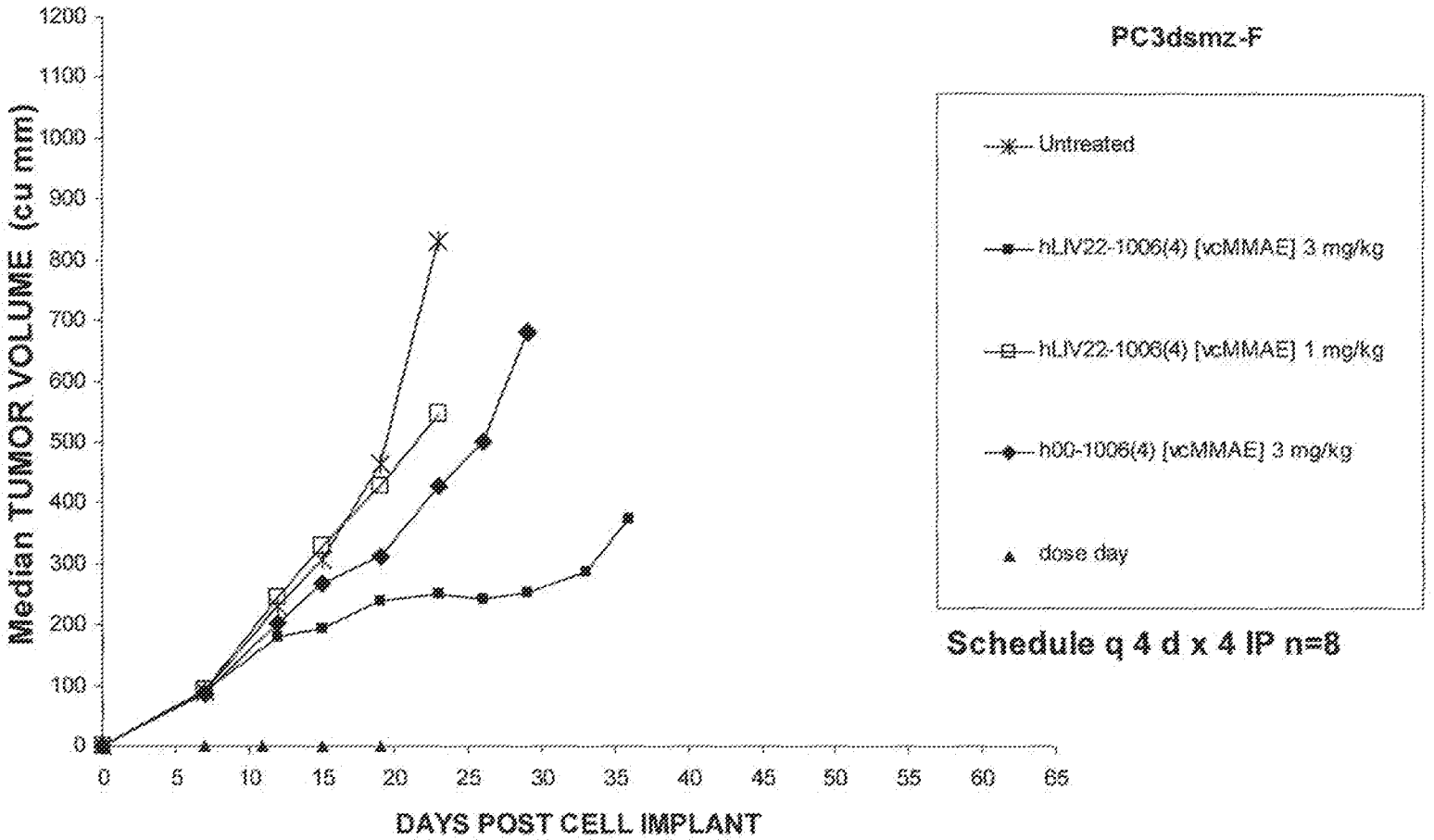
FIG. 25 shows the activity of hLIV22- antibody on PC3 (DSMZ) prostate carcinoma model in nude female mice. Dose days are indicated by triangles on the X-axis.
Figure 26:
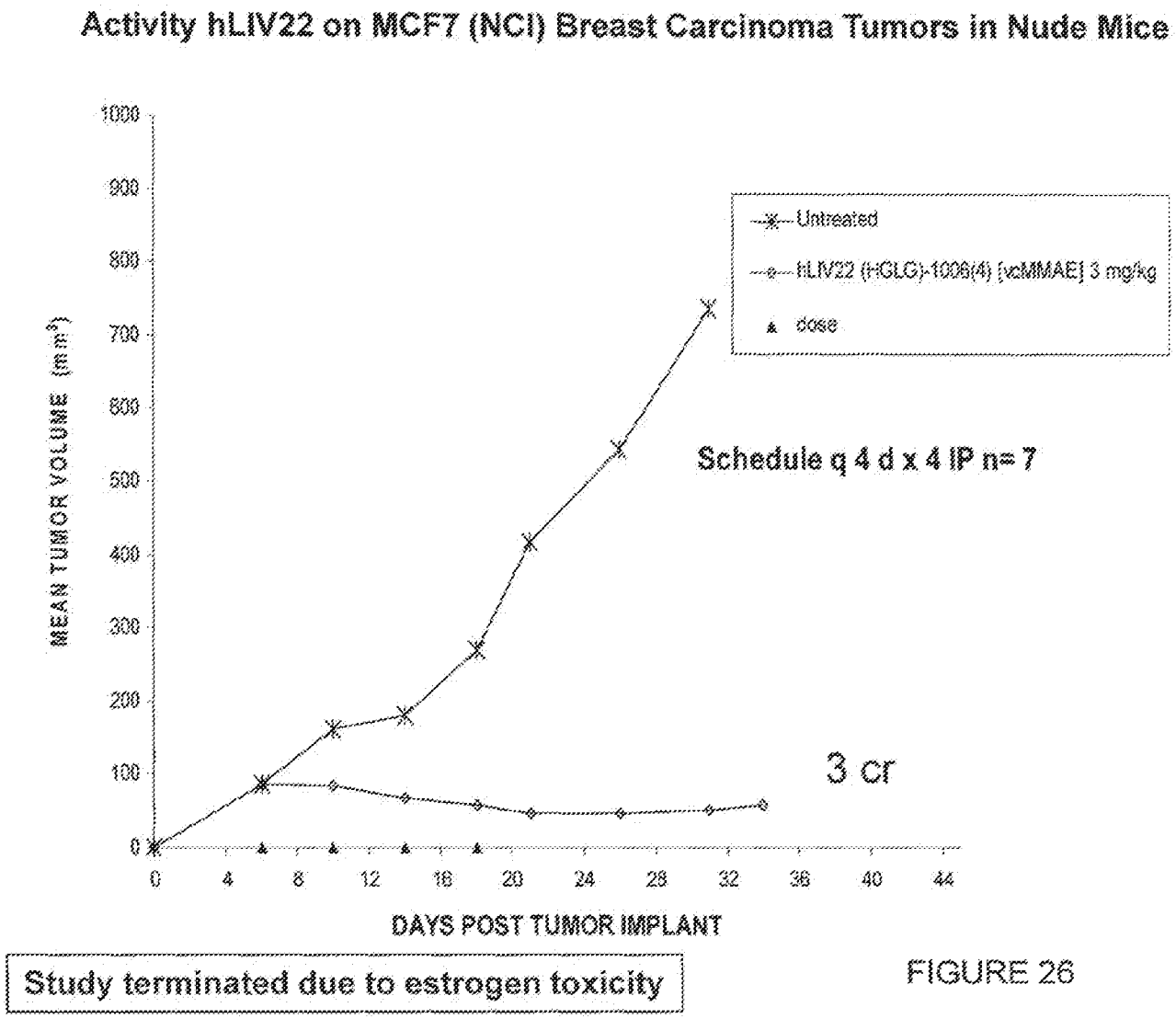
FIG. 26 shows that activity of hLIV22 antibody on MCF7 (NCI) breast carcinoma tumors in nude mice.
Figure 27:
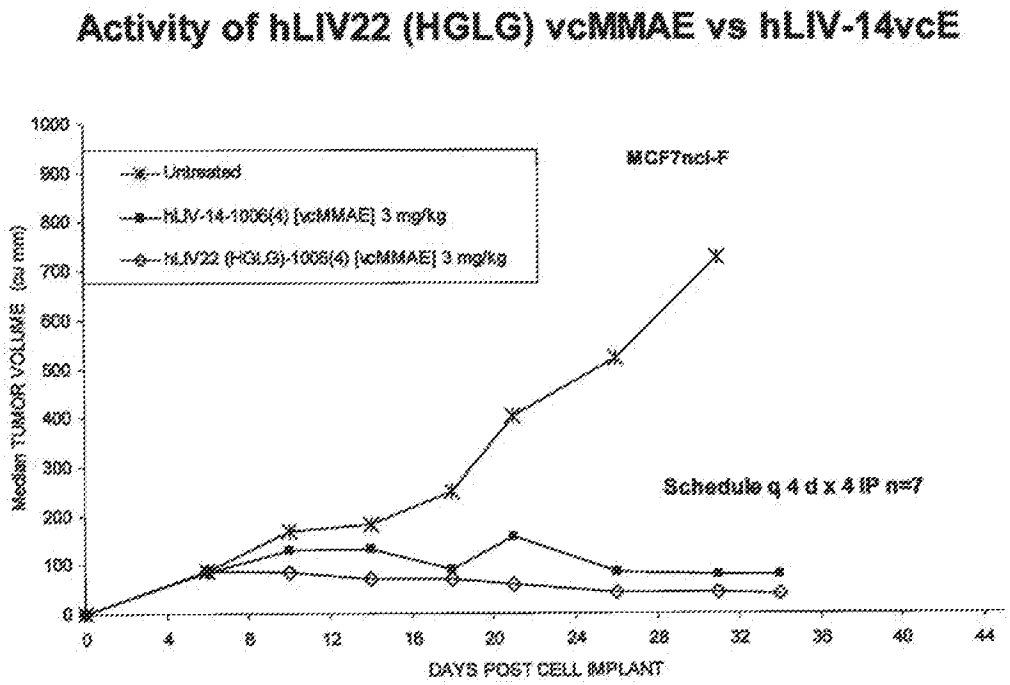
FIG. 27 compares the activity of hLIV22 and hLIV14 in the same mode as FIG. 26.

Using prostate cancer (PC-3) and breast cancer (MCF-7) models as shown in FIGS. 25 and 26, we determined the anti-tumor activity of hLIV22 ADCs (with an average of 4 drugs per antibody) in vivo. hLIV22 ADCs conjugated to vcMMAE showed significant tumor delay compared to untreated and control ADCs. There were multiple complete regressions was observed in the MCF-7 study using hLIV22-vcMMAE at 3 mg/kg. Additionally, in all studies there were a number of animals that had tumors that were static or grew slowly compared to controls. These studies demonstrate that hLIV 22 ADC can stop or delay growth of LIV-1 expressing cancers, including breast and prostate. FIG. 27 compares the activity of hLIV22 and hLIV14 ADCs in the MCF-7 model. Although both antibodies were effective, hLIV22 was slightly more effective. hLIV22 ADCs were also tested in a model of cervical cancer. A HeLA cell xenograft model was used for the assay. After tumors grew to an appropriate six, hLIV22 conjugated to vcMMAE was administered to animals at 3 mg/kg and 1 mg/kg. A control antibody conjugate was administered at 3 mg/kg. Complete and partial regression were observed in animals that received 3 mg/kg hLIV22 vcMMAE conjugate. (Data not shown.) Thus, LIV-1 antibodies and antibody drug conjugates can be used to treat LIV-1 expressing cervical cancers.

III. Treatment of Skin Cancer Using Anti-LIV-1 Antibodies

Expression of LIV-1 Protein on Melanoma Tumor Samples

Melanoma samples from patients were assessed for LIV-1 expression, using IHC staining. FFPE slides were de-paraffinized using Bond™ Dewax solution (Leica, cat #AR9222), at 72° C. Antigen retrieval was performed using EDTA based Bond™ Epitope Retrieval Solution 2 (Leica, cat #AR9640) for 20 min at 100° C. For IHC staining we used alkaline phosphatase based detection kit. Bond™ Polymer Refine Red Detection kit (Leica, cat #DS9390). Slides were incubated with murine monoclonal primary antibodies against LIV-1 (BR2-14a) for 45 min at 1 μg/ml with preliminary 30 min protein block (DAKO cat #X0909). Mouse IgG (Sigma, cat #M5284) was used as negative control. After chromogen development, sections were counterstained with hematoxylin and coverslipped. Slides were evaluated and scored by pathologist.

Figure 28:
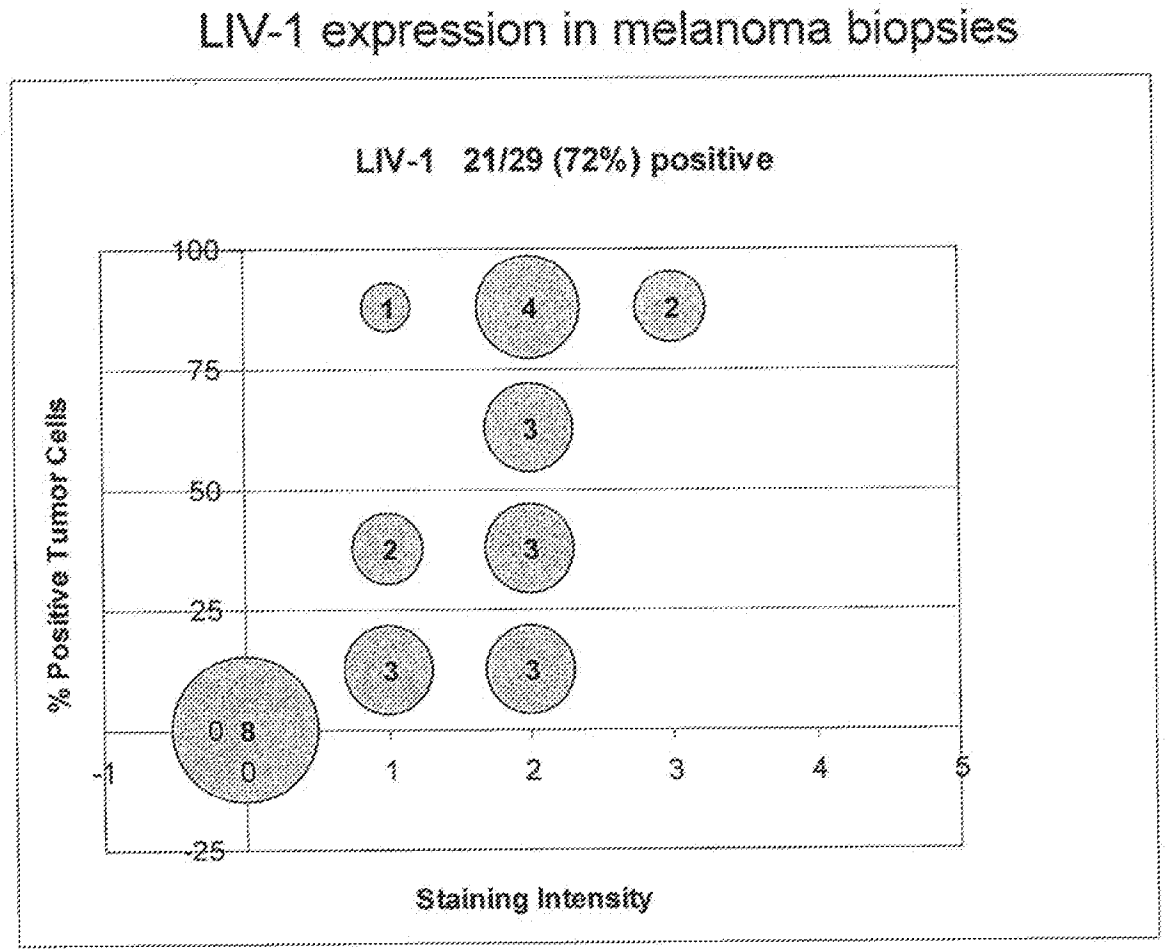
FIG. 28 shows an analysis of LIV-1 protein expression by IHC on melanoma cancer patient samples.

Results are shown in FIG. 28. Seventy-two percent of the tested melanoma patient samples (21/29) were positive for LIV-1 expression. This indicates that LIV-1 inhibitors, e.g., anti-LIV-1antibodies, can be used to treat melanoma cancers.

In Vivo Anti-melanoma Activity of LIV-1 ADC

Nude (nu/nu) mice (7-8 animals/group) are implanted with $10\times10^6$ SK-MEL-5 cells (a melanoma tumor-derived cell line) grown in culture. Tumors are allowed to grow in vivo until they are 100 $mm^3$, as measured using a caliper. Humanized LIV-1 ADCs, e.g., hLIV14 or hLIV22, are administered at 3 mg/kg. Drug conjugates are, e.g., vcM-MAE or mcMMAF. Control ADC's are also administered to control animals at 3 mg/kg. ADC's are given as q4d×4 intraperitoneal injections. Tumor volumes are monitored using calipers and animals are euthanized when tumor volume reaches ~800 $mm^3$. Administration of hLIV14 ADC or hLIV22 ADC greatly reduced tumor growth in animals as compared to those animals that received control ADC's.

Sequence listing

<LIV-1 mAb light chain leader; PRT/1; *mus musculus*>
SEQ ID NO: 1
MKLPVRLLVLMFWIPVSTS <LIV-1 mAb heavy chain leader; PRT/1; *mus musculus*>
SEQ ID NO: 2
MKCSWVIFFLMAVVLGINS <replacement heavy chain leader sequence; PRT/1; *mus musculus*>
SEQ ID NO: 3
MAWVWTLLFLMAAAQSAQA <Light chain constant region; PRT/1; *homo sapiens*>
SEQ ID NO: 4
TVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVT
KSFNRGEC <CH1—CH3; PRT/1; *homo sapiens*>
SEQ ID NO: 5
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK <heavy chain CH1—CH3 (no c-term K); PRT/1; *homo sapiens*>
SEQ ID NO: 6
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG <S239C heavy chain CH1—CH3; PRT/1; *homo sapiens*>
SEQ ID NO: 7
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPCVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK <S239C heavy chain CH1—CH3 (no c-term K); PRT/1; *homo sapiens*>
SEQ ID NO: 8
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPCVFLFPPKPKDTLMISRTPEVTCVVV -continued Sequence listing DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG <hLIV-1 mAb HA; PRT/1; artificial>
SEQ ID NO: 9
QVQLVQSGAEVKKPGASVKVSCKASGYTFTDYYMHWVRQAPGQGLEWMG
WIDPENGDTEYAPTFQGRVTMTRDTSISTAYMELSRLRSDDTAVYYCAR
HDAHYGTWFAYWGQGTLVTVSS <hLIV-1 mAb HB; PRT/1; artificial>
SEQ ID NO: 10
QVQLVQSGAEVKKPGASVKVSCKASGYTIEDYYMHWVRQAPGQGLEWMG
WIDPENGDTEYAPTFQGRVTMTRDTSINTAYMELSRLRSDDTAVYYCAR
HDAHYGTWFAYWGQGTLVTVSS <hLIV-1 mAb HC; PRT/1; artificial>
SEQ ID NO: 11
QVQLVQSGAEVKKPGASVKVSCKASGYTFTDYYMHWVRQAPGQGLEWMG
WIDPENGDTEYAPTFQGKATMTADTSISTAYMELSRLRSDDTAVYYCAR
HDAHYGTWFAYWGQGTLVTVSS <hLIV-1 mAb HD; PRT/1; artificial>
SEQ ID NO: 12
QVQLVQSGAEVKKPGASVKVSCKASGFTFTDYYMHWVRQAPGQGLEWMG
WIDPENGDTEYAPTFQGRVTMTRDTSISTAYMELSRLRSDDTAVYYCNV
HDAHYGTWFAYWGQGTLVTVSS <hLIV-1 mAb HE; PRT/1; artificial>
SEQ ID NO: 13
QVQLVQSGAEVKKPGASVKVSCKASGFNIEDYYMHWVRQAPGQGLEWIG
WIDPENGDTEYAPTFQGKATMTADTSINTAYMELSRLRSDDTAVYYCNV
HDAHYGTWFAYWGQGTLVTVSS <hLIV-1 mAb LA; PRT/1; artificial>
SEQ ID NO: 14
DVVMTQSPLSLPVTLGQPASISCRSSQSIIRNDGNTYLEWFQQRPGQSP
RRLIYRVSNRFSGVPDRFSGSGSGTDFTLKISRVEAEDVGVYYCFQGSH
VPYTFGGGTKVEIKR <hLIV-1 mAb LB; PRT/1; artificial>
SEQ ID NO: 15
DVVMTQSPLSLPVTLGQPASISCRSSQSIIRNDGNTYLEWYQQRPGQSP
RRLIYRVSNRFSGVPDRFSGSGSGTDFTLKISRVEAEDVGVYYCFQGSH
VPYTFGGGTKVEIKR <hLIV-1 mAb LC; PRT/1; artificial>
SEQ ID NO: 16
DVVMTQSPLSLPVTLGQPASISCRSSQSIIRNDGNTYLEWFLQRPGQSP
RRLIYRVSNRFSGVPDRFSGSGSGTDFTLKISRVEAEDVGVYYCFQGSH
VPYTFGGGTKVEIKR <hLIV-1 mAb LD; PRT/1; artificial>
SEQ ID NO: 17
DVVMTQSPLSLPVTLGQPASISCRSSQSIIRNDGNTYLEWFQQRPGQSP
KRLIYRVSNRFSGVPDRFSGSGSGTDFTLKISRVEAEDVGVYYCFQGSH
VPYTFGGGTKVEIKR <hLIV-1 mAb LE; PRT/1; artificial>
SEQ ID NO: 18
DVVMTQSPLSLPVTLGQPASISCRSSQSIIRNDGNTYLEWFQQRPGQSP
RLLIYRVSNRFSGVPDRFSGSGSGTDFTLKISRVEAEDVGVYYCFQGSH
VPYTFGGGTKVEIKR <hLIV-1 mAb LF; PRT/1; artificial>
SEQ ID NO: 19
DVVMTQSPLSLPVTLGQPASISCRSSQSIIRNDGNTYLEWYLQKPGQSP
KLLIYRVSNRFSGVPDRFSGSGSGTDFTLKISRVEAEDVGVYYCFQGSH
VPYTFGGGTKVEIKR DNA sequences:
<LIV-1 mAb heavy chain leader; DNA; *mus musculus*>
SEQ ID NO: 20
atgaaatgcagctgggtcatcttcttcctgatggcagtggttctaggaa
tcaattca Sequence listing <LIV-1 mAb light chain leader; DNA; *mus musculus*>
SEQ ID NO: 21
atgaagttgcctgttaggctgttggtgctgatgttctggattcctgttt
ctaccagt >replacement heavy chain leader sequence; DNA; *mus musculus*>
SEQ ID NO: 22
atggcttgggtgtggaccttgctattcctgatggcagctgcccaaagtg
cccaagca >light chain constant region; DNA; *mus musculus*>
SEQ ID NO: 23
acggtggctgcaccatctgtcttcatcttcccgccatctgatgagcagt
tgaaatctggaactgcctctgttgtgtgcctgctgaataacttctatcc
cagagaggccaaagtacagtggaaggtggataacgccctccaatcgggt
aactcccaggagagtgtcacagagcaggacagcaaggacagcacctaca
gcctcagcagcaccctgacgctgagcaaagcagactacgagaaacacaa
agtctacgcctgcgaagtcacccatcagggcctgagctcgcccgtcaca
aagagcttcaacaggggagagtgt <CH1—CH3; DNA; *homo sapiens*>
SEQ ID NO: 24
gctagcaccaagggcccatctgtcttccccctggcaccctcctccaaga
gcacctctgggggcacagctgccctgggctgcctggtcaaggactactt
ccctgaacctgtgacagtgtcctggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt
gagcccaaatcttgtgacaaaactcacacatgcccaccgtgcccagcac
ctgaactcctgggggaccgtcagtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggatgagctgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacacagaagagcctctccctgtc
tccgggtaaa <CH1—CH3 (w/o c-term K); DNA; *homo sapiens*>
SEQ ID NO: 25
gctagcaccaagggcccatctgtcttccccctggcaccctcctccaaga
gcacctctgggggcacagctgccctgggctgcctggtcaaggactactt
ccctgaacctgtgacagtgtcctggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt
gagcccaaatcttgtgacaaaactcacacatgcccaccgtgcccagcac
ctgaactcctgggggaccgtcagtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggatgagctgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacacagaagagcctctccctgtc
tccgggt <S239C CH1—CH3; DNA; artificial>
SEQ ID NO: 26
gctagcaccaagggcccatctgtcttccccctggcaccctcctccaaga
gcacctctgggggcacagctgccctgggctgcctggtcaaggactactt
ccctgaacctgtgacagtgtcctggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt
gagcccaaatcttgtgacaaaactcacacatgcccaccgtgcccagcac
ctgaactcctgggggaccgtgtgtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggatgagctgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacacagaagagcctctccctgtc
tccgggt <S239C CH1—CH3 (w/o c-term K); DNA; artificial>
SEQ ID NO: 27
gctagcaccaagggcccatctgtcttccccctggcaccctcctccaaga
gcacctctgggggcacagctgccctgggctgcctggtcaaggactactt
ccctgaacctgtgacagtgtcctggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt
gagcccaaatcttgtgacaaaactcacacatgcccaccgtgcccagcac
ctgaactcctgggggaccgtgtgtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggatgagctgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacacagaagagcctctccctgtc
tccgggt <hLIV-1 mAb HA; DNA; artificial>
SEQ ID NO: 28
caggtgcagctggtgcagtctggggctgaggtgaagaagcctggggcct
cagtgaaggtctcctgcaaggcttctggatacaccttcacagactacta
tatgcactgggtgaggcaggcccctggacaagggcttgagtggatggga
tggattgatcctgagaatggtgatactgaatatgcccccaccttccagg
gcagggtcaccatgaccagggacacctccatcagcacagcctacatgga
gctgagcaggctgagatctgatgacacagctgtgtattactgtgccaga
catgatgctcactatgggacctggtttgcttactggggccaaggaaccc
tggtcacagtctcctca <hLIV-1 mAb HB; DNA; artificial>
SEQ ID NO: 29
caggtgcagctggtgcagtctggggctgaggtgaagaagcctggggcct
cagtgaaggtctcctgcaaggcttctggatacaccattgaagactacta
tatgcactgggtgaggcaggcccctggacaagggcttgagtggatggga
tggattgatcctgagaatggtgatactgaatatgcccccaccttccagg
gcagggtcaccatgaccagggacacctccatcaacacagcctacatgga
gctgagcaggctgagatctgatgacacagctgtgtattactgtgccaga
catgatgctcactatgggacctggtttgcttactggggccaaggaaccc
tggtcacagtctcctca <hLIV-1 mAb; DNA; artificial>
SEQ ID NO: 30
caggtgcagctggtgcagtctggggctgaggtgaagaagcctggggcct
cagtgaaggtctcctgcaaggcttctggatacaccttcacagactacta
tatgcactgggtgaggcaggcccctggacaagggcttgagtggatggga
tggattgatcctgagaatggtgatactgaatatgcccccaccttccagg
gcaaggccactatgactgcagacacctccatcagcacagcctacatgga
gctgagcaggctgagatctgatgacacagctgtgtattactgtgccaga
catgatgctcactatgggacctggtttgcttactggggccaaggaaccc
tggtcacagtctcctca <hLIV-1 mAb HD; DNA; artificial>
SEQ ID NO: 31
caggtgcagctggtgcagtctggggctgaggtgaagaagcctggggcct
cagtgaaggtctcctgcaaggcttctggattcaccttcacagactacta Sequence listing tatgcactgggtgaggcaggcccctggacaagggcttgagtggatggga
tggattgatcctgagaatggtgatactgaatatgcccccaccttccagg
gcagggtcaccatgaccagggacacctccatcagcacagcctacatgga
gctgagcaggctgagatctgatgacacagctgtgtattactgtgccaga
catgatgctcactatgggacctggtttgcttactggggccaaggaaccc
tggtcacagtctcctca <hLIV-1 mAb HE; DNA; artificial>
SEQ ID NO: 32
Caggtgcagctggtgcagtctggggctgaggtgaagaagcctggggcct
cagtgaaggtctcctgcaaggcttctggattcaacattgaagactacta
tatgcactgggtgaggcaggcccctggacaagggcttgagtggattgga
tggattgatcctgagaatggtgatactgaatatgcccccaccttccagg
gcaaggccactatgactgcagacacctccatcaacacagcctacatgga
gctgagcaggctgagatctgatgacacagctgtgtattactgtaatgtc
catgatgctcactatgggacctggtttgcttactggggccaaggaaccc
tggtcacagtctcctca <hLIV-1 mAb LA; DNA; artificial>
SEQ ID NO: 33
gatgttgtgatgactcagtctccactctccctgcctgtcacccttggac
agcctgcctccatctcctgcagatctagtcagagcattataaggaatga
tggaaacacctatttggaatggtttcagcagaggccaggccaatctcca
aggaggctaatttatagagtttccaacaggttttctggggtcccagaca
gattctctggcagtgggtcaggcactgatttcacactgaaaatcagcag
ggtggaggctgaggatgttggggtttattactgctttcaaggttcacat
gttccctacacctttggaggagggaccaaggtggagatcaaacgt <hLIV-1 mAb LB; DNA; artificial>
SEQ ID NO: 34
gatgttgtgatgactcagtctccactctccctgcctgtcacccttggac
agcctgcctccatctcctgcagatctagtcagagcattataaggaatga
tggaaacacctatttggaatggtaccagcagaggccaggccaatctcca
aggaggctaatttatagagtttccaacaggttttctggggtcccagaca
gattctctggcagtgggtcaggcactgatttcacactgaaaatcagcag
ggtggaggctgaggatgttggggtttattactgctttcaaggttcacat
gttccctacacctttggaggagggaccaaggtggagatcaaacgt <hLIV-1 mAb LC; DNA; artificial>
SEQ ID NO: 35
gatgttgtgatgactcagtctccactctccctgcctgtcacccttggac
agcctgcctccatctcctgcagatctagtcagagcattataaggaatga
tggaaacacctatttggaatggtttctgcagaggccaggccaatctcca
aggaggctaatttatagagtttccaacaggttttctggggtcccagaca
gattctctggcagtgggtcaggcactgatttcacactgaaaatcagcag
ggtggaggctgaggatgttggggtttattactgctttcaaggttcacat
gttccctacacctttggaggagggaccaaggtggagatcaaacgt <hLIV-1 mAb LD; DNA; artificial>
SEQ ID NO: 36
gatgttgtgatgactcagtctccactctccctgcctgtcacccttggac
agcctgcctccatctcctgcagatctagtcagagcattataaggaatga
tggaaacacctatttggaatggtttcagcagaggccaggccaatctcca
aagaggctaatttatagagtttccaacaggttttctggggtcccagaca
gattctctggcagtgggtcaggcactgatttcacactgaaaatcagcag
ggtggaggctgaggatgttggggtttattactgctttcaaggttcacat
gttccctacacctttggaggagggaccaaggtggagatcaaacgt <hLIV-1 mAb LE; DNA; artificial>
SEQ ID NO: 37
gatgttgtgatgactcagtctccactctccctgcctgtcacccttggaa
gccctgcctccatctcctgcagatctagtcagagcattataaggaatga
tggaaacacctatttggaatggtttcagcagaggccaggccaatctcca
aggctcctaatttatagagtttccaacaggttttctggggtcccagaca
gattctctggcagtgggtcaggcactgatttcacactgaaaatcagcag
ggtggaggctgaggatgttggggtttattactgctttcaaggttcacat
gttccctacacctttggaggagggaccaaggtggagatcaaacgt <hLIV-1 mAb LF; DNA; artificial>
SEQ ID NO: 38
gatgttgtgatgactcagtctccactctccctgcctgtcacccttggac
agcctgcctccatctcctgcagatctagtcagagcattataaggaatga
tggaaacacctatttggaatggtacctgcagaaaccaggccaatctcca
aagctcctaatttatagagtttccaacaggttttctggggtcccagaca
gattctctggcagtgggtcaggcactgatttcacactgaaaatcagcag
ggtggaggctgaggatgttggggtttattactgctttcaaggttcacat
gttccctacacctttggaggagggaccaaggtggagatcaaacgt <Liv1 mAb2 light chain leader; PRT/1; *mus musculus*>
SEQ ID NO: 39
MKLPVRLLVLMFWIPVATSS <Liv1 mAb2 heavy chain leader; PRT/1; *mus musculus*>
SEQ ID NO: 40
MKCSWVIFFLMAVVIGINS <replacement heavy chain leader sequence; PRT/1; *mus musculus*>
SEQ ID NO: 41
MAWVWTLLFLMAAAQSAQA <Light chain constant region; PRT/1; *homo sapiens*>
SEQ ID NO: 42
TVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVT
KSFNRGEC <CH1—CH3; PRT/1; *homo sapiens*>
SEQ ID NO: 43
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK*

<heavy chain CH1—CH3 (no c-term K); PRT/1; *homo sapiens*>
SEQ ID NO: 44
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG <S239C heavy chain CH1—CH3; PRT/1; *homo sapiens*>
SEQ ID NO: 45
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPCVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK <S239C heavy chain CH1—CH3 (no c-term K); PRT/1; homo sapiens>
SEQ ID NO: 46
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPCVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG <hLiv1 mAb2 HA; PRT/1; artificial>
SEQ ID NO: 47
QVQLVQSGAEVKKPGASVKVSCKASGYTFTDYYMHWVRQAPGQGLEWMG
WIDPENGDTEYGPKFQGRVTMTRDTSISTAYMELSRLRSDDTAVYYCAR
HNAHYGTWFAYWGQGTLVTVSS <hLiv1 mAb2 HB; PRT/1; artificial>
SEQ ID NO: 48
QVQLVQSGAEVKKPGASVKVSCKASGYTIEDYYMHWVRQAPGQGLEWMG
WIDPENGDTEYGPKFQGRVTMTRDTSINTAYMELSRLRSDDTAVYYCAR
HNAHYGTWFAYWGQGTLVTVSS Sequence listing <hLiv1 mAb2 HC; PRT/1; artificial>
SEQ ID NO: 49
QVQLVQSGAEVKKPGASVKVSCKASGYTFTDYYMHWVRQAPGQGLEWMG
WIDPENGDTEYGPKFQGKATMTADTSISTAYMELSRLRSDDTAVYYCAR
HNAHYGTWFAYWGQGTLVTVSS <hLiv1 mAb2 HD; PRT/1; artificial>
SEQ ID NO: 50
QVQLVQSGAEVKKPGASVKVSCKASGLTFTDYYMHWVRQAPGQGLEWMG
WIDPENGDTEYGPKFQGRVTMTRDTSISTAYMELSRLRSDDTAVYYCTV
HNAHYGTWFAYWGQGTLVTVSS <hLiv1 mAb2 HE; PRT/1; artificial>
SEQ ID NO: 51
QVQLVQSGAEVKKPGASVKVSCKASGLNIEDYYMHWVRQAPGQGLEWIG
WIDPENGDTEYGPKFQGKATMTADTSINTAYMELSRLRSDDTAVYYCTV
HNAHYGTWFAYWGQGTLVTVSS <hLiv1 mAb2 HF; PRT/1; artificial>
SEQ ID NO: 52
QVQLVQSGAEVKKPGASVKVSCKASGLTIEDYYMHWVRQAPGQGLEWMG
WIDPENGDTEYGPKFQGRVTMTRDTSISTAYMELSRLRSDDTAVYYCAV
HNAHYGTWFAYWGQGTLVTVSS <hLiv1 mAb2 HG; PRT/1; artificial>
SEQ ID NO: 53
QVQLVQSGAEVKKPGASVKVSCKASGLTIEDYYMHWVRQAPGQGLEWMG
WIDPENGDTEYGPKFQGRVTMTRDTSINTAYMELSRLRSDDTAVYYCAV
HNAHYGTWFAYWGQGTLVTVSS <hLiv1 mAb2 LA; PRT/1; artificial>
SEQ ID NO: 54
DVVMTQSPLSLPVTLGQPASISCRSSQSLLHSSGNTYLEWFQQRPGQSP
RRLIYKISTRFSGVPDRFSGSGSGTDFTLKISRVEAEDVGVYYCFQGSH
VPYTFGGGTKVEIKR <hLiv1 mAb2 LB; PRT/1; artificial>
SEQ ID NO: 55
DVVMTQSPLSLPVTLGQPASISCRSSQSLLHSSGNTYLEWYQQRPGQSP
RRLIYKISTRFSGVPDRFSGSGSGTDFTLKISRVEAEDVGVYYCFQGSH
VPYTFGGGTKVEIKR <hLiv1 mAb2 LC; PRT/1; artificial>
SEQ ID NO: 56
DVVMTQSPLSLPVTLGQPASISCRSSQSLLHSSGNTYLEWFLQRPGQSP
RRLIYKISTRFSGVPDRFSGSGSGTDFTLKISRVEAEDVGVYYCFQGSH
VPYTFGGGTKVEIKR <hLiv1 mAb2 LD; PRT/1; artificial>
SEQ ID NO: 57
DVVMTQSPLSLPVTLGQPASISCRSSQSLLHSSGNTYLEWFQQRPGQSP
KRLIYKISTRFSGVPDRFSGSGSGTDFTLKISRVEAEDVGVYYCFQGSH
VPYTFGGGTKVEIKR <hLiv1 mAb2 LE; PRT/1; artificial>
SEQ ID NO: 58
DVVMTQSPLSLPVTLGQPASISCRSSQSLLHSSGNTYLEWFQQRPGQSP
RPLIYKISTRFSGVPDRFSGSGSGTDFTLKISRVEAEDVGVYYCFQGSH
VPYTFGGGTKVEIKR <hLiv1 mAb2 LF; PRT/1; artificial>
SEQ ID NO: 59
DVVMTQSPLSLPVTLGQPASISCRSSQSLLHSSGNTYLEWYLQRPGQSP
KPLIYKISTRFSGVPDRFSGSGSGTDFTLKISRVEAEDVGVYYCFQGSH
VPYTFGGGTKVEIKR <hLiv1 mAb2 LG; PRT/1; artificial>
SEQ ID NO: 60
DVVMTQSPLSLPVTLGQPASISCRSSQSLLHSSGNTYLEWYQQRPGQSP
RPLIYKISTRFSGVPDRFSGSGSGTDFTLKISRVEAEDVGVYYCFQGSH
VPYTFGGGTKVEIKR DNA sequences:
<Liv1 mAb2 heavy chain leader; DNA; *mus musculus*>
SEQ ID NO: 61
atgaaatgcagctgggtcatcttcttcctgatggcagtggttataggaa
tcaattca <Liv1 mAb2 light chain leader; DNA; *mus musculus*>
SEQ ID NO: 62
atgaagttgcctgttaggctgttggtgctgatgttctggattcctgcta
ccagcagt <replacement heavy chain leader sequence; DNA; *mus musculus*>
SEQ ID NO: 63
atggcttgggtgtggaccttgctattcctgatggcagctgcccaaagtg
cccaagca <light chain constant region; DNA; *homo sapiens*>
SEQ ID NO: 64
acgacggtggctgcaccatctgtcttcatcttcccgccatctgatgagc
agttgaaatctggaactgcctctgttgtgtgcctgctgaataacttcta
tcccagagaggccaaagtacagtggaaggtggataacgccctccaatcg
ggtaactcccaggagagtgtcacagagcaggacagcaaggacagcacct
acagcctcagcagcaccctgacgctgagcaaagcagactacgagaaaca
caaagtctacgcctgcgaagtcacccatcagggcctgagctcgcccgtc
acaaagagcttcaacaggggagagtgttag <CH1-CH3; DNA; *homo sapiens*>
SEQ ID NO: 65
gctagcaccaagggcccatctgtcttccccctggcaccctcctccaaga
gcacctctgggggcacagctgccctgggctgcctggtcaaggactactt
ccctgaacctgtgacagtgtcctggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt
gagcccaaatcttgtgacaaaactcacacatgcccaccgtgcccagcac
ctgaactcctgggggggaccgtcagtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggatgagctgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacatcaagctcacc
gtggacaagagcaggtggcagcaggggaacgtcttctcatgctccgtga
tgcatgaggctctgcacaaccactacacacagaagagcctctccctgtc
tccgggtaaa <CH1—CH3 (w/o c-term K); DNA; *homo sapiens*>
SEQ ID NO: 66
gctagcaccaagggcccatctgtcttccccctggcaccctcctccaaga
gcacctctgggggcacagctgccctgggctgcctggtcaaggactactt
ccctgaacctgtgacagtgtcctggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt
gagcccaaatcttgtgacaaaactcacacatgcccaccgtgcccagcac
ctgaactcctgggggggaccgtcagtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggatgagctgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacacagaagagcctctccctgtc
tccgggt <S239C CH1—CH3; DNA; artificial>
SEQ ID NO: 67
gctagcaccaagggcccatctgtcttccccctggcaccctcctccaaga
gcacctctgggggcacagctgccctgggctgcctggtcaaggactactt
ccctgaacctgtgacagtgtcctggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt Sequence listing gagcccaaatcttgtgacaaaactcacacatgcccaccgtgcccagcac
ctgaactcctgggggaccgtgtgtcttcctcttcccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggatgagctgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacacagaagagcctctccctgtc
tccgggtaaa <S239C CH1—CH3 (w/o c-term K); DNA; artificial>
SEQ ID NO: 68 gctagcaccaagggcccatctgtcttcccccctggcaccctcctccaaga
gcacctctgggggcacagctgccctgggctgcctggtcaaggactactt
ccctgaacctgtgacagtgtcctggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt
gagcccaaatcttgtgacaaaactcacacatgcccaccgtgcccagcac
ctgaactcctgggggaccgtgtgtcttcctcttcccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggatgagctgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacacagaagagcctctccctgtc
tccgggt <hLiv1 mAb2 HA; DNA; artificial>
SEQ ID NO: 69 caggtgcagctggtgcagtctggggctgaggtgaagaagcctggggcct
cagtgaaggtctcctgcaaggcttctggatacaccttcacagactacta
tatgcactgggtgaggcaggcccctggacaagggcttgagtggatggga
tggattgatcctgaaaatggtgatactgaatatggcccgaagttccagg
gcagggtcaccatgaccagggacacctccatcagcacagcctacatgga
gctgagcaggctgagatctgatgacacagctgtgtattactgtgccaga
cataatgctcactacgggacctggtttgcttactggggccaaggaaccc
tggtcacagtctcctca <hLiv1 mAb2 HB; DNA; artificial>
SEQ ID NO: 70 caggtgcagctggtgcagtctggggctgaggtgaagaagcctggggcct
cagtgaaggtctcctgcaaggcttctggatacaccattgaagactacta
tatgcactgggtgaggcaggcccctggacaagggcttgagtggatggga
tggattgatcctgaaaatggtgatactgaatatggcccgaagttccagg
gcagggtcaccatgaccagggacacctccatcaacacagcctacatgga
gctgagcaggctgagatctgatgacacagctgtgtattactgtgccaga
cataatgctcactacgggacctggtttgcttactggggccaaggaaccc
tggtcacagtctcctca <hLiv1 mAb2 HC; DNA; artificial>
SEQ ID NO: 71 caggtgcagctggtgcagtctggggctgaggtgaagaagcctggggcct
cagtgaaggtctcctgcaaggcttctggatacaccttcacagactacta
tatgcactgggtgaggcaggcccctggacaagggcttgagtggatggga
tggattgatcctgaaaatggtgatactgaatatggcccgaagttccagg
gcaaggccaccatgaccgcagacacctccatcagcacagcctacatgga
gctgagcaggctgagatctgatgacacagctgtgtattactgtgccaga
cataatgctcactacgggacctggtttgcttactggggccaaggaaccc
tggtcacagtctcctca <Liv1 mAb2 HD; DNA; artificial>
SEQ ID NO: 72

Caggtgcagctggtgcagtctggggctgaggtgaagaagcctggggcct
cagtgaaggtctcctgcaaggcttctggactcaccttcacagactacta
tatgcactgggtgaggcaggcccctggacaagggcttgagtggatggga
tggattgatcctgaaaatggtgatactgaatatggcccgaagttccagg
gcagggtcaccatgaccagggacacctccatcagcacagcctacatgga
gctgagcaggctgagatctgatgacacagctgtgtattactgtactgtc
cataatgctcactacgggacctggtttgcttactggggccaaggaaccc
tggtcacagtctcctca <hLiv1 mAb2 HE; DNA; artificial>
SEQ ID NO: 73 caggtgcagctggtgcagtctggggctgaggtgaagaagcctggggcct
cagtgaaggtctcctgcaaggcttctggactcaacattgaagactacta
tatgcactgggtgaggcaggcccctggacaagggcttgagtggattgga
tggattgatcctgaaaatggtgatactgaatatggcccgaagttccagg
gcaaggccaccatgaccgcagacacctccatcaacacagcctacatgga
gctgagcaggctgagatctgatgacacagctgtgtattactgtactgtc
cataatgctcactacgggacctggtttgcttactggggccaaggaaccc
tggtcacagtctcctca <hLiv1 mAb2 HF; DNA; artificial>
SEQ ID NO: 74 caggtgcagctggtgcagtctggggctgaggtgaagaagcctggggcct
cagtgaaggtctcctgcaaggcttctggactcaccattgaagactacta
tatgcactgggtgaggcaggcccctggacaagggcttgagtggatggga
tggattgatcctgaaaatggtgatactgaatatggcccgaagttccagg
gcagggtcaccatgaccagggacacctccatcagcacagcctacatgga
gctgagcaggctgagatctgatgacacagctgtgtattactgtgccgtc
cataatgctcactacgggacctggtttgcttactggggccaaggaaccc
tggtcacagtctcctca <hLiv1 mAb2 HG; DNA; artificial>
SEQ ID NO: 75 caggtgcagctggtgcagtctggggctgaggtgaagaagcctggggcct
cagtgaaggtctcctgcaaggcttctggactcaccattgaagactacta
tatgcactgggtgaggcaggcccctggacaagggcttgagtggatggga
tggattgatcctgaaaatggtgatactgaatatggcccgaagttccagg
gcagggtcaccatgaccagggacacctccatcaacacagcctacatgga
gctgagcaggctgagatctgatgacacagctgtgtattactgtgccgtc
cataatgctcactacgggacctggtttgcttactggggccaaggaaccc
tggtcacagtctcctca <hLiv1 mAb2 LA; DNA; artificial>
SEQ ID NO: 76 gatgttctggattcctgctaccagcagtgatgttgtgatgactcagtct
ccactctccctgcctgtcacccttggacagcctgcctccatctcctgca
gatctagtcagagccttttacacagtagtggaaacacctatttagaatg
gtttcagcagaggccaggccaatctccaaggaggctaatttataaaatt
tccacccgattttctggggtcccagacagattctctggcagtgggtcag
gcactgatttcacactgaaaatcagcagggtggaggctgaggatgttgg
ggtttattactgctttcaaggttcacatgttccctacacctttggagga
gggaccaaggtggagatcaaacgtacg <hLiv1 mAb2 LB; DNA; artificial>
SEQ ID NO: 77 gatgttctggattcctgctaccagcagtgatgttgtgatgactcagtct
ccactctccctgcctgtcacccttggacagcctgcctccatctcctgca
gatctagtcagagccttttacacagtagtggaaacacctatttagaatg
gtaccagcagaggccaggccaatctccaaggaggctaatttataaaatt
tccacccgattttctggggtcccagacagattctctggcagtgggtcag
gcactgatttcacactgaaaatcagcagggtggaggctgaggatgttgg
ggtttattactgctttcaaggttcacatgttccctacacctttggagga
gggaccaaggtggagatcaaacgtacg <hLiv1 mAb2 LC; DNA; artificial>
SEQ ID NO: 78 gatgttctggattcctgctaccagcagtgatgttgtgatgactcagtct
ccactctccctgcctgtcacccttggacagcctgcctccatctcctgca
gatctagtcagagccttttacacagtagtggaaacacctatttagaatg
gtttctgcagaggccaggccaatctccaaggaggctaatttataaaatt
tccacccgattttctggggtcccagacagattctctggcagtgggtcag
gcactgatttcacactgaaaatcagcagggtggaggctgaggatgttgg
ggtttattactgctttcaaggttcacatgttccctacacctttggagga
gggaccaaggtggagatcaaacgtacg <hLiv1 mAb2 LD; DNA; artificial>
SEQ ID NO: 79 gatgttctggattcctgctaccagcagtgatgttgtgatgactcagtct
ccactctccctgcctgtcacccttggacagcctgcctccatctcctgca -continued Sequence listing

```
gatctagtcagagccttttacacagtagtggaaacacctatttagaatg
gtttcagcagaggccaggccaatctccaaagaggctaatttataaaatt
tccacccgattttctggggtcccagacagattctctggcagtgggtcag
gcactgatttcacactgaaaatcagcagggtggaggctgaggatgttgg
ggtttattactgctttcaaggttcacatgttccctacacctttggagga
gggaccaaggtggagatcaaacgtacg

<hLiv1 mAb2 LE; DNA; artificial>
                                        SEQ ID NO: 80
gatgttctggattcctgctaccagcagtgatgttgtgatgactcagtct
ccactctccctgcctgtcacccttggacagcctgcctccatctcctgca
gatctagtcagagccttttacacagtagtggaaacacctatttagaatg
gtttcagcagaggccaggccaatctccaaggcccctaatttataaaatt
tccacccgattttctggggtcccagacagattctctggcagtgggtcag
gcactgatttcacactgaaaatcagcagggtggaggctgaggatgttgg
ggtttattactgctttcaaggttcacatgttccctacacctttggagga
gggaccaaggtggagatcaaacgtacg

<Liv1 mAb2 LF; DNA; artificial>
                                        SEQ ID NO: 81
gatgttgtgatgactcagtctccactctccctgcctgtcacccttggac
agcctgcctccatctcctgcagatctagtcagagccttttacacagtag
tggaaacacctatttagaatggtacctgcagaggccaggccaatctcca
aagcccctaatttataaaatttccacccgattttctggggtcccagaca
gattctctggcagtgggtcaggcactgatttcacactgaaaatcagcag
ggtggaggctgaggatgttggggtttattactgctttcaaggttcacat
gttccctacacctttggaggagggaccaaggtggagatcaaacgt

<hLiv1 BR2-22a LG; DNA; artificial>
                                        SEQ ID NO: 82
gatgttgtgatgactcagtctccactctccctgcctgtcacccttggac
agcctgcctccatctcctgcagatctagtcagagccttttacacagtag
tggaaacacctatttagaatggtaccagcagaggccaggccaatctcca
aggcccctaatttataaaatttccacccgattttctggggtcccagaca
gattctctggcagtgggtcaggcactgatttcacactgaaaatcagcag
ggtggaggctgaggatgttggggtttattactgctttcaaggttcacat
gttccctacacctttggaggagggaccaaggtggagatcaaacgt

<Q13433; protein
                                        SEQ ID NO: 83
MARKLSVILI LTFALSVTNP LHELKAAAFP QTTEKISPNW
ESGINVDLAI STRQYHLQQL FYRYGENNSL SVEGFRKLLQ
NIGIDKIKRI HIHHDHDHHS DHEHHSDHER HSDHEHHSEH
EHHSDHDHHS HHNHAASGKN KRKALCPDHD SDSSGKDPRN
SQGKGAHRPE HASGRRNVKD SVSASEVTST VYNTVSEGTH
FLETIETPRP GKLFPKDVSS STPPSVTSKS RVSRLAGRKT
NESVSEPRKG FMYSRNTNEN PQECFNASKL LTSHGMGIQV
PLNATEFNYL CPAIINQIDA RSCLIHTSEK KAEIPPKTYS
LQIAWVGGFI AISIISFLSL LGVILVPLMN RVFFKFLLSF
LVALAVGTLS GDAFLHLLPH SHASHHHSHS HEEPAMEMKR
GPLFSHLSSQ NIEESAYFDS TWKGLTALGG LYFMFLVEHV
LTLIKQFKDK KKKNQKKPEN DDDVEIKKQL SKYESQLSTN
EEKVDTDDRT EGYLRADSQE PSHFDSQQPA VLEEEEVMIA
HAHPQEVYNE YVPRGCKNKC HSHFHDTLGQ SDDLIHHHHD
YHHILHHHHH QNHHPHSHSQ RYSREELKDA GVATLAWMVI
MGDGLHNFSD GLAIGAAFTE GLSSGLSTSV AVFCHELPHE
LGDFAVLLKA GMTVKQAVLY NALSAMLAYL GMATGIFIGH
YAENVSMWIF ALTAGLFMYV ALVDMVPEML HNDASDHGCS
RWGYFFLQNA GMLLGFGIML LISIFEHKIV FRINF

<AAA96258.2; protein
                                        SEQ ID No: 84
MARKLSVILI LTFALSVTNP LHELKAAAFP QTTEKISPNW
ESGINVDLAI STRQYHLQQL FYRYGENNSL SVEGFRKLLQ
NIGIDKIKRI HIHHDHDHHS DHEHHSDHER HSDHEHHSDH
EHHSDHNHAA SGKNKRKALC PDHDSDSSGK DPRNSQGKGA
HRPEHASGRR NVKDSVSASE VTSTVYNTVS EGTHFLETIE
TPRPGKLFPK DVSSSTPPSV TSKSRVSRLA GRKTNESVSE
PRKGFMYSRN TNENPQECFN ASKLLTSHGM GIQVPLNATE
FNYLCPAIIN QIDARSCLIH TSEKKAEIPP KTYSLQIAWV
GGFIAISIIS FLSLLGVILV PLMNRVFFKF LLSFLVALAV
GTLSGDAFLH LLPHSHASHH HSHSHEEPAM EMKRGPLFSH
LSSQNIEESA YFDSTWKGLT ALGGLYFMFL VEHVLTLIKQ
FKDKKKKNQK KPENDDDVEI KKQLSKYESQ LSTNEEKVDT
DDRTEGYLRA DSQEPSHFDS QQPAVLEEEE VMIAHAHPQE
VYNEYVPRGC KNKCHSHFHD TLGQSDDLIH HHHDYHHILH
HHHHQNHHPH SHSQRYSREE LKDAGVATLA WMVIMGDGLH
NFSDGLAIGA AFTEGLSSGL STSVAVFCHE LPHELGDFAV
LLKAGMTVKQ AVLYNALSAM LAYLGMATGI FIGHYAENVS
MWIFALTAGL FMYVALVDMV PEMLHNDASD HGCSRWGYFF
LQNAGMLLGF GIMLLISIFE HKIVFRINF

<Cyno LIV-1
                                        SEQ ID NO: 85
MARKLSVILILTFTLSVTNPLHELKSAAAFPQTTEKISPNWESGINVDL
AITTRQYHLQQLFYRYGENNSLSVEGFRKLLQNIGIDKIKRIHIHHDHD
HHSDHEHHSDHEHHSDHEHHSHRNHAASGKNKRKALCPEHDSDSSGKDP
RNSQGKGAHRPEHANGRRNVKDSVSTSEVTSTVYNTVSEGTHFLETIET
PKLFPKDVSSSTPPSVTEKSLVSRLAGRKTNESMSEPRKGFMYSRNTNE
NPQECFNASKLLTSHGMGIQVPLNATEFNYLCPAIINQIDARSCLIHTS
EKKAEIPPKTYSLQIAWVGGFIAISIISFLSLLGVILVPLMNRVFFKFL
LSFLVALAVGTLSGDAFLHLLPHSHASHHHSHSHEEPAMEMKRGPLFSH
LSSQNIEESAYFDSTWKGLTALGGLYFMFLVEHVLTLIKQFKDKKKKNQ
KKPENDDDVEIKKQLSKYESQLSTNEEKVDTDDRTEGYLRADSQEPSHF
DSQQPAILEEEEVMIAHAHPQEVYNEYVPRGCKNKCHSHFHDTLGQSDD
LIHHHHDYHHILHHHHHQNHHPHSHSQRYSREELKDAGIATLAWMVIMG
DGLHNFSDGLAIGAAFTEGLSSGLSTSVAVFCHELPHELGDFAVLLKAG
MTVKQAVLYNALSAMLAYLGMATGIFIGHYAENVSMWIFALTAGLFMYV
ALVDMVPEMLHNDASDHGCSRWGYFFLQNAGMLLGFGIMLLISIFEHKI
VFRINF
```

SEQUENCE LISTING

```
<160> NUMBER OF SEQ ID NOS: 90

<210> SEQ ID NO 1
<211> LENGTH: 19
<212> TYPE: PRT
<213> ORGANISM: Homo sapiens

<400> SEQUENCE: 1

Met Lys Leu Pro Val Arg Leu Leu Val Leu Met Phe Trp Ile Pro Val
1               5                   10                  15

Ser Thr Ser


<210> SEQ ID NO 2
<211> LENGTH: 19
<212> TYPE: PRT
<213> ORGANISM: Mus musculus
```

<400> SEQUENCE: 2

Met Lys Cys Ser Trp Val Ile Phe Phe Leu Met Ala Val Val Leu Gly
1 5 10 15

Ile Asn Ser

<210> SEQ ID NO 3
<211> LENGTH: 19
<212> TYPE: PRT
<213> ORGANISM: Mus musculus

<400> SEQUENCE: 3

Met Ala Trp Val Trp Thr Leu Leu Phe Leu Met Ala Ala Ala Gln Ser
1 5 10 15

Ala Gln Ala

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 5
<211> LENGTH: 330
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 6
<211> LENGTH: 329
<212> TYPE: PRT
<213> ORGANISM: Homo sapiens

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 7
<211> LENGTH: 330
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 8
<211> LENGTH: 329
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 9
<211> LENGTH: 120
<212> TYPE: PRT
<213> ORGANISM: Artificial Sequence
<220> FEATURE:
<223> OTHER INFORMATION: Synthesized

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Thr Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg His Asp Ala His Tyr Gly Thr Trp Phe Ala Tyr Trp Gly Gln
            100                 105                 110

Gly Thr Leu Val Thr Val Ser Ser
        115                 120


<210> SEQ ID NO 10
<211> LENGTH: 120
<212> TYPE: PRT
<213> ORGANISM: Artificial Sequence
<220> FEATURE:
<223> OTHER INFORMATION: Synthesized

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Thr Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg His Asp Ala His Tyr Gly Thr Trp Phe Ala Tyr Trp Gly Gln
            100                 105                 110

Gly Thr Leu Val Thr Val Ser Ser
        115                 120


<210> SEQ ID NO 11
<211> LENGTH: 120
<212> TYPE: PRT
<213> ORGANISM: Artificial Sequence
<220> FEATURE:
<223> OTHER INFORMATION: Synthesized

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Thr Phe
    50                  55                  60

Gln Gly Lys Ala Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg His Asp Ala His Tyr Gly Thr Trp Phe Ala Tyr Trp Gly Gln
            100                 105                 110

Gly Thr Leu Val Thr Val Ser Ser
        115                 120


<210> SEQ ID NO 12
<211> LENGTH: 120
<212> TYPE: PRT
<213> ORGANISM: Artificial Sequence
<220> FEATURE:
<223> OTHER INFORMATION: Synthesized

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Thr Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Asn Val His Asp Ala His Tyr Gly Thr Trp Phe Ala Tyr Trp Gly Gln
            100                 105                 110

Gly Thr Leu Val Thr Val Ser Ser
        115                 120


<210> SEQ ID NO 13
<211> LENGTH: 120
<212> TYPE: PRT
<213> ORGANISM: Artificial Sequence
```

<220> FEATURE:
<223> OTHER INFORMATION: Synthesized

<400> SEQUENCE: 13

Gln Val Gln Leu Val Gln Ser Gly Ala Glu Val Lys Lys Pro Gly Ala
1 5 10 15

Ser Val Lys Val Ser Cys Lys Ala Ser Gly Phe Asn Ile Glu Asp Tyr
20 25 30

Tyr Met His Trp Val Arg Gln Ala Pro Gly Gln Gly Leu Glu Trp Ile
35 40 45

Gly Trp Ile Asp Pro Glu Asn Gly Asp Thr Glu Tyr Ala Pro Thr Phe
50 55 60

Gln Gly Lys Ala Thr Met Thr Ala Asp Thr Ser Ile Asn Thr Ala Tyr
65 70 75 80

Met Glu Leu Ser Arg Leu Arg Ser Asp Asp Thr Ala Val Tyr Tyr Cys
85 90 95

Asn Val His Asp Ala His Tyr Gly Thr Trp Phe Ala Tyr Trp Gly Gln
100 105 110

Gly Thr Leu Val Thr Val Ser Ser
115 120

<210> SEQ ID NO 14
<211> LENGTH: 113
<212> TYPE: PRT
<213> ORGANISM: Artificial Sequence
<220> FEATURE:
<223> OTHER INFORMATION: Synthesized

<400> SEQUENCE: 14

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Ile Ile Arg Asn
20 25 30

Asp Gly Asn Thr Tyr Leu Glu Trp Phe Gln Gln Arg Pro Gly Gln Ser
35 40 45

Pro Arg Arg Leu Ile Tyr Arg Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Tyr Thr Phe Gly Gly Gly Thr Lys Val Glu Ile Lys
100 105 110

Arg

<210> SEQ ID NO 15
<211> LENGTH: 113
<212> TYPE: PRT
<213> ORGANISM: Artificial Sequence
<220> FEATURE:
<223> OTHER INFORMATION: Synthesized

<400> SEQUENCE: 15

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Ile Ile Arg Asn
20 25 30

```
Asp Gly Asn Thr Tyr Leu Glu Trp Tyr Gln Gln Arg Pro Gly Gln Ser
        35                  40                  45

Pro Arg Arg Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg


<210> SEQ ID NO 16
<211> LENGTH: 113
<212> TYPE: PRT
<213> ORGANISM: Artificial Sequence
<220> FEATURE:
<223> OTHER INFORMATION: Synthesized

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Ile Arg Asn
            20                  25                  30

Asp Gly Asn Thr Tyr Leu Glu Trp Phe Leu Gln Arg Pro Gly Gln Ser
        35                  40                  45

Pro Arg Arg Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg


<210> SEQ ID NO 17
<211> LENGTH: 113
<212> TYPE: PRT
<213> ORGANISM: Artificial Sequence
<220> FEATURE:
<223> OTHER INFORMATION: Synthesized

<400> SEQUENCE: 17

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Ile Arg Asn
            20                  25                  30

Asp Gly Asn Thr Tyr Leu Glu Trp Phe Gln Gln Arg Pro Gly Gln Ser
        35                  40                  45

Pro Lys Arg Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95
```

```
Ser His Val Pro Tyr Thr Phe Gly Gly Gly Thr Lys Val Glu Ile Lys
            100                 105                 110

Arg


<210> SEQ ID NO 18
<211> LENGTH: 113
<212> TYPE: PRT
<213> ORGANISM: Artificial Sequence
<220> FEATURE:
<223> OTHER INFORMATION: Synthesized

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Ile Arg Asn
            20                  25                  30

Asp Gly Asn Thr Tyr Leu Glu Trp Phe Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg


<210> SEQ ID NO 19
<211> LENGTH: 113
<212> TYPE: PRT
<213> ORGANISM: Artificial Sequence
<220> FEATURE:
<223> OTHER INFORMATION: Synthesized

<400> SEQUENCE: 19

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Ile Arg Asn
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg


<210> SEQ ID NO 20
<211> LENGTH: 57
<212> TYPE: DNA
<213> ORGANISM: Mus musculus
```

<400> SEQUENCE: 20 atgaaatgca gctgggtcat cttcttcctg atggcagtgg ttctaggaat caattca 57

<210> SEQ ID NO 21
<211> LENGTH: 57
<212> TYPE: DNA
<213> ORGANISM: Mus musculus

<400> SEQUENCE: 21 atgaagttgc ctgttaggct gttggtgctg atgttctgga ttcctgtttc taccagt 57

<210> SEQ ID NO 22
<211> LENGTH: 57
<212> TYPE: DNA
<213> ORGANISM: Mus musculus

<400> SEQUENCE: 22 atggcttggg tgtggacctt gctattcctg atggcagctg cccaaagtgc ccaagca 57

<210> SEQ ID NO 23
<211> LENGTH: 318
<212> TYPE: DNA
<213> ORGANISM: Mus musculus

<400> SEQUENCE: 23 acggtggctg caccatctgt cttcatcttc ccgccatctg atgagcagtt gaaatctgga 60 actgcctctg ttgtgtgcct gctgaataac ttctatccca gagaggccaa agtacagtgg 120 aaggtggata acgccctcca atcgggtaac tcccaggaga gtgtcacaga gcaggacagc 180 aaggacagca cctacagcct cagcagcacc ctgacgctga gcaaagcaga ctacgagaaa 240 cacaaagtct acgcctgcga agtcacccat cagggcctga gctcgcccgt cacaaagagc 300 ttcaacaggg gagagtgt 318

<210> SEQ ID NO 24
<211> LENGTH: 990
<212> TYPE: DNA
<213> ORGANISM: Homo sapiens

<400> SEQUENCE: 24 gctagcacca agggcccatc tgtcttcccc ctggcaccct cctccaagag cacctctggg 60 ggcacagctg ccctgggctg cctggtcaag gactacttcc ctgaacctgt gacagtgtcc 120 tggaactcag gcgccctgac cagcggcgtg cacaccttcc cggctgtcct acagtcctca 180 ggactctact ccctcagcag cgtggtgacc gtgccctcca gcagcttggg cacccagacc 240 tacatctgca acgtgaatca caagcccagc aacaccaagg tggacaagaa agttgagccc 300 aaatcttgtg acaaaactca cacatgccca ccgtgcccag cacctgaact cctgggggga 360 ccgtcagtct tcctcttccc cccaaaaccc aaggacaccc tcatgatctc ccggacccct 420 gaggtcacat gcgtggtggt ggacgtgagc cacgaagacc ctgaggtcaa gttcaactgg 480 tacgtggacg gcgtggaggt gcataatgcc aagacaaagc cgcgggagga gcagtacaac 540 agcacgtacc gtgtggtcag cgtcctcacc gtcctgcacc aggactggct gaatggcaag 600 gagtacaagt gcaaggtctc caacaaagcc ctcccagccc ccatcgagaa aaccatctcc 660 aaagccaaag ggcagccccg agaaccacag gtgtacaccc tgcccccatc ccgggatgag 720 ctgaccaaga accaggtcag cctgacctgc ctggtcaaag gcttctatcc cagcgacatc 780 gccgtggagt gggagagcaa tgggcagccg gagaacaact acaagaccac gcctcccgtg 840

```
ctggactccg acggctcctt cttcctctac agcaagctca ccgtggacaa gagcaggtgg    900

cagcagggga acgtcttctc atgctccgtg atgcatgagg ctctgcacaa ccactacaca    960

cagaagagcc tctccctgtc tccgggtaaa                                     990
```

<210> SEQ ID NO 25
<211> LENGTH: 987
<212> TYPE: DNA
<213> ORGANISM: Homo sapiens

<400> SEQUENCE: 25

```
gctagcacca agggcccatc tgtcttcccc ctggcaccct cctccaagag cacctctggg     60

ggcacagctg ccctgggctg cctggtcaag gactacttcc ctgaacctgt gacagtgtcc    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacaca    960

cagaagagcc tctccctgtc tccgggt                                        987
```

<210> SEQ ID NO 26
<211> LENGTH: 990
<212> TYPE: DNA
<213> ORGANISM: Artificial Sequence
<220> FEATURE:
<223> OTHER INFORMATION: Synthesized

<400> SEQUENCE: 26

```
gctagcacca agggcccatc tgtcttcccc ctggcaccct cctccaagag cacctctggg     60

ggcacagctg ccctgggctg cctggtcaag gactacttcc ctgaacctgt gacagtgtcc    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtgtgtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660
```

aaagccaaag ggcagccccg agaaccacag gtgtacaccc tgcccccatc ccgggatgag 720 ctgaccaaga accaggtcag cctgacctgc ctggtcaaag gcttctatcc cagcgacatc 780 gccgtggagt gggagagcaa tgggcagccg gagaacaact acaagaccac gcctcccgtg 840 ctggactccg acggctcctt cttcctctac agcaagctca ccgtggacaa gagcaggtgg 900 cagcagggga acgtcttctc atgctccgtg atgcatgagg ctctgcacaa ccactacaca 960 cagaagagcc tctccctgtc tccgggtaaa 990

<210> SEQ ID NO 27
<211> LENGTH: 987
<212> TYPE: DNA
<213> ORGANISM: Artificial Sequence
<220> FEATURE:
<223> OTHER INFORMATION: Synthesized

<400> SEQUENCE: 27 gctagcacca agggcccatc tgtcttcccc ctggcaccct cctccaagag cacctctggg 60 ggcacagctg ccctgggctg cctggtcaag gactacttcc ctgaacctgt gacagtgtcc 120 tggaactcag gcgccctgac cagcggcgtg cacaccttcc cggctgtcct acagtcctca 180 ggactctact ccctcagcag cgtggtgacc gtgccctcca gcagcttggg cacccagacc 240 tacatctgca acgtgaatca caagcccagc aacaccaagg tggacaagaa agttgagccc 300 aaatcttgtg acaaaactca cacatgccca ccgtgcccag cacctgaact cctgggggga 360 ccgtgtgtct tcctcttccc cccaaaaccc aaggacaccc tcatgatctc ccggacccct 420 gaggtcacat gcgtggtggt ggacgtgagc cacgaagacc ctgaggtcaa gttcaactgg 480 tacgtggacg gcgtggaggt gcataatgcc aagacaaagc cgcgggagga gcagtacaac 540 agcacgtacc gtgtggtcag cgtcctcacc gtcctgcacc aggactggct gaatggcaag 600 gagtacaagt gcaaggtctc caacaaagcc ctcccagccc ccatcgagaa aaccatctcc 660 aaagccaaag ggcagccccg agaaccacag gtgtacaccc tgcccccatc ccgggatgag 720 ctgaccaaga accaggtcag cctgacctgc ctggtcaaag gcttctatcc cagcgacatc 780 gccgtggagt gggagagcaa tgggcagccg gagaacaact acaagaccac gcctcccgtg 840 ctggactccg acggctcctt cttcctctac agcaagctca ccgtggacaa gagcaggtgg 900 cagcagggga acgtcttctc atgctccgtg atgcatgagg ctctgcacaa ccactacaca 960 cagaagagcc tctccctgtc tccgggt 987

<210> SEQ ID NO 28
<211> LENGTH: 360
<212> TYPE: DNA
<213> ORGANISM: Artificial Sequence
<220> FEATURE:
<223> OTHER INFORMATION: Synthesized

<400> SEQUENCE: 28 caggtgcagc tggtgcagtc tggggctgag gtgaagaagc ctggggcctc agtgaaggtc 60 tcctgcaagg cttctggata caccttcaca gactactata tgcactgggt gaggcaggcc 120 cctggacaag ggcttgagtg gatgggatgg attgatcctg agaatggtga tactgaatat 180 gcccccacct tccagggcag ggtcaccatg accagggaca cctccatcag cacagcctac 240 atggagctga gcaggctgag atctgatgac acagctgtgt attactgtgc cagacatgat 300 gctcactatg ggacctggtt tgcttactgg ggccaaggaa ccctggtcac agtctcctca 360

<210> SEQ ID NO 29
<211> LENGTH: 360
<212> TYPE: DNA
<213> ORGANISM: Artificial Sequence
<220> FEATURE:
<223> OTHER INFORMATION: Synthesized

<400> SEQUENCE: 29 caggtgcagc tggtgcagtc tggggctgag gtgaagaagc ctggggcctc agtgaaggtc 60 tcctgcaagg cttctggata caccattgaa gactactata tgcactgggt gaggcaggcc 120 cctggacaag ggcttgagtg gatgggatgg attgatcctg agaatggtga tactgaatat 180 gcccccacct tccagggcag ggtcaccatg accagggaca cctccatcaa cacagcctac 240 atggagctga gcaggctgag atctgatgac acagctgtgt attactgtgc cagacatgat 300 gctcactatg ggacctggtt tgcttactgg ggccaaggaa ccctggtcac agtctcctca 360

<210> SEQ ID NO 30
<211> LENGTH: 360
<212> TYPE: DNA
<213> ORGANISM: Artificial Sequence
<220> FEATURE:
<223> OTHER INFORMATION: Synthesized

<400> SEQUENCE: 30 caggtgcagc tggtgcagtc tggggctgag gtgaagaagc ctggggcctc agtgaaggtc 60 tcctgcaagg cttctggata caccttcaca gactactata tgcactgggt gaggcaggcc 120 cctggacaag ggcttgagtg gatgggatgg attgatcctg agaatggtga tactgaatat 180 gcccccacct tccagggcaa ggccactatg actgcagaca cctccatcag cacagcctac 240 atggagctga gcaggctgag atctgatgac acagctgtgt attactgtgc cagacatgat 300 gctcactatg ggacctggtt tgcttactgg ggccaaggaa ccctggtcac agtctcctca 360

<210> SEQ ID NO 31
<211> LENGTH: 360
<212> TYPE: DNA
<213> ORGANISM: Artificial Sequence
<220> FEATURE:
<223> OTHER INFORMATION: Synthesized

<400> SEQUENCE: 31 caggtgcagc tggtgcagtc tggggctgag gtgaagaagc ctggggcctc agtgaaggtc 60 tcctgcaagg cttctggatt caccttcaca gactactata tgcactgggt gaggcaggcc 120 cctggacaag ggcttgagtg gatgggatgg attgatcctg agaatggtga tactgaatat 180 gcccccacct tccagggcag ggtcaccatg accagggaca cctccatcag cacagcctac 240 atggagctga gcaggctgag atctgatgac acagctgtgt attactgtgc cagacatgat 300 gctcactatg ggacctggtt tgcttactgg ggccaaggaa ccctggtcac agtctcctca 360

<210> SEQ ID NO 32
<211> LENGTH: 360
<212> TYPE: DNA
<213> ORGANISM: Artificial Sequence
<220> FEATURE:
<223> OTHER INFORMATION: Synthesized

<400> SEQUENCE: 32 caggtgcagc tggtgcagtc tggggctgag gtgaagaagc ctggggcctc agtgaaggtc 60 tcctgcaagg cttctggatt caacattgaa gactactata tgcactgggt gaggcaggcc 120 cctggacaag ggcttgagtg gattggatgg attgatcctg agaatggtga tactgaatat 180 gcccccacct tccagggcaa ggccactatg actgcagaca cctccatcaa cacagcctac 240 atggagctga gcaggctgag atctgatgac acagctgtgt attactgtaa tgtccatgat 300 gctcactatg ggacctggtt tgcttactgg ggccaaggaa ccctggtcac agtctcctca 360

<210> SEQ ID NO 33
<211> LENGTH: 339
<212> TYPE: DNA
<213> ORGANISM: Artificial Sequence
<220> FEATURE:
<223> OTHER INFORMATION: Synthesized

<400> SEQUENCE: 33 gatgttgtga tgactcagtc tccactctcc ctgcctgtca cccttggaca gcctgcctcc 60 atctcctgca gatctagtca gagcattata aggaatgatg gaaacaccta tttggaatgg 120 tttcagcaga ggccaggcca atctccaagg aggctaattt atagagtttc caacaggttt 180 tctggggtcc cagacagatt ctctggcagt gggtcaggca ctgatttcac actgaaaatc 240 agcagggtgg aggctgagga tgttggggtt tattactgct ttcaaggttc acatgttccc 300 tacacctttg gaggagggac caaggtggag atcaaacgt 339

<210> SEQ ID NO 34
<211> LENGTH: 339
<212> TYPE: DNA
<213> ORGANISM: Artificial Sequence
<220> FEATURE:
<223> OTHER INFORMATION: Synthesized

<400> SEQUENCE: 34 gatgttgtga tgactcagtc tccactctcc ctgcctgtca cccttggaca gcctgcctcc 60 atctcctgca gatctagtca gagcattata aggaatgatg gaaacaccta tttggaatgg 120 taccagcaga ggccaggcca atctccaagg aggctaattt atagagtttc caacaggttt 180 tctggggtcc cagacagatt ctctggcagt gggtcaggca ctgatttcac actgaaaatc 240 agcagggtgg aggctgagga tgttggggtt tattactgct ttcaaggttc acatgttccc 300 tacacctttg gaggagggac caaggtggag atcaaacgt 339

<210> SEQ ID NO 35
<211> LENGTH: 339
<212> TYPE: DNA
<213> ORGANISM: Artificial Sequence
<220> FEATURE:
<223> OTHER INFORMATION: Synthesized

<400> SEQUENCE: 35 gatgttgtga tgactcagtc tccactctcc ctgcctgtca cccttggaca gcctgcctcc 60 atctcctgca gatctagtca gagcattata aggaatgatg gaaacaccta tttggaatgg 120 tttctgcaga ggccaggcca atctccaagg aggctaattt atagagtttc caacaggttt 180 tctggggtcc cagacagatt ctctggcagt gggtcaggca ctgatttcac actgaaaatc 240 agcagggtgg aggctgagga tgttggggtt tattactgct ttcaaggttc acatgttccc 300 tacacctttg gaggagggac caaggtggag atcaaacgt 339

<210> SEQ ID NO 36
<211> LENGTH: 339
<212> TYPE: DNA
<213> ORGANISM: Artificial Sequence <220> FEATURE:
<223> OTHER INFORMATION: Synthesized

<400> SEQUENCE: 36 gatgttgtga tgactcagtc tccactctcc ctgcctgtca cccttggaca gcctgcctcc 60 atctcctgca gatctagtca gagcattata aggaatgatg gaaacaccta tttggaatgg 120 tttcagcaga ggccaggcca atctccaaag aggctaattt atagagtttc caacaggttt 180 tctggggtcc cagacagatt ctctggcagt gggtcaggca ctgatttcac actgaaaatc 240 agcagggtgg aggctgagga tgttggggtt tattactgct ttcaaggttc acatgttccc 300 tacacctttg gaggagggac caaggtggag atcaaacgt 339

<210> SEQ ID NO 37
<211> LENGTH: 339
<212> TYPE: DNA
<213> ORGANISM: Artificial Sequence
<220> FEATURE:
<223> OTHER INFORMATION: Synthesized

<400> SEQUENCE: 37 gatgttgtga tgactcagtc tccactctcc ctgcctgtca cccttggaca gcctgcctcc 60 atctcctgca gatctagtca gagcattata aggaatgatg gaaacaccta tttggaatgg 120 tttcagcaga ggccaggcca atctccaagg ctcctaattt atagagtttc caacaggttt 180 tctggggtcc cagacagatt ctctggcagt gggtcaggca ctgatttcac actgaaaatc 240 agcagggtgg aggctgagga tgttggggtt tattactgct ttcaaggttc acatgttccc 300 tacacctttg gaggagggac caaggtggag atcaaacgt 339

<210> SEQ ID NO 38
<211> LENGTH: 339
<212> TYPE: DNA
<213> ORGANISM: Artificial Sequence
<220> FEATURE:
<223> OTHER INFORMATION: Synthesized

<400> SEQUENCE: 38 gatgttgtga tgactcagtc tccactctcc ctgcctgtca cccttggaca gcctgcctcc 60 atctcctgca gatctagtca gagcattata aggaatgatg gaaacaccta tttggaatgg 120 tacctgcaga aaccaggcca atctccaaag ctcctaattt atagagtttc caacaggttt 180 tctggggtcc cagacagatt ctctggcagt gggtcaggca ctgatttcac actgaaaatc 240 agcagggtgg aggctgagga tgttggggtt tattactgct ttcaaggttc acatgttccc 300 tacacctttg gaggagggac caaggtggag atcaaacgt 339

<210> SEQ ID NO 39
<211> LENGTH: 20
<212> TYPE: PRT
<213> ORGANISM: Mus musculus

<400> SEQUENCE: 39

Met Lys Leu Pro Val Arg Leu Leu Val Leu Met Phe Trp Ile Pro Val
1 5 10 15

Ala Thr Ser Ser
20

<210> SEQ ID NO 40
<211> LENGTH: 19
<212> TYPE: PRT
<213> ORGANISM: Mus musculus

<400> SEQUENCE: 40

Met Lys Cys Ser Trp Val Ile Phe Phe Leu Met Ala Val Val Ile Gly
1 5 10 15

Ile Asn Ser

<210> SEQ ID NO 41
<211> LENGTH: 19
<212> TYPE: PRT
<213> ORGANISM: Mus musculus

<400> SEQUENCE: 41

Met Ala Trp Val Trp Thr Leu Leu Phe Leu Met Ala Ala Ala Gln Ser
1 5 10 15

Ala Gln Ala

<210> SEQ ID NO 42
<211> LENGTH: 106
<212> TYPE: PRT
<213> ORGANISM: Homo sapiens

<400> SEQUENCE: 42

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 43
<211> LENGTH: 330
<212> TYPE: PRT
<213> ORGANISM: Homo sapiens

<400> SEQUENCE: 43

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 44
<211> LENGTH: 329
<212> TYPE: PRT
<213> ORGANISM: Homo sapiens

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 45
<211> LENGTH: 330
<212> TYPE: PRT
<213> ORGANISM: Homo sapiens

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 46
<211> LENGTH: 329
<212> TYPE: PRT
<213> ORGANISM: Homo sapiens

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 47
<211> LENGTH: 120
<212> TYPE: PRT
<213> ORGANISM: Artificial Sequence
<220> FEATURE:
<223> OTHER INFORMATION: Synthesized

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg His Asn Ala His Tyr Gly Thr Trp Phe Ala Tyr Trp Gly Gln
            100                 105                 110

Gly Thr Leu Val Thr Val Ser Ser
        115                 120


<210> SEQ ID NO 48
<211> LENGTH: 120
<212> TYPE: PRT
<213> ORGANISM: Artificial Sequence
<220> FEATURE:
<223> OTHER INFORMATION: Synthesized

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg His Asn Ala His Tyr Gly Thr Trp Phe Ala Tyr Trp Gly Gln
            100                 105                 110

Gly Thr Leu Val Thr Val Ser Ser
        115                 120


<210> SEQ ID NO 49
<211> LENGTH: 120
<212> TYPE: PRT
<213> ORGANISM: Artificial Sequence
<220> FEATURE:
<223> OTHER INFORMATION: Synthesized

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Lys Ala Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg His Asn Ala His Tyr Gly Thr Trp Phe Ala Tyr Trp Gly Gln
            100                 105                 110

Gly Thr Leu Val Thr Val Ser Ser
        115                 120


<210> SEQ ID NO 50
<211> LENGTH: 120
<212> TYPE: PRT
<213> ORGANISM: Artificial Sequence
<220> FEATURE:
<223> OTHER INFORMATION: Synthesized

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val His Asn Ala His Tyr Gly Thr Trp Phe Ala Tyr Trp Gly Gln
            100                 105                 110

Gly Thr Leu Val Thr Val Ser Ser
        115                 120


<210> SEQ ID NO 51
<211> LENGTH: 120
<212> TYPE: PRT
<213> ORGANISM: Artificial Sequence
```

<220> FEATURE:
<223> OTHER INFORMATION: Synthesized

<400> SEQUENCE: 51

Gln Val Gln Leu Val Gln Ser Gly Ala Glu Val Lys Lys Pro Gly Ala
1 5 10 15

Ser Val Lys Val Ser Cys Lys Ala Ser Gly Leu Asn Ile Glu Asp Tyr
20 25 30

Tyr Met His Trp Val Arg Gln Ala Pro Gly Gln Gly Leu Glu Trp Ile
35 40 45

Gly Trp Ile Asp Pro Glu Asn Gly Asp Thr Glu Tyr Gly Pro Lys Phe
50 55 60

Gln Gly Lys Ala Thr Met Thr Ala Asp Thr Ser Ile Asn Thr Ala Tyr
65 70 75 80

Met Glu Leu Ser Arg Leu Arg Ser Asp Asp Thr Ala Val Tyr Tyr Cys
85 90 95

Thr Val His Asn Ala His Tyr Gly Thr Trp Phe Ala Tyr Trp Gly Gln
100 105 110

Gly Thr Leu Val Thr Val Ser Ser
115 120

<210> SEQ ID NO 52
<211> LENGTH: 120
<212> TYPE: PRT
<213> ORGANISM: Artificial Sequence
<220> FEATURE:
<223> OTHER INFORMATION: Synthesized

<400> SEQUENCE: 52

Gln Val Gln Leu Val Gln Ser Gly Ala Glu Val Lys Lys Pro Gly Ala
1 5 10 15

Ser Val Lys Val Ser Cys Lys Ala Ser Gly Leu Thr Ile Glu Asp Tyr
20 25 30

Tyr Met His Trp Val Arg Gln Ala Pro Gly Gln Gly Leu Glu Trp Met
35 40 45

Gly Trp Ile Asp Pro Glu Asn Gly Asp Thr Glu Tyr Gly Pro Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Val His Asn Ala His Tyr Gly Thr Trp Phe Ala Tyr Trp Gly Gln
100 105 110

Gly Thr Leu Val Thr Val Ser Ser
115 120

<210> SEQ ID NO 53
<211> LENGTH: 120
<212> TYPE: PRT
<213> ORGANISM: Artificial Sequence
<220> FEATURE:
<223> OTHER INFORMATION: Synthesized

<400> SEQUENCE: 53

Gln Val Gln Leu Val Gln Ser Gly Ala Glu Val Lys Lys Pro Gly Ala
1 5 10 15

Ser Val Lys Val Ser Cys Lys Ala Ser Gly Leu Thr Ile Glu Asp Tyr
20 25 30

```
Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser
        115                 120


<210> SEQ ID NO 54
<211> LENGTH: 113
<212> TYPE: PRT
<213> ORGANISM: Artificial Sequence
<220> FEATURE:
<223> OTHER INFORMATION: Synthesized

<400> SEQUENCE: 54

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Phe Gln Gln Arg Pro Gly Gln Ser
        35                  40                  45

Pro Arg Arg Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg


<210> SEQ ID NO 55
<211> LENGTH: 113
<212> TYPE: PRT
<213> ORGANISM: Artificial Sequence
<220> FEATURE:
<223> OTHER INFORMATION: Synthesized

<400> SEQUENCE: 55

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Gln Gln Arg Pro Gly Gln Ser
        35                  40                  45

Pro Arg Arg Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95
```

Ser His Val Pro Tyr Thr Phe Gly Gly Gly Thr Lys Val Glu Ile Lys
100 105 110

Arg

<210> SEQ ID NO 56
<211> LENGTH: 113
<212> TYPE: PRT
<213> ORGANISM: Artificial Sequence
<220> FEATURE:
<223> OTHER INFORMATION: Synthesized

<400> SEQUENCE: 56

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu His Ser
20 25 30

Ser Gly Asn Thr Tyr Leu Glu Trp Phe Leu Gln Arg Pro Gly Gln Ser
35 40 45

Pro Arg Arg Leu Ile Tyr Lys Ile Ser Thr Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Tyr Thr Phe Gly Gly Gly Thr Lys Val Glu Ile Lys
100 105 110

Arg

<210> SEQ ID NO 57
<211> LENGTH: 113
<212> TYPE: PRT
<213> ORGANISM: Artificial Sequence
<220> FEATURE:
<223> OTHER INFORMATION: Synthesized

<400> SEQUENCE: 57

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu His Ser
20 25 30

Ser Gly Asn Thr Tyr Leu Glu Trp Phe Gln Gln Arg Pro Gly Gln Ser
35 40 45

Pro Lys Arg Leu Ile Tyr Lys Ile Ser Thr Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Tyr Thr Phe Gly Gly Gly Thr Lys Val Glu Ile Lys
100 105 110

Arg

<210> SEQ ID NO 58
<211> LENGTH: 113
<212> TYPE: PRT
<213> ORGANISM: Artificial Sequence
<220> FEATURE:
<223> OTHER INFORMATION: Synthesized

<400> SEQUENCE: 58

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu His Ser
20 25 30

Ser Gly Asn Thr Tyr Leu Glu Trp Phe Gln Gln Arg Pro Gly Gln Ser
35 40 45

Pro Arg Pro Leu Ile Tyr Lys Ile Ser Thr Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Tyr Thr Phe Gly Gly Gly Thr Lys Val Glu Ile Lys
100 105 110

Arg

<210> SEQ ID NO 59
<211> LENGTH: 113
<212> TYPE: PRT
<213> ORGANISM: Artificial Sequence
<220> FEATURE:
<223> OTHER INFORMATION: Synthesized

<400> SEQUENCE: 59

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu His Ser
20 25 30

Ser Gly Asn Thr Tyr Leu Glu Trp Tyr Leu Gln Arg Pro Gly Gln Ser
35 40 45

Pro Lys Pro Leu Ile Tyr Lys Ile Ser Thr Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Tyr Thr Phe Gly Gly Gly Thr Lys Val Glu Ile Lys
100 105 110

Arg

<210> SEQ ID NO 60
<211> LENGTH: 113
<212> TYPE: PRT
<213> ORGANISM: Artificial Sequence
<220> FEATURE:
<223> OTHER INFORMATION: Synthesized

<400> SEQUENCE: 60

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu His Ser
20 25 30

Ser Gly Asn Thr Tyr Leu Glu Trp Tyr Gln Gln Arg Pro Gly Gln Ser
35 40 45

Pro Arg Pro Leu Ile Tyr Lys Ile Ser Thr Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Tyr Thr Phe Gly Gly Gly Thr Lys Val Glu Ile Lys
100 105 110

Arg

<210> SEQ ID NO 61
<211> LENGTH: 57
<212> TYPE: DNA
<213> ORGANISM: Mus musculus

<400> SEQUENCE: 61 atgaaatgca gctgggtcat cttcttcctg atggcagtgg ttataggaat caattca 57

<210> SEQ ID NO 62
<211> LENGTH: 57
<212> TYPE: DNA
<213> ORGANISM: Mus musculus

<400> SEQUENCE: 62 atgaagttgc ctgttaggct gttggtgctg atgttctgga ttcctgctac cagcagt 57

<210> SEQ ID NO 63
<211> LENGTH: 57
<212> TYPE: DNA
<213> ORGANISM: Mus musculus

<400> SEQUENCE: 63 atggcttggg tgtggacctt gctattcctg atggcagctg cccaaagtgc ccaagca 57

<210> SEQ ID NO 64
<211> LENGTH: 324
<212> TYPE: DNA
<213> ORGANISM: Homo sapiens

<400> SEQUENCE: 64 acgacggtgg ctgcaccatc tgtcttcatc ttcccgccat ctgatgagca gttgaaatct 60 ggaactgcct ctgttgtgtg cctgctgaat aacttctatc ccagagaggc caaagtacag 120 tggaaggtgg ataacgccct ccaatcgggt aactcccagg agagtgtcac agagcaggac 180 agcaaggaca gcacctacag cctcagcagc accctgacgc tgagcaaagc agactacgag 240 aaacacaaag tctacgcctg cgaagtcacc catcagggcc tgagctcgcc cgtcacaaag 300 agcttcaaca ggggagagtg ttag 324

<210> SEQ ID NO 65
<211> LENGTH: 990
<212> TYPE: DNA
<213> ORGANISM: Homo sapiens

<400> SEQUENCE: 65 gctagcacca agggcccatc tgtcttcccc ctggcaccct cctccaagag cacctctggg 60 ggcacagctg ccctgggctg cctggtcaag gactacttcc ctgaacctgt gacagtgtcc 120 tggaactcag gcgccctgac cagcggcgtg cacaccttcc cggctgtcct acagtcctca 180 ggactctact ccctcagcag cgtggtgacc gtgccctcca gcagcttggg cacccagacc 240 tacatctgca acgtgaatca caagcccagc aacaccaagg tggacaagaa agttgagccc 300 aaatcttgtg acaaaactca cacatgccca ccgtgcccag cacctgaact cctgggggga 360 ccgtcagtct tcctcttccc cccaaaaccc aaggacaccc tcatgatctc ccggacccct 420 gaggtcacat gcgtggtggt ggacgtgagc cacgaagacc ctgaggtcaa gttcaactgg 480 tacgtggacg gcgtggaggt gcataatgcc aagacaaagc cgcgggagga gcagtacaac 540 agcacgtacc gtgtggtcag cgtcctcacc gtcctgcacc aggactggct gaatggcaag 600 gagtacaagt gcaaggtctc caacaaagcc ctcccagccc ccatcgagaa aaccatctcc 660 aaagccaaag ggcagccccg agaaccacag gtgtacaccc tgcccccatc ccgggatgag 720 ctgaccaaga accaggtcag cctgacctgc ctggtcaaag gcttctatcc cagcgacatc 780 gccgtggagt gggagagcaa tgggcagccg gagaacaact acaagaccac gcctcccgtg 840 ctggactccg acggctcctt cttcctctac agcaagctca ccgtggacaa gagcaggtgg 900 cagcagggga acgtcttctc atgctccgtg atgcatgagg ctctgcacaa ccactacaca 960 cagaagagcc tctccctgtc tccgggtaaa 990

<210> SEQ ID NO 66
<211> LENGTH: 987
<212> TYPE: DNA
<213> ORGANISM: Homo sapiens

<400> SEQUENCE: 66 gctagcacca agggcccatc tgtcttcccc ctggcaccct cctccaagag cacctctggg 60 ggcacagctg ccctgggctg cctggtcaag gactacttcc ctgaacctgt gacagtgtcc 120 tggaactcag gcgccctgac cagcggcgtg cacaccttcc cggctgtcct acagtcctca 180 ggactctact ccctcagcag cgtggtgacc gtgccctcca gcagcttggg cacccagacc 240 tacatctgca acgtgaatca caagcccagc aacaccaagg tggacaagaa agttgagccc 300 aaatcttgtg acaaaactca cacatgccca ccgtgcccag cacctgaact cctgggggga 360 ccgtcagtct tcctcttccc cccaaaaccc aaggacaccc tcatgatctc ccggacccct 420 gaggtcacat gcgtggtggt ggacgtgagc cacgaagacc ctgaggtcaa gttcaactgg 480 tacgtggacg gcgtggaggt gcataatgcc aagacaaagc cgcgggagga gcagtacaac 540 agcacgtacc gtgtggtcag cgtcctcacc gtcctgcacc aggactggct gaatggcaag 600 gagtacaagt gcaaggtctc caacaaagcc ctcccagccc ccatcgagaa aaccatctcc 660 aaagccaaag ggcagccccg agaaccacag gtgtacaccc tgcccccatc ccgggatgag 720 ctgaccaaga accaggtcag cctgacctgc ctggtcaaag gcttctatcc cagcgacatc 780 gccgtggagt gggagagcaa tgggcagccg gagaacaact acaagaccac gcctcccgtg 840 ctggactccg acggctcctt cttcctctac agcaagctca ccgtggacaa gagcaggtgg 900 cagcagggga acgtcttctc atgctccgtg atgcatgagg ctctgcacaa ccactacaca 960 cagaagagcc tctccctgtc tccgggt 987

<210> SEQ ID NO 67
<211> LENGTH: 990
<212> TYPE: DNA
<213> ORGANISM: Artificial Sequence
<220> FEATURE:
<223> OTHER INFORMATION: Synthesized

<400> SEQUENCE: 67 gctagcacca agggcccatc tgtcttcccc ctggcaccct cctccaagag cacctctggg 60 ggcacagctg ccctgggctg cctggtcaag gactacttcc ctgaacctgt gacagtgtcc 120

```
tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtgtgtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacaca    960

cagaagagcc tctccctgtc tccgggtaaa                                     990
```

<210> SEQ ID NO 68
<211> LENGTH: 987
<212> TYPE: DNA
<213> ORGANISM: Artificial Sequence
<220> FEATURE:
<223> OTHER INFORMATION: Synthesized

<400> SEQUENCE: 68

```
gctagcacca agggcccatc tgtcttcccc ctggcaccct cctccaagag cacctctggg     60

ggcacagctg ccctgggctg cctggtcaag gactacttcc ctgaacctgt gacagtgtcc    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtgtgtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacaca    960

cagaagagcc tctccctgtc tccgggt                                        987
```

<210> SEQ ID NO 69
<211> LENGTH: 360
<212> TYPE: DNA
<213> ORGANISM: Artificial Sequence <220> FEATURE:
<223> OTHER INFORMATION: Synthesized

<400> SEQUENCE: 69 caggtgcagc tggtgcagtc tggggctgag gtgaagaagc ctggggcctc agtgaaggtc 60 tcctgcaagg cttctggata caccttcaca gactactata tgcactgggt gaggcaggcc 120 cctggacaag ggcttgagtg gatgggatgg attgatcctg aaaatggtga tactgaatat 180 ggcccgaagt tccagggcag ggtcaccatg accagggaca cctccatcag cacagcctac 240 atggagctga gcaggctgag atctgatgac acagctgtgt attactgtgc cagacataat 300 gctcactacg ggacctggtt tgcttactgg ggccaaggaa ccctggtcac agtctcctca 360

<210> SEQ ID NO 70
<211> LENGTH: 360
<212> TYPE: DNA
<213> ORGANISM: Artificial Sequence
<220> FEATURE:
<223> OTHER INFORMATION: Synthesized

<400> SEQUENCE: 70 caggtgcagc tggtgcagtc tggggctgag gtgaagaagc ctggggcctc agtgaaggtc 60 tcctgcaagg cttctggata caccattgaa gactactata tgcactgggt gaggcaggcc 120 cctggacaag ggcttgagtg gatgggatgg attgatcctg aaaatggtga tactgaatat 180 ggcccgaagt tccagggcag ggtcaccatg accagggaca cctccatcaa cacagcctac 240 atggagctga gcaggctgag atctgatgac acagctgtgt attactgtgc cagacataat 300 gctcactacg ggacctggtt tgcttactgg ggccaaggaa ccctggtcac agtctcctca 360

<210> SEQ ID NO 71
<211> LENGTH: 360
<212> TYPE: DNA
<213> ORGANISM: Artificial Sequence
<220> FEATURE:
<223> OTHER INFORMATION: Synthesized

<400> SEQUENCE: 71 caggtgcagc tggtgcagtc tggggctgag gtgaagaagc ctggggcctc agtgaaggtc 60 tcctgcaagg cttctggata caccttcaca gactactata tgcactgggt gaggcaggcc 120 cctggacaag ggcttgagtg gatgggatgg attgatcctg aaaatggtga tactgaatat 180 ggcccgaagt tccagggcaa ggccaccatg accgcagaca cctccatcag cacagcctac 240 atggagctga gcaggctgag atctgatgac acagctgtgt attactgtgc cagacataat 300 gctcactacg ggacctggtt tgcttactgg ggccaaggaa ccctggtcac agtctcctca 360

<210> SEQ ID NO 72
<211> LENGTH: 360
<212> TYPE: DNA
<213> ORGANISM: Artificial Sequence
<220> FEATURE:
<223> OTHER INFORMATION: Synthesized

<400> SEQUENCE: 72 caggtgcagc tggtgcagtc tggggctgag gtgaagaagc ctggggcctc agtgaaggtc 60 tcctgcaagg cttctggact caccttcaca gactactata tgcactgggt gaggcaggcc 120 cctggacaag ggcttgagtg gatgggatgg attgatcctg aaaatggtga tactgaatat 180 ggcccgaagt tccagggcag ggtcaccatg accagggaca cctccatcag cacagcctac 240 atggagctga gcaggctgag atctgatgac acagctgtgt attactgtac tgtccataat 300 gctcactacg ggacctggtt tgcttactgg ggccaaggaa ccctggtcac agtctcctca 360

<210> SEQ ID NO 73
<211> LENGTH: 360
<212> TYPE: DNA
<213> ORGANISM: Artificial Sequence
<220> FEATURE:
<223> OTHER INFORMATION: Synthesized

<400> SEQUENCE: 73 caggtgcagc tggtgcagtc tggggctgag gtgaagaagc ctggggcctc agtgaaggtc 60 tcctgcaagg cttctggact caacattgaa gactactata tgcactgggt gaggcaggcc 120 cctggacaag ggcttgagtg gattggatgg attgatcctg aaaatggtga tactgaatat 180 ggcccgaagt tccagggcaa ggccaccatg accgcagaca cctccatcaa cacagcctac 240 atggagctga gcaggctgag atctgatgac acagctgtgt attactgtac tgtccataat 300 gctcactacg ggacctggtt tgcttactgg ggccaaggaa ccctggtcac agtctcctca 360

<210> SEQ ID NO 74
<211> LENGTH: 360
<212> TYPE: DNA
<213> ORGANISM: Artificial Sequence
<220> FEATURE:
<223> OTHER INFORMATION: Synthesized

<400> SEQUENCE: 74 caggtgcagc tggtgcagtc tggggctgag gtgaagaagc ctggggcctc agtgaaggtc 60 tcctgcaagg cttctggact caccattgaa gactactata tgcactgggt gaggcaggcc 120 cctggacaag ggcttgagtg gatgggatgg attgatcctg aaaatggtga tactgaatat 180 ggcccgaagt tccagggcag ggtcaccatg accagggaca cctccatcag cacagcctac 240 atggagctga gcaggctgag atctgatgac acagctgtgt attactgtgc cgtccataat 300 gctcactacg ggacctggtt tgcttactgg ggccaaggaa ccctggtcac agtctcctca 360

<210> SEQ ID NO 75
<211> LENGTH: 360
<212> TYPE: DNA
<213> ORGANISM: Artificial Sequence
<220> FEATURE:
<223> OTHER INFORMATION: Synthesized

<400> SEQUENCE: 75 caggtgcagc tggtgcagtc tggggctgag gtgaagaagc ctggggcctc agtgaaggtc 60 tcctgcaagg cttctggact caccattgaa gactactata tgcactgggt gaggcaggcc 120 cctggacaag ggcttgagtg gatgggatgg attgatcctg aaaatggtga tactgaatat 180 ggcccgaagt tccagggcag ggtcaccatg accagggaca cctccatcaa cacagcctac 240 atggagctga gcaggctgag atctgatgac acagctgtgt attactgtgc cgtccataat 300 gctcactacg ggacctggtt tgcttactgg ggccaaggaa ccctggtcac agtctcctca 360

<210> SEQ ID NO 76
<211> LENGTH: 370
<212> TYPE: DNA
<213> ORGANISM: Artificial Sequence
<220> FEATURE:
<223> OTHER INFORMATION: Synthesized

<400> SEQUENCE: 76 gatgttctgg attcctgcta ccagcagtga tgttgtgatg actcagtctc cactctccct 60 gcctgtcacc cttggacagc ctgcctccat ctcctgcaga tctagtcaga gccttttaca 120 cagtagtgga aacacctatt tagaatggtt tcagcagagg ccaggccaat ctccaaggag 180 gctaatttat aaaatttcca cccgattttc tggggtccca gacagattct ctggcagtgg 240 gtcaggcact gatttcacac tgaaaatcag cagggtggag gctgaggatg ttggggttta 300 ttactgcttt caaggttcac atgttcccta cacctttgga ggagggacca aggtggagat 360 caaacgtacg 370

<210> SEQ ID NO 77
<211> LENGTH: 370
<212> TYPE: DNA
<213> ORGANISM: Artificial Sequence
<220> FEATURE:
<223> OTHER INFORMATION: Synthesized

<400> SEQUENCE: 77 gatgttctgg attcctgcta ccagcagtga tgttgtgatg actcagtctc cactctccct 60 gcctgtcacc cttggacagc ctgcctccat ctcctgcaga tctagtcaga gccttttaca 120 cagtagtgga aacacctatt tagaatggta ccagcagagg ccaggccaat ctccaaggag 180 gctaatttat aaaatttcca cccgattttc tggggtccca gacagattct ctggcagtgg 240 gtcaggcact gatttcacac tgaaaatcag cagggtggag gctgaggatg ttggggttta 300 ttactgcttt caaggttcac atgttcccta cacctttgga ggagggacca aggtggagat 360 caaacgtacg 370

<210> SEQ ID NO 78
<211> LENGTH: 370
<212> TYPE: DNA
<213> ORGANISM: Artificial Sequence
<220> FEATURE:
<223> OTHER INFORMATION: Synthesized

<400> SEQUENCE: 78 gatgttctgg attcctgcta ccagcagtga tgttgtgatg actcagtctc cactctccct 60 gcctgtcacc cttggacagc ctgcctccat ctcctgcaga tctagtcaga gccttttaca 120 cagtagtgga aacacctatt tagaatggtt tctgcagagg ccaggccaat ctccaaggag 180 gctaatttat aaaatttcca cccgattttc tggggtccca gacagattct ctggcagtgg 240 gtcaggcact gatttcacac tgaaaatcag cagggtggag gctgaggatg ttggggttta 300 ttactgcttt caaggttcac atgttcccta cacctttgga ggagggacca aggtggagat 360 caaacgtacg 370

<210> SEQ ID NO 79
<211> LENGTH: 370
<212> TYPE: DNA
<213> ORGANISM: Artificial Sequence
<220> FEATURE:
<223> OTHER INFORMATION: Synthesized

<400> SEQUENCE: 79 gatgttctgg attcctgcta ccagcagtga tgttgtgatg actcagtctc cactctccct 60 gcctgtcacc cttggacagc ctgcctccat ctcctgcaga tctagtcaga gccttttaca 120 cagtagtgga aacacctatt tagaatggtt tcagcagagg ccaggccaat ctccaaagag 180 gctaatttat aaaatttcca cccgattttc tggggtccca gacagattct ctggcagtgg 240 gtcaggcact gatttcacac tgaaaatcag cagggtggag gctgaggatg ttggggttta 300 ttactgcttt caaggttcac atgttcccta cacctttgga ggagggacca aggtggagat 360 caaacgtacg 370

<210> SEQ ID NO 80
<211> LENGTH: 370
<212> TYPE: DNA
<213> ORGANISM: Artificial Sequence
<220> FEATURE:
<223> OTHER INFORMATION: Synthesized

<400> SEQUENCE: 80 gatgttctgg attcctgcta ccagcagtga tgttgtgatg actcagtctc cactctccct 60 gcctgtcacc cttggacagc ctgcctccat ctcctgcaga tctagtcaga gccttttaca 120 cagtagtgga aacacctatt tagaatggtt tcagcagagg ccaggccaat ctccaaggcc 180 cctaatttat aaaatttcca cccgattttc tggggtccca gacagattct ctggcagtgg 240 gtcaggcact gatttcacac tgaaaatcag cagggtggag gctgaggatg ttggggttta 300 ttactgcttt caaggttcac atgttcccta cacctttgga ggagggacca aggtggagat 360 caaacgtacg 370

<210> SEQ ID NO 81
<211> LENGTH: 339
<212> TYPE: DNA
<213> ORGANISM: Artificial Sequence
<220> FEATURE:
<223> OTHER INFORMATION: Synthesized

<400> SEQUENCE: 81 gatgttgtga tgactcagtc tccactctcc ctgcctgtca cccttggaca gcctgcctcc 60 atctcctgca gatctagtca gagcctttta cacagtagtg gaaacaccta tttagaatgg 120 tacctgcaga ggccaggcca atctccaaag cccctaattt ataaaatttc cacccgattt 180 tctggggtcc cagacagatt ctctggcagt gggtcaggca ctgatttcac actgaaaatc 240 agcagggtgg aggctgagga tgttggggtt tattactgct ttcaaggttc acatgttccc 300 tacacctttg gaggagggac caaggtggag atcaaacgt 339

<210> SEQ ID NO 82
<211> LENGTH: 339
<212> TYPE: DNA
<213> ORGANISM: Artificial Sequence
<220> FEATURE:
<223> OTHER INFORMATION: Synthesized

<400> SEQUENCE: 82 gatgttgtga tgactcagtc tccactctcc ctgcctgtca cccttggaca gcctgcctcc 60 atctcctgca gatctagtca gagcctttta cacagtagtg gaaacaccta tttagaatgg 120 taccagcaga ggccaggcca atctccaagg cccctaattt ataaaatttc cacccgattt 180 tctggggtcc cagacagatt ctctggcagt gggtcaggca ctgatttcac actgaaaatc 240 agcagggtgg aggctgagga tgttggggtt tattactgct ttcaaggttc acatgttccc 300 tacacctttg gaggagggac caaggtggag atcaaacgt 339

<210> SEQ ID NO 83
<211> LENGTH: 755
<212> TYPE: PRT
<213> ORGANISM: Homo sapiens

<400> SEQUENCE: 83

Met Ala Arg Lys Leu Ser Val Ile Leu Ile Leu Thr Phe Ala Leu Ser
1 5 10 15

Val Thr Asn Pro Leu His Glu Leu Lys Ala Ala Ala Phe Pro Gln Thr
20 25 30

Thr Glu Lys Ile Ser Pro Asn Trp Glu Ser Gly Ile Asn Val Asp Leu
35 40 45

Ala Ile Ser Thr Arg Gln Tyr His Leu Gln Gln Leu Phe Tyr Arg Tyr
50 55 60

Gly Glu Asn Asn Ser Leu Ser Val Glu Gly Phe Arg Lys Leu Leu Gln
65 70 75 80

Asn Ile Gly Ile Asp Lys Ile Lys Arg Ile His Ile His His Asp His
85 90 95

Asp His His Ser Asp His Glu His His Ser Asp His Glu Arg His Ser
100 105 110

Asp His Glu His His Ser Glu His Glu His His Ser Asp His Asp His
115 120 125

His Ser His His Asn His Ala Ala Ser Gly Lys Asn Lys Arg Lys Ala
130 135 140

Leu Cys Pro Asp His Asp Ser Asp Ser Ser Gly Lys Asp Pro Arg Asn
145 150 155 160

Ser Gln Gly Lys Gly Ala His Arg Pro Glu His Ala Ser Gly Arg Arg
165 170 175

Asn Val Lys Asp Ser Val Ser Ala Ser Glu Val Thr Ser Thr Val Tyr
180 185 190

Asn Thr Val Ser Glu Gly Thr His Phe Leu Glu Thr Ile Glu Thr Pro
195 200 205

Arg Pro Gly Lys Leu Phe Pro Lys Asp Val Ser Ser Ser Thr Pro Pro
210 215 220

Ser Val Thr Ser Lys Ser Arg Val Ser Arg Leu Ala Gly Arg Lys Thr
225 230 235 240

Asn Glu Ser Val Ser Glu Pro Arg Lys Gly Phe Met Tyr Ser Arg Asn
245 250 255

Thr Asn Glu Asn Pro Gln Glu Cys Phe Asn Ala Ser Lys Leu Leu Thr
260 265 270

Ser His Gly Met Gly Ile Gln Val Pro Leu Asn Ala Thr Glu Phe Asn
275 280 285

Tyr Leu Cys Pro Ala Ile Ile Asn Gln Ile Asp Ala Arg Ser Cys Leu
290 295 300

Ile His Thr Ser Glu Lys Lys Ala Glu Ile Pro Pro Lys Thr Tyr Ser
305 310 315 320

Leu Gln Ile Ala Trp Val Gly Gly Phe Ile Ala Ile Ser Ile Ile Ser
325 330 335

Phe Leu Ser Leu Leu Gly Val Ile Leu Val Pro Leu Met Asn Arg Val
340 345 350

Phe Phe Lys Phe Leu Leu Ser Phe Leu Val Ala Leu Ala Val Gly Thr
355 360 365

Leu Ser Gly Asp Ala Phe Leu His Leu Leu Pro His Ser His Ala Ser
370 375 380

His His His Ser His Ser His Glu Glu Pro Ala Met Glu Met Lys Arg
385 390 395 400

Gly Pro Leu Phe Ser His Leu Ser Ser Gln Asn Ile Glu Glu Ser Ala
405 410 415

Tyr Phe Asp Ser Thr Trp Lys Gly Leu Thr Ala Leu Gly Gly Leu Tyr
420 425 430

Phe Met Phe Leu Val Glu His Val Leu Thr Leu Ile Lys Gln Phe Lys
435 440 445

Asp Lys Lys Lys Lys Asn Gln Lys Lys Pro Glu Asn Asp Asp Asp Val
450 455 460

Glu Ile Lys Lys Gln Leu Ser Lys Tyr Glu Ser Gln Leu Ser Thr Asn
465 470 475 480

Glu Glu Lys Val Asp Thr Asp Asp Arg Thr Glu Gly Tyr Leu Arg Ala
485 490 495

Asp Ser Gln Glu Pro Ser His Phe Asp Ser Gln Gln Pro Ala Val Leu
500 505 510

Glu Glu Glu Glu Val Met Ile Ala His Ala His Pro Gln Glu Val Tyr
515 520 525

Asn Glu Tyr Val Pro Arg Gly Cys Lys Asn Lys Cys His Ser His Phe
530 535 540

His Asp Thr Leu Gly Gln Ser Asp Asp Leu Ile His His His His Asp
545 550 555 560

Tyr His His Ile Leu His His His His His Gln Asn His His Pro His
565 570 575

Ser His Ser Gln Arg Tyr Ser Arg Glu Glu Leu Lys Asp Ala Gly Val
580 585 590

Ala Thr Leu Ala Trp Met Val Ile Met Gly Asp Gly Leu His Asn Phe
595 600 605

Ser Asp Gly Leu Ala Ile Gly Ala Ala Phe Thr Glu Gly Leu Ser Ser
610 615 620

Gly Leu Ser Thr Ser Val Ala Val Phe Cys His Glu Leu Pro His Glu
625 630 635 640

Leu Gly Asp Phe Ala Val Leu Leu Lys Ala Gly Met Thr Val Lys Gln
645 650 655

Ala Val Leu Tyr Asn Ala Leu Ser Ala Met Leu Ala Tyr Leu Gly Met
660 665 670

Ala Thr Gly Ile Phe Ile Gly His Tyr Ala Glu Asn Val Ser Met Trp
675 680 685

Ile Phe Ala Leu Thr Ala Gly Leu Phe Met Tyr Val Ala Leu Val Asp
690 695 700

Met Val Pro Glu Met Leu His Asn Asp Ala Ser Asp His Gly Cys Ser
705 710 715 720

Arg Trp Gly Tyr Phe Phe Leu Gln Asn Ala Gly Met Leu Leu Gly Phe
725 730 735

Gly Ile Met Leu Leu Ile Ser Ile Phe Glu His Lys Ile Val Phe Arg
740 745 750

Ile Asn Phe
755

<210> SEQ ID NO 84
<211> LENGTH: 749
<212> TYPE: PRT
<213> ORGANISM: Homo sapiens

<400> SEQUENCE: 84

Met Ala Arg Lys Leu Ser Val Ile Leu Ile Leu Thr Phe Ala Leu Ser
1 5 10 15

Val Thr Asn Pro Leu His Glu Leu Lys Ala Ala Ala Phe Pro Gln Thr
20 25 30

Thr Glu Lys Ile Ser Pro Asn Trp Glu Ser Gly Ile Asn Val Asp Leu
35 40 45

Ala Ile Ser Thr Arg Gln Tyr His Leu Gln Gln Leu Phe Tyr Arg Tyr
50 55 60

Gly Glu Asn Asn Ser Leu Ser Val Glu Gly Phe Arg Lys Leu Leu Gln
65 70 75 80

Asn Ile Gly Ile Asp Lys Ile Lys Arg Ile His Ile His His Asp His
85 90 95

Asp His His Ser Asp His Glu His His Ser Asp His Glu Arg His Ser
100 105 110

Asp His Glu His His Ser Asp His Glu His His Ser Asp His Asn His
115 120 125

Ala Ala Ser Gly Lys Asn Lys Arg Lys Ala Leu Cys Pro Asp His Asp
130 135 140

Ser Asp Ser Ser Gly Lys Asp Pro Arg Asn Ser Gln Gly Lys Gly Ala
145 150 155 160

His Arg Pro Glu His Ala Ser Gly Arg Arg Asn Val Lys Asp Ser Val
165 170 175

Ser Ala Ser Glu Val Thr Ser Thr Val Tyr Asn Thr Val Ser Glu Gly
180 185 190

Thr His Phe Leu Glu Thr Ile Glu Thr Pro Arg Pro Gly Lys Leu Phe
195 200 205

Pro Lys Asp Val Ser Ser Ser Thr Pro Pro Ser Val Thr Ser Lys Ser
210 215 220

Arg Val Ser Arg Leu Ala Gly Arg Lys Thr Asn Glu Ser Val Ser Glu
225 230 235 240

Pro Arg Lys Gly Phe Met Tyr Ser Arg Asn Thr Asn Glu Asn Pro Gln
245 250 255

Glu Cys Phe Asn Ala Ser Lys Leu Leu Thr Ser His Gly Met Gly Ile
260 265 270

Gln Val Pro Leu Asn Ala Thr Glu Phe Asn Tyr Leu Cys Pro Ala Ile
275 280 285

Ile Asn Gln Ile Asp Ala Arg Ser Cys Leu Ile His Thr Ser Glu Lys
290 295 300

Lys Ala Glu Ile Pro Pro Lys Thr Tyr Ser Leu Gln Ile Ala Trp Val
305 310 315 320

Gly Gly Phe Ile Ala Ile Ser Ile Ile Ser Phe Leu Ser Leu Leu Gly
325 330 335

Val Ile Leu Val Pro Leu Met Asn Arg Val Phe Phe Lys Phe Leu Leu
340 345 350

Ser Phe Leu Val Ala Leu Ala Val Gly Thr Leu Ser Gly Asp Ala Phe
355 360 365

Leu His Leu Leu Pro His Ser His Ala Ser His His His Ser His Ser
370 375 380

His Glu Glu Pro Ala Met Glu Met Lys Arg Gly Pro Leu Phe Ser His
385 390 395 400

Leu Ser Ser Gln Asn Ile Glu Glu Ser Ala Tyr Phe Asp Ser Thr Trp
405 410 415

```
Lys Gly Leu Thr Ala Leu Gly Gly Leu Tyr Phe Met Phe Leu Val Glu
            420                 425                 430

His Val Leu Thr Leu Ile Lys Gln Phe Lys Asp Lys Lys Lys Lys Asn
        435                 440                 445

Gln Lys Lys Pro Glu Asn Asp Asp Asp Val Glu Ile Lys Lys Gln Leu
    450                 455                 460

Ser Lys Tyr Glu Ser Gln Leu Ser Thr Asn Glu Glu Lys Val Asp Thr
465                 470                 475                 480

Asp Asp Arg Thr Glu Gly Tyr Leu Arg Ala Asp Ser Gln Glu Pro Ser
                485                 490                 495

His Phe Asp Ser Gln Gln Pro Ala Val Leu Glu Glu Glu Glu Val Met
            500                 505                 510

Ile Ala His Ala His Pro Gln Glu Val Tyr Asn Glu Tyr Val Pro Arg
        515                 520                 525

Gly Cys Lys Asn Lys Cys His Ser His Phe His Asp Thr Leu Gly Gln
    530                 535                 540

Ser Asp Asp Leu Ile His His His His Asp Tyr His His Ile Leu His
545                 550                 555                 560

His His His His Gln Asn His His Pro His Ser His Ser Gln Arg Tyr
                565                 570                 575

Ser Arg Glu Glu Leu Lys Asp Ala Gly Val Ala Thr Leu Ala Trp Met
            580                 585                 590

Val Ile Met Gly Asp Gly Leu His Asn Phe Ser Asp Gly Leu Ala Ile
        595                 600                 605

Gly Ala Ala Phe Thr Glu Gly Leu Ser Ser Gly Leu Ser Thr Ser Val
    610                 615                 620

Ala Val Phe Cys His Glu Leu Pro His Glu Leu Gly Asp Phe Ala Val
625                 630                 635                 640

Leu Leu Lys Ala Gly Met Thr Val Lys Gln Ala Val Leu Tyr Asn Ala
                645                 650                 655

Leu Ser Ala Met Leu Ala Tyr Leu Gly Met Ala Thr Gly Ile Phe Ile
            660                 665                 670

Gly His Tyr Ala Glu Asn Val Ser Met Trp Ile Phe Ala Leu Thr Ala
        675                 680                 685

Gly Leu Phe Met Tyr Val Ala Leu Val Asp Met Val Pro Glu Met Leu
    690                 695                 700

His Asn Asp Ala Ser Asp His Gly Cys Ser Arg Trp Gly Tyr Phe Phe
705                 710                 715                 720

Leu Gln Asn Ala Gly Met Leu Leu Gly Phe Gly Ile Met Leu Leu Ile
                725                 730                 735

Ser Ile Phe Glu His Lys Ile Val Phe Arg Ile Asn Phe
            740                 745


<210> SEQ ID NO 85
<211> LENGTH: 741
<212> TYPE: PRT
<213> ORGANISM: Cynomolgous sp.

<400> SEQUENCE: 85

Met Ala Arg Lys Leu Ser Val Ile Leu Ile Leu Thr Phe Thr Leu Ser
1               5                   10                  15

Val Thr Asn Pro Leu His Glu Leu Lys Ser Ala Ala Ala Phe Pro Gln
            20                  25                  30

Thr Thr Glu Lys Ile Ser Pro Asn Trp Glu Ser Gly Ile Asn Val Asp
        35                  40                  45
```

```
Leu Ala Ile Thr Thr Arg Gln Tyr His Leu Gln Gln Leu Phe Tyr Arg
    50                  55                  60

Tyr Gly Glu Asn Asn Ser Leu Ser Val Glu Gly Phe Arg Lys Leu Leu
65                  70                  75                  80

Gln Asn Ile Gly Ile Asp Lys Ile Lys Arg Ile His Ile His His Asp
                85                  90                  95

His Asp His His Ser Asp His Glu His His Ser Asp His Glu His His
            100                 105                 110

Ser Asp His Glu His His Ser His Arg Asn His Ala Ala Ser Gly Lys
        115                 120                 125

Asn Lys Arg Lys Ala Leu Cys Pro Glu His Asp Ser Asp Ser Ser Gly
    130                 135                 140

Lys Asp Pro Arg Asn Ser Gln Gly Lys Gly Ala His Arg Pro Glu His
145                 150                 155                 160

Ala Asn Gly Arg Arg Asn Val Lys Asp Ser Val Ser Thr Ser Glu Val
                165                 170                 175

Thr Ser Thr Val Tyr Asn Thr Val Ser Glu Gly Thr His Phe Leu Glu
            180                 185                 190

Thr Ile Glu Thr Pro Lys Leu Phe Pro Lys Asp Val Ser Ser Ser Thr
        195                 200                 205

Pro Pro Ser Val Thr Glu Lys Ser Leu Val Ser Arg Leu Ala Gly Arg
    210                 215                 220

Lys Thr Asn Glu Ser Met Ser Glu Pro Arg Lys Gly Phe Met Tyr Ser
225                 230                 235                 240

Arg Asn Thr Asn Glu Asn Pro Gln Glu Cys Phe Asn Ala Ser Lys Leu
                245                 250                 255

Leu Thr Ser His Gly Met Gly Ile Gln Val Pro Leu Asn Ala Thr Glu
            260                 265                 270

Phe Asn Tyr Leu Cys Pro Ala Ile Ile Asn Gln Ile Asp Ala Arg Ser
        275                 280                 285

Cys Leu Ile His Thr Ser Glu Lys Lys Ala Glu Ile Pro Pro Lys Thr
    290                 295                 300

Tyr Ser Leu Gln Ile Ala Trp Val Gly Gly Phe Ile Ala Ile Ser Ile
305                 310                 315                 320

Ile Ser Phe Leu Ser Leu Leu Gly Val Ile Leu Val Pro Leu Met Asn
                325                 330                 335

Arg Val Phe Phe Lys Phe Leu Leu Ser Phe Leu Val Ala Leu Ala Val
            340                 345                 350

Gly Thr Leu Ser Gly Asp Ala Phe Leu His Leu Leu Pro His Ser His
        355                 360                 365

Ala Ser His His His Ser His Ser His Glu Glu Pro Ala Met Glu Met
    370                 375                 380

Lys Arg Gly Pro Leu Phe Ser His Leu Ser Ser Gln Asn Ile Glu Glu
385                 390                 395                 400

Ser Ala Tyr Phe Asp Ser Thr Trp Lys Gly Leu Thr Ala Leu Gly Gly
                405                 410                 415

Leu Tyr Phe Met Phe Leu Val Glu His Val Leu Thr Leu Ile Lys Gln
            420                 425                 430

Phe Lys Asp Lys Lys Lys Lys Asn Gln Lys Lys Pro Glu Asn Asp Asp
        435                 440                 445

Asp Val Glu Ile Lys Lys Gln Leu Ser Lys Tyr Glu Ser Gln Leu Ser
    450                 455                 460
```

```
Thr Asn Glu Glu Lys Val Asp Thr Asp Asp Arg Thr Glu Gly Tyr Leu
465                 470                 475                 480

Arg Ala Asp Ser Gln Glu Pro Ser His Phe Asp Ser Gln Gln Pro Ala
                485                 490                 495

Ile Leu Glu Glu Glu Glu Val Met Ile Ala His Ala His Pro Gln Glu
            500                 505                 510

Val Tyr Asn Glu Tyr Val Pro Arg Gly Cys Lys Asn Lys Cys His Ser
        515                 520                 525

His Phe His Asp Thr Leu Gly Gln Ser Asp Asp Leu Ile His His His
    530                 535                 540

His Asp Tyr His His Ile Leu His His His His His Gln Asn His His
545                 550                 555                 560

Pro His Ser His Ser Gln Arg Tyr Ser Arg Glu Glu Leu Lys Asp Ala
                565                 570                 575

Gly Ile Ala Thr Leu Ala Trp Met Val Ile Met Gly Asp Gly Leu His
            580                 585                 590

Asn Phe Ser Asp Gly Leu Ala Ile Gly Ala Ala Phe Thr Glu Gly Leu
        595                 600                 605

Ser Ser Gly Leu Ser Thr Ser Val Ala Val Phe Cys His Glu Leu Pro
    610                 615                 620

His Glu Leu Gly Asp Phe Ala Val Leu Leu Lys Ala Gly Met Thr Val
625                 630                 635                 640

Lys Gln Ala Val Leu Tyr Asn Ala Leu Ser Ala Met Leu Ala Tyr Leu
                645                 650                 655

Gly Met Ala Thr Gly Ile Phe Ile Gly His Tyr Ala Glu Asn Val Ser
            660                 665                 670

Met Trp Ile Phe Ala Leu Thr Ala Gly Leu Phe Met Tyr Val Ala Leu
        675                 680                 685

Val Asp Met Val Pro Glu Met Leu His Asn Asp Ala Ser Asp His Gly
    690                 695                 700

Cys Ser Arg Trp Gly Tyr Phe Phe Leu Gln Asn Ala Gly Met Leu Leu
705                 710                 715                 720

Gly Phe Gly Ile Met Leu Leu Ile Ser Ile Phe Glu His Lys Ile Val
                725                 730                 735

Phe Arg Ile Asn Phe
            740


<210> SEQ ID NO 86
<211> LENGTH: 120
<212> TYPE: PRT
<213> ORGANISM: Artificial Sequence
<220> FEATURE:
<223> OTHER INFORMATION: Synthesized

<400> SEQUENCE: 86

Gln Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Glu Asp Tyr
            20                  25                  30

Tyr Met His Trp Val Lys Gln Arg Pro Lys Gln Gly Leu Glu Trp Ile
        35                  40                  45

Gly Trp Ile Asp Pro Glu Asn Gly Asp Thr Glu Tyr Ala Pro Thr Phe
    50                  55                  60

Gln Gly Lys Ala Thr Met Thr Ala Asp Thr Ser Ser Asn Thr Ala Tyr
65                  70                  75                  80
```

```
Leu Gln Leu Ser Ser Leu Thr Ser Glu Asp Thr Ala Val Tyr Tyr Cys
                85                  90                  95

Asn Val His Asp Ala His Tyr Gly Thr Trp Phe Ala Tyr Trp Gly Gln
            100                 105                 110

Gly Thr Leu Val Thr Val Ser Ala
        115                 120


<210> SEQ ID NO 87
<211> LENGTH: 113
<212> TYPE: PRT
<213> ORGANISM: Artificial Sequence
<220> FEATURE:
<223> OTHER INFORMATION: Synthesized

<400> SEQUENCE: 87

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Ile Arg Asn
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg


<210> SEQ ID NO 88
<211> LENGTH: 120
<212> TYPE: PRT
<213> ORGANISM: Artificial Sequence
<220> FEATURE:
<223> OTHER INFORMATION: Synthesized

<400> SEQUENCE: 88

Glu Val Gln Leu Gln Gln Ser Gly Ala Glu Leu Val Arg Ser Gly Ala
1               5                   10                  15

Ser Val Lys Leu Ser Cys Thr Ala Ser Gly Leu Asn Ile Glu Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Gly Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Gly Asp Thr Ala Val Tyr Tyr Cys
                85                  90                  95

Thr Val His Asn Ala His Tyr Gly Thr Trp Phe Ala Tyr Trp Gly Gln
            100                 105                 110

Gly Thr Leu Val Thr Val Ser Ala
        115                 120
```

-continued

```
<210> SEQ ID NO 89
<211> LENGTH: 113
<212> TYPE: PRT
<213> ORGANISM: Artificial Sequence
<220> FEATURE:
<223> OTHER INFORMATION: Synthesized

<400> SEQUENCE: 89

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Ser Gly Asn Thr Tyr Leu Glu Trp Tyr Leu Gln Arg Pro Gly Gln Ser
        35                  40                  45

Pro Lys Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Tyr Thr Phe Gly Gly Gly Thr Lys Leu Glu Ile Lys
            100                 105                 110

Arg


<210> SEQ ID NO 90
<211> LENGTH: 4
<212> TYPE: PRT
<213> ORGANISM: Artificial Sequence
<220> FEATURE:
<223> OTHER INFORMATION: Synthesized

<400> SEQUENCE: 90

Gly Phe Leu Gly
1
```

What is claimed is:

1. A humanized antibody, that specifically binds human LIV-1 comprising a mature heavy chain variable region comprising three CDRs of SEQ ID NO:53 and having an amino acid sequence at least 95% identical to SEQ ID NO:53 provided that position H27 is occupied by L, position H29 is occupied by I, H30 by E and H94 by V and a mature light chain variable region comprising three CDRs of SEQ ID NO:60 at least 95% identical to SEQ ID NO:60 provided position L36 is occupied by Y and position L46 by P.

2. The humanized antibody of claim 1, further provided position H76 is occupied by N.

3. The humanized antibody of claim 1 wherein the mature heavy chain variable region is fused to a heavy chain constant region and the mature light chain variable region is fused to a light chain constant region.

4. The humanized antibody of claim 3, wherein the heavy chain constant region is a mutant form of a natural human constant region which has reduced binding to an Fcgamma receptor relative to the natural human constant region.

5. The humanized antibody of claim 3, wherein the heavy chain constant region is of IgG1 isotope.

6. The humanized antibody of claim 3, wherein the heavy chain constant region has an amino acid sequence comprising SEQ ID NO:44 and the light chain constant region has an amino acid sequence comprising SEQ ID NO:42.

7. The humanized antibody of claim 3, wherein the heavy chain constant region has an amino acid sequence comprising SEQ ID NO:46 (S239C) and the light chain constant region has an amino acid sequence comprising SEQ ID NO:42.

8. The humanized antibody of claim 1, wherein the mature heavy chain variable region has an amino acid sequence designated SEQ ID NO:52 or 53 and the mature light chain variable region has an amino acid sequence designated SEQ ID NO: 59 or 60.

9. The humanized antibody of claim 1, wherein the mature heavy chain variable region has an amino acid sequence designated SEQ ID NO:53 and the mature light chain variable region has an amino acid sequence designated SEQ ID NO:60.

10. The humanized antibody of claim 1, wherein the antibody is conjugated to a cytotoxic or cytostatic agent.

11. The humanized antibody of claim 1, having an association constant for human or cynomolgus monkey LIV-1 of 0.5 to $2\times10^9$ $M^{-1}$.

12. A nucleic acid encoding [a] *the* mature heavy chain variable region and/or [a] *the* mature light chain variable region as defined by claim 1.

13. A method of treating a patient having a cancer expressing LIV-1, comprising administering to the patient an effective regime of [a] *the* humanized antibody of claim 1.

14. The method of claim 13, wherein the cancer is a breast cancer, a prostate cancer, a cervical cancer or a melanoma.

15. A pharmaceutical composition comprising [a] *the* humanized antibody of claim 1.

16. The method of claim 13, wherein the antibody is conjugated to a cytotoxic or cytostatic agent.

17. The method of claim 13, wherein the isotype of the antibody is human IgG1.

*18. A vector comprising the nucleic acid of claim 12.*

*19. The vector of claim 18, wherein the vector is an expression vector.*

*20. A host cell comprising the nucleic acid of claim 12.*

*21. The host cell of claim 20, wherein the host cell is a Chinese hamster ovary (CHO) cell.*

*22. A method of producing an anti-LIV-1 antibody comprising culturing the host cell of claim 20 under a condition suitable for production of the anti-LIV-1 antibody.*

*23. The method of claim 22, further comprising isolating the anti-LIV-1 antibody produced by the host cell.*

*24. A method of producing an anti-LIV-1 antibody-drug conjugate comprising culturing the host cell of claim 20 under a condition suitable for production of an anti-LIV-1 antibody; isolating the anti-LIV-1 antibody produced from the host cell; and conjugating the anti-LIV-1 antibody to a cytotoxic or cytostatic agent.*

*25. The method of claim 24, wherein the cytotoxic or cytostatic agent is an antitubulin agent.*

*26. The method of claim 24, wherein the cytotoxic or cytostatic agent is an auristatin.*

*27. The method of claim 26, wherein the auristatin is monomethyl auristatin E.*

*28. The method of claim 26, wherein the auristatin is monomethyl auristatin F.*

*29. The method of claim 24, wherein the anti-LIV-1 antibody is conjugated to the cytotoxic or cytostatic agent via a linker.*

*30. The method of claim 29, wherein the linker is a cleavable peptide linker.*

*31. The method of claim 30, wherein the cleavable peptide linker has a formula:*

$$-A_a-W_w—Y_y—,$$

*wherein:*

*-A- is a stretcher unit;*

*a is 0 or 1;*

*each —W— is independently an amino acid unit;*

*w is independently an integer ranging from 0 to 12;*

*–Y— is a spacer unit; and*

*y is 0, 1 or 2.*

*32. The method of claim 29, wherein the linker is attached to sulphydryl residues of the humanized antibody obtained by partial reduction or full reduction of the humanized antibody.*

*33. The method of claim 29, wherein the cytotoxic or cytostatic agent is monomethyl auristatin E.*

*34. The method of claim 33, wherein the anti-LIV-1 antibody-drug conjugate has the following structure:*

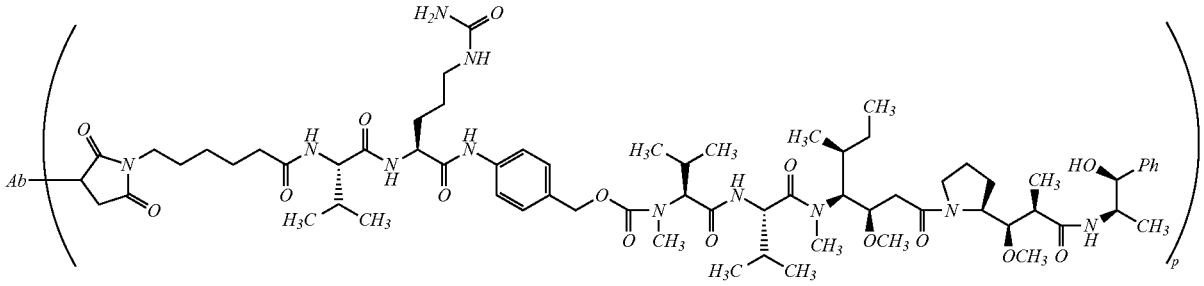

*wherein p denotes a number from 1 to 8 and Ab designates the anti-LIV-1 antibody.*

*35. The method of claim 34, wherein the average value of p in a population of the antibody-drug conjugate is about 4.*

*36. A nucleic acid encoding the mature heavy chain variable region and/or the mature light chain variable region as defined by claim 9.*

*37. A vector comprising the nucleic acid of claim 36.*

*38. The vector of claim 37, wherein the vector is an expression vector.*

*39. A host cell comprising the nucleic acid of claim 36.*

*40. The host cell of claim 39, wherein the host cell is a Chinese hamster ovary (CHO) cell.*

*41. A method of producing an anti-LIV-1 antibody comprising culturing the host cell of claim 39 under a condition suitable for production of the anti-LIV-1 antibody.*

*42. The method of claim 41, further comprising isolating the anti-LIV-1 antibody produced by the host cell.*

*43. A method of producing an anti-LIV-1 antibody-drug conjugate comprising culturing the host cell of claim 39 under a condition suitable for production of an anti-LIV-1 antibody; isolating the anti-LIV-1 antibody produced from the host cell; and conjugating the anti-LIV-1 antibody to a cytotoxic or cytostatic agent.*

*44. The method of claim 43, wherein the cytotoxic or cytostatic agent is an antitubulin agent.*

*45. The method of claim 43, wherein the cytotoxic or cytostatic agent is an auristatin.*

*46. The method of claim 45, wherein the auristatin is monomethyl auristatin E.*

*47. The method of claim 45, wherein the auristatin is monomethyl auristatin F.*

*48. The method of claim 43, wherein the anti-LIV-1 antibody is conjugated to the cytotoxic or cytostatic agent via a linker.*

*49. The method of claim 48, wherein the linker is a cleavable peptide linker.*

*50. The method of claim 49, wherein the cleavable peptide linker has a formula:*

$$-A_a-W_w—Y_y—$$

*wherein:*

*-A- is a stretcher unit;*

*a is 0 or 1;*

*each —W— is independently an amino acid unit;*

*w is independently an integer ranging from 0 to 12;*

*—Y— is a spacer unit; and*

*y is 0, 1 or 2.*

*51. The method of claim 48, wherein the linker is attached to sulphydryl residues of the humanized antibody obtained by partial reduction or full reduction of the humanized antibody.*

52. The method of claim 48, wherein the cytotoxic or cytostatic agent is monomethyl auristatin E.

53. The method of claim 52, wherein the anti-LIV-1 antibody-drug conjugate has the following structure:

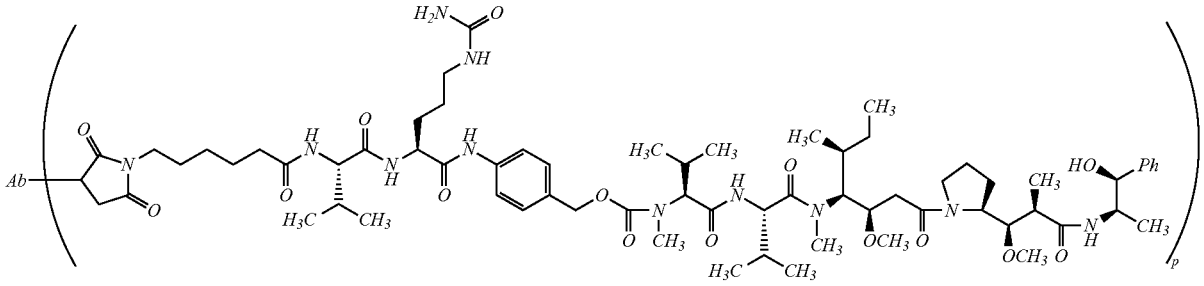

wherein p denotes a number from 1 to 8 and Ab designates the anti-LIV-1 antibody.

54. The method of claim 53, wherein the average value of p in a population of the antibody-drug conjugate is about 4.

55. The humanized antibody of claim 6, wherein the mature heavy chain variable region has an amino acid sequence designated SEQ ID NO:53 and the mature light chain variable region has an amino acid sequence designated SEQ ID NO:60.

56. The humanized antibody of claim 10, wherein the cytotoxic or cytostatic agent is an antitubulin agent.

57. The humanized antibody of claim 10, wherein the cytotoxic or cytostatic agent is an auristatin.

58. The humanized antibody of claim 57, wherein the auristatin is monomethyl auristatin E.

59. The humanized antibody of claim 57, wherein the auristatin is monomethyl auristatin F.

60. The humanized antibody of claim 10, further comprising a linker between the humanized antibody and the cytotoxic or cytostatic agent.

61. The humanized antibody of claim 60, wherein the linker is a cleavable peptide linker.

62. The humanized antibody of claim 61, wherein the cleavable peptide linker has a formula:

$$-A_a-W_w—Y_y—,$$

wherein:

-A- is a stretcher unit;

a is 0 or 1;

each —W— is independently an amino acid unit;

w is independently an integer ranging from 0 to 12;

—Y— is a spacer unit; and y is 0, 1 or 2.

63. The humanized antibody of claim 60, wherein the linker is attached to sulphydryl residues of the humanized antibody obtained by partial reduction or full reduction of the humanized antibody.

64. The humanized antibody of claim 60, wherein the cytotoxic or cytostatic agent is monomethyl auristatin E.

65. The humanized antibody of claim 64, wherein the linker is attached to monomethyl auristatin E forming an antibody-drug conjugate having the structure:

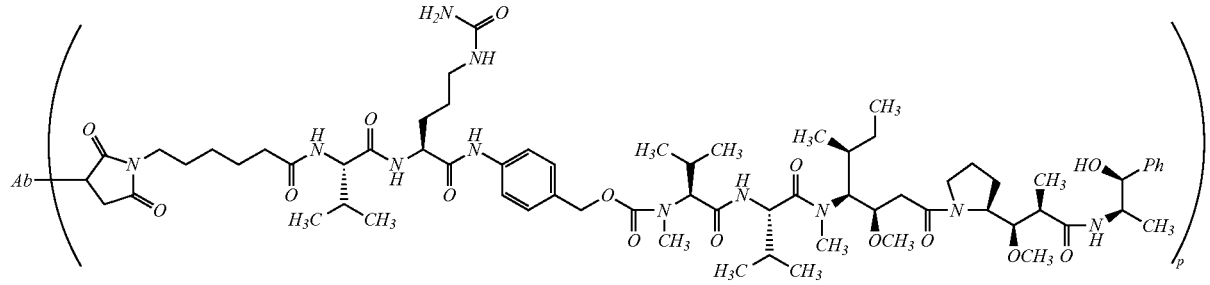

wherein p denotes a number from 1 to 8 and Ab designates the humanized antibody.

66. The humanized antibody of claim 65, wherein the average value of p in a population of the antibody-drug conjugate is about 4.

67. The humanized antibody of claim 6, wherein the antibody is conjugated to a cytotoxic or cytostatic agent.

68. The humanized antibody of claim 67, wherein the cytotoxic or cytostatic agent is an antitubulin agent.

69. The humanized antibody of claim 67, wherein the cytotoxic or cytostatic agent is an auristatin.

70. The humanized antibody of claim 69, wherein the auristatin is monomethyl auristatin E.

71. The humanized antibody of claim 69, wherein the auristatin is monomethyl auristatin F.

72. The humanized antibody of claim 67, further comprising a linker between the humanized antibody and the cytotoxic or cytostatic agent.

73. The humanized antibody of claim 72, wherein the linker is a cleavable peptide linker.

74. The humanized antibody of claim 73, wherein the cleavable peptide linker has a formula:

$$-A_a-W_w—Y_y—,$$

wherein:

-A- is a stretcher unit;

α is 0 or 1;

each —W— is independently an amino acid unit;

w is independently an integer ranging from 0 to 12;

—Y— is a spacer unit; and y is 0, 1 or 2.

75. The humanized antibody of claim 72, wherein the linker is attached to sulphydryl residues of the humanized antibody obtained by partial reduction or full reduction of the humanized antibody.

76. The humanized antibody of claim 72, wherein the cytotoxic or cytostatic agent is monomethyl auristatin E.

77. The humanized antibody of claim 76, wherein the linker is attached to monomethyl auristatin E forming an antibody-drug conjugate having the structure:

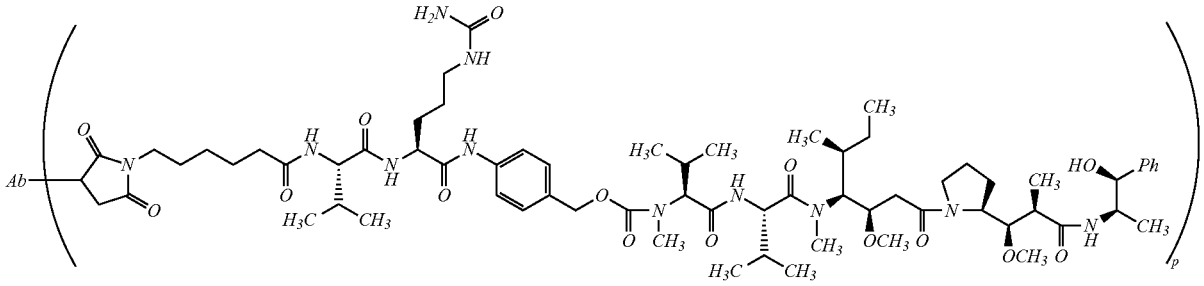

wherein p denotes a number from 1 to 8 and Ab designates the humanized antibody.

78. The humanized antibody of claim 77, wherein the average value of p in a population of the antibody-drug conjugate is about 4.

79. The humanized antibody of claim 9, wherein the antibody is conjugated to a cytotoxic or cytostatic agent.

80. The humanized antibody of claim 79, wherein the cytotoxic or cytostatic agent is an antitubulin agent.

81. The humanized antibody of claim 79, wherein the cytotoxic or cytostatic agent is an auristatin.

82. The humanized antibody of claim 81, wherein the auristatin is monomethyl auristatin E.

83. The humanized antibody of claim 81, wherein the auristatin is monomethyl auristatin F.

84. The humanized antibody of claim 79, further comprising a linker between the humanized antibody and the cytotoxic or cytostatic agent.

85. The humanized antibody of claim 84, wherein the linker is a cleavable peptide linker.

86. The humanized antibody of claim 85, wherein the cleavable peptide linker has a formula:

$$-A_a-W_w—Y_y—,$$

wherein:

-A- is a stretcher unit;

a is 0 or 1;

each —W— is independently an amino acid unit;

w is independently an integer ranging from 0 to 12;

—Y— is a spacer unit; and y is 0, 1 or 2.

87. The humanized antibody of claim 84, wherein the linker is attached to sulphydryl residues of the humanized antibody obtained by partial reduction or full reduction of the humanized antibody.

88. The humanized antibody of claim 84, wherein the cytotoxic or cytostatic agent is monomethyl auristatin E.

89. The humanized antibody of claim 88, wherein the linker is attached to monomethyl auristatin E forming an antibody-drug conjugate having the structure:

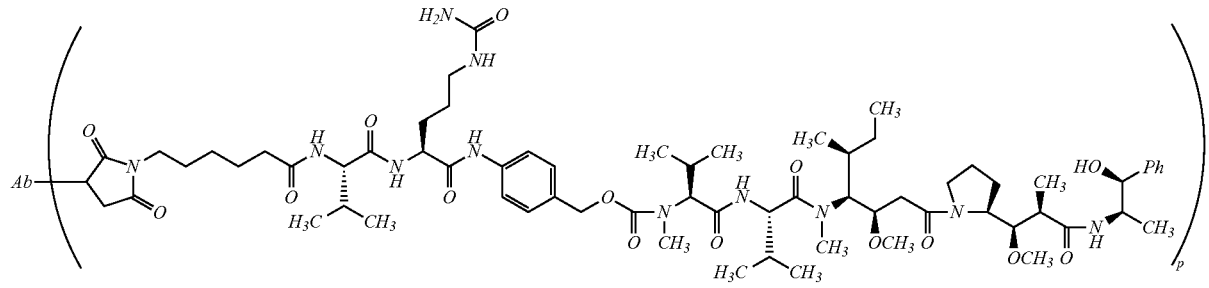

*wherein p denotes a number from 1 to 8 and Ab designates the humanized antibody.*

*90. The humanized antibody of claim 89, wherein the average value of p in a population of the antibody-drug conjugate is about 4.*

*91. The humanized antibody of claim 55, wherein the antibody is conjugated to a cytotoxic or cytostatic agent.*

*92. The humanized antibody of claim 91, wherein the cytotoxic or cytostatic agent is an antitubulin agent.*

*93. The humanized antibody of claim 91, wherein the cytotoxic or cytostatic agent is an auristatin.*

*94. The humanized antibody of claim 93, wherein the auristatin is monomethyl auristatin E.*

*95. The humanized antibody of claim 93, wherein the auristatin is monomethyl auristatin F.*

*96. The humanized antibody of claim 91, further comprising a linker between the humanized antibody and the cytotoxic or cytostatic agent.*

*97. The humanized antibody of claim 96, wherein the linker is a cleavable peptide linker.*

*98. The humanized antibody of claim 97, wherein the cleavable peptide linker has a formula:*

$$-A_a-W_W—Y_y—,$$

*wherein:*

*-A- is a stretcher unit;*

*a is 0 or 1;*

*each —W— is independently an amino acid unit;*

*w is independently an integer ranging from 0 to 12;*

*—Y— is a spacer unit; and*

*y is 0, 1 or 2.*

*99. The humanized antibody of claim 96, wherein the linker is attached to sulphydryl residues of the humanized antibody obtained by partial reduction or full reduction of the humanized antibody.*

*100. The humanized antibody of claim 96, wherein the cytotoxic or cytostatic agent is monomethyl auristatin E.*

*101. The humanized antibody of claim 100, wherein the linker is attached to monomethyl auristatin E forming an antibody-drug conjugate having the structure:*

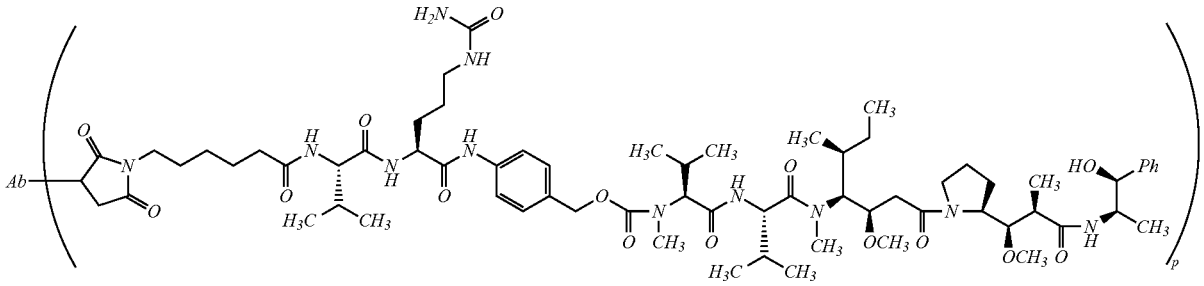

*wherein p denotes a number from 1 to 8 and Ab designates the humanized antibody.*

*102. The humanized antibody of claim 101, wherein the average value of p in a population of the antibody-drug conjugate is about 4.*

*103. A pharmaceutical composition comprising the humanized antibody of claim 6.*

*104. A pharmaceutical composition comprising the humanized antibody of claim 9.*

*105. A pharmaceutical composition comprising the humanized antibody of claim 55.*

*106. A pharmaceutical composition comprising the antibody-drug conjugate of claim 65.*

*107. A pharmaceutical composition comprising the antibody-drug conjugate of claim 101.*

*108. The method of claim 14, wherein the breast cancer is triple negative breast cancer.*

*109. A method of treating a patient having a cancer expressing LIV-1, comprising administering to the patient an effective regime of the humanized antibody of claim 55.*

*110. The method of claim 109, wherein the cancer is a breast cancer, a prostate cancer, a cervical cancer or a melanoma.*

*111. The method of claim 110, wherein the breast cancer is triple negative breast cancer.*

*112. A method of treating a patient having a cancer expressing LIV-1, comprising administering to the patient an effective regime of the antibody-drug conjugate of claim 65.*

*113. The method of claim 112, wherein the cancer is a breast cancer, a prostate cancer, a cervical cancer or a melanoma.*

*114. The method of claim 113, wherein the breast cancer is triple negative breast cancer.*

*115. A method of treating a patient having a cancer expressing LIV-1, comprising administering to the patient an effective regime of the antibody-drug conjugate of claim 101.*

*116. The method of claim 115, wherein the cancer is a breast cancer, a prostate cancer, a cervical cancer or a melanoma.*

*117. The method of claim 116, wherein the breast cancer is triple negative breast cancer.*

*118. A pharmaceutical composition comprising an antibody-drug conjugate, wherein the antibody-drug conjugate comprises a humanized antibody conjugated to monomethyl auristatin E, wherein the humanized antibody specifically binds to human LIV-1 and comprises a mature heavy chain variable region comprising the amino acid sequence of SEQ ID NO:53 and a mature light chain variable region comprising the amino acid sequence of SEQ ID NO:60, wherein the mature heavy chain variable region is fused to an IgG1 isotype heavy chain constant region comprising the amino acid sequence of SEQ ID NO:44 and the mature light chain variable region is fused to a light chain constant region comprising the amino acid sequence of SEQ ID NO:42,*

*wherein the antibody-drug conjugate further comprises a linker between the humanized antibody and the monomethyl auristatin E, wherein the antibody-drug conjugate has the structure:*

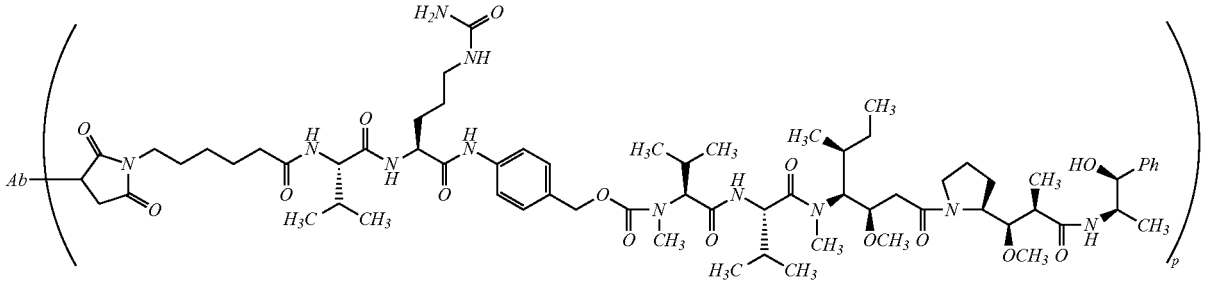

*wherein p denotes a number from 1 to 8 and Ab designates the humanized antibody.*

*119. The pharmaceutical composition of claim 118, wherein the average value of p in a population of the antibody-drug conjugate is about 4.*

*120. An antibody-drug conjugate comprising a humanized antibody conjugated to monomethyl auristatin E, wherein the humanized antibody specifically binds to human LIV-1 and comprises a mature heavy chain variable region comprising the amino acid sequence of SEQ ID NO:53 and a mature light chain variable region comprising the amino acid sequence of SEQ ID NO:60, wherein the mature heavy chain variable region is fused to an IgG1 isotype heavy chain constant region comprising the amino acid sequence of SEQ ID NO:44 and the mature light chain variable region is fused to a light chain constant region comprising the amino acid sequence of SEQ ID NO:42, wherein the antibody-drug conjugate further comprises a linker between the humanized antibody and the monomethyl auristatin E, wherein the antibody-drug conjugate has the structure:*

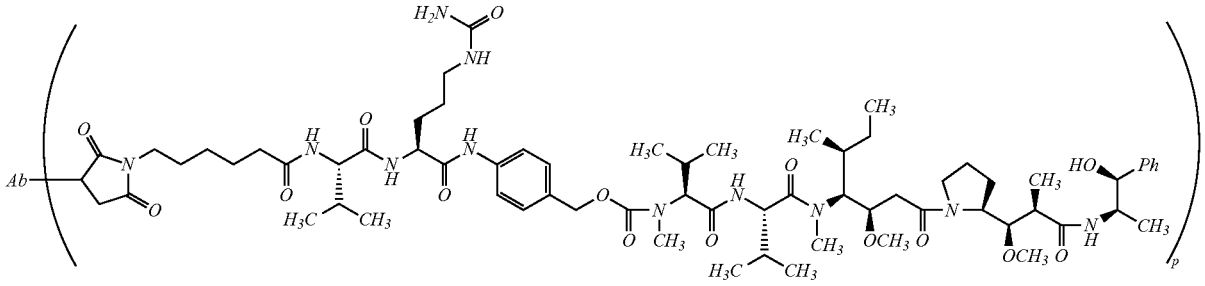

*wherein p denotes a number from 1 to 8 and Ab designates the humanized antibody.*

*121. The antibody-drug conjugate of claim 120, wherein the average value of p in a population of the antibody-drug conjugate is about 4.*

*122. A method of treating a patient having a cancer expressing LIV-1, comprising administering to the patient an effective regime of the antibody-drug conjugate of claim 120.*

*123. The method of claim 122, wherein the cancer is a breast cancer, a prostate cancer, a cervical cancer or a melanoma.*

*124. The method of claim 123, wherein the breast cancer is triple negative breast cancer.*

* * * * *